US011058455B2

(12) United States Patent
Cosman, Jr.

(10) Patent No.: US 11,058,455 B2
(45) Date of Patent: Jul. 13, 2021

(54) CATHETER SYSTEM

(71) Applicant: Cosman Medical Inc., Burlington, MA (US)

(72) Inventor: Eric R. Cosman, Jr., Belmont, MA (US)

(73) Assignee: Cosman Medical Inc., Burlington, MA (US)

( * ) Notice: Subject to any disclaimer, the term of this patent is extended or adjusted under 35 U.S.C. 154(b) by 511 days.

(21) Appl. No.: 15/442,106

(22) Filed: Feb. 24, 2017

(65) Prior Publication Data

US 2017/0258490 A1    Sep. 14, 2017

Related U.S. Application Data

(63) Continuation of application No. 14/020,752, filed on Sep. 6, 2013, now abandoned, which is a continuation-in-part of application No. 13/776,685, filed on Feb. 25, 2013, now abandoned.

(51) Int. Cl.

| A61B 17/34 | (2006.01) |
|---|---|
| A61M 25/01 | (2006.01) |
| A61M 25/06 | (2006.01) |
| A61N 1/05 | (2006.01) |
| A61N 1/06 | (2006.01) |
| A61N 1/36 | (2006.01) |
| A61N 5/00 | (2006.01) |
| A61B 18/18 | (2006.01) |
| A61B 18/12 | (2006.01) |
| A61B 18/14 | (2006.01) |
| A61B 18/00 | (2006.01) |

(52) U.S. Cl.
CPC ...... *A61B 17/3415* (2013.01); *A61B 17/3401* (2013.01); *A61B 18/1206* (2013.01); *A61B 18/1492* (2013.01); *A61B 18/18* (2013.01); *A61M 25/0102* (2013.01); *A61M 25/065* (2013.01); *A61M 25/0662* (2013.01); *A61N 1/0551* (2013.01); *A61N 1/06* (2013.01); *A61N 1/36* (2013.01); *A61N 5/00* (2013.01); *A61B 2018/0044* (2013.01); *A61B 2018/00083* (2013.01); *A61B 2018/00577* (2013.01); *A61B 2018/00821* (2013.01); *A61B 2018/1435* (2013.01); *A61B 2218/002* (2013.01); *A61M 2025/0681* (2013.01)

(58) Field of Classification Search
CPC ............ A61B 17/3415; A61B 17/3401; A61B 18/1206; A61B 18/1492; A61B 18/18; A61B 2018/00083; A61B 2018/0044; A61B 2018/00577; A61B 2018/00821; A61B 2018/1435; A61B 2218/002; A61M 25/0102; A61M 25/065; A61M 25/0662; A61M 2025/0681; A61N 1/0551; A61N 1/06; A61N 1/36; A61N 5/00
USPC .......................................................... 607/46
See application file for complete search history.

(56) References Cited

U.S. PATENT DOCUMENTS 5,935,123 A * 8/1999 Edwards ................ A61N 5/045
606/41
7,862,563 B1 * 1/2011 Cosman ............ A61B 18/1477
606/41

(Continued)

*Primary Examiner* — Erin M Piateski
(74) *Attorney, Agent, or Firm* — Kacvinsky Daisak Bluni PLLC

(57) ABSTRACT

An injection adaptor hub for a medical catheter.

11 Claims, 23 Drawing Sheets

(56) References Cited

U.S. PATENT DOCUMENTS

| | | | | |
|---|---|---|---|---|
| 2002/0077683 | A1* | 6/2002 | Westlund | A61N 1/056 607/116 |
| 2004/0147963 | A1* | 7/2004 | Sommer | A61M 25/0082 607/3 |
| 2004/0210290 | A1* | 10/2004 | Omar-Pasha | A61N 1/0529 607/116 |
| 2006/0173407 | A1* | 8/2006 | Shaughnessy | A61B 1/00158 604/95.01 |
| 2006/0178666 | A1* | 8/2006 | Cosman | A61B 18/148 606/41 |
| 2012/0185022 | A1* | 7/2012 | Noda | A61F 7/12 607/106 |

* cited by examiner

CATHETER SYSTEM

CLAIM OF PRIORITY

This application is a continuation of U.S. application Ser. No. 14/020,752, filed on Sep. 6, 2013, which is a continuation-in-part of U.S. application Ser. No. 13/776,685, filed on Feb. 25, 2013, now abandoned, each of which is incorporated by reference in its entirety.

TECHNICAL FIELD OF THE INVENTION

This invention relates generally to medical catheters and catheter introducer needles.

BACKGROUND OF THE INVENTION

The use of radiofrequency (RF) generators and electrodes to be applied to tissue for pain relief or functional modification is well known. For example, the RFG-3B RF lesion generator of Radionics, Inc., Burlington, Mass. and its associated electrodes enable electrode placement of the electrode near target tissue and heating of the target tissue by RF power dissipation of the RF signal output in the target tissue. For example, the G4 generator of Cosman Medical, Inc., Burlington, Mass. and its associated electrodes such as the Cosman CSK, and cannula such as the Cosman CC and RFK cannula, enable electrode placement of the electrode near target tissue and heating of the target tissue by RF power dissipation of the RF signal output in the target tissue. Temperature monitoring of the target tissue by a temperature sensor in the electrode can control the process. Heat lesions with target tissue temperatures of 60 to 95 degrees Celsius are common. Tissue dies by heating above about 45 degrees Celsius, so this process produces the RF heat lesion. RF generator output is also applied using a pulsed RF method, whereby RF output is applied to tissue intermittently such that tissue is exposed to high electrical fields and average tissue temperature are lower, for example 42 degrees Celsius or less.

RF generators and electrodes are used to treat pain, cancer, heart defects, high blood pressure, uterine fibroids, sleep apenea, and other diseases. Examples are the equipment and applications of Cosman Medical, Inc., Burlington, Mass. such as the G4 radiofrequency generator, the CSK electrode, CC cannula, RFK cannula, and DGP-PM ground pad. Related information is given in the paper by Cosman E R and Cosman B J, "Methods of Making Nervous System Lesions", in Wilkins R H, Rengachary S (eds.); Neurosurgery, New York, McGraw Hill, Vol. 3, 2490-2498; and is hereby incorporated by reference in its entirety. Related information is given in the book chapter by Cosman E R Sr and Cosman E R Jr. entitled "Radiofrequency Lesions.", in Andres M. Lozano, Philip L. Gildenberg, and Ronald R. Tasker, eds., Textbook of Stereotactic and Functional Neurosurgery (2nd Edition), 2009, and is hereby incorporated by reference in its entirety. A paper by Luigi Solbiati et al. entitled "Hepatic Metastases: Percutaneous Radiofrequency Ablation with Cool-Tip Electrodes," Radiology 1997, vol. 205, no. 2, pp. 367-373 describes various techniques and considerations relating to tissue ablation with RF electrodes which are internally-cooled by circulating fluid, and is incorporated herein by reference. A paper by Rosenthal et al entitled "Percutaneous Radiofrequency Treatment of Osteoid Osteoma," Seminars in Musculoskeletal Radiology, Vol. 1, No. 2, 1997 reports the treatment of a primary benign bone tumor using a percutaneously placed radiofrequency electrode, and is incorporated herein by reference.

Radiofrequency cannula include a hollow metal shaft, a hub at the proximal end, an injection port, electrical insulation covering the proximal end of the metal shaft, and a length of shaft at the distal end that is not covered by electrical insulation and is referred to as the active tip. An RF cannula can include a removable stylet that includes a cap at its proximal end that engages with the cannula hub, and a solid rod that can occlude the inner lumen of the hollow shafts. The stylet can be positioned with in the inner lumen of the cannula's hollow metal shaft when the cannula is used to penetrate tissue. The stylet can be removed from the cannula's inner lumen, and fluid injected into the hub is conducted to and outflows from a hole in the cannula's distal end. The hub typically includes a luer injection port. An RF electrode can be placed in the cannula's inner lumen, and the electrode can be connected to an RF generator, so that electrical signals from the generator, including nerve stimulation and RF signals, are conducted to the cannula and thus to tissue in contact with the cannula's active tip. The RF electrode can include a temperature sensor and can be position within the cannula to monitoring a temperature within the cannula's active tip. In one embodiment, an RF cannula has a flat, sharp bevel at the distal end of the cannula shaft; the bevel is characteristic of spinal needles used for nerve block procedures. Examples of a sharp RF cannula include the CC cannula and RFK cannula, both manufactured by Cosman Medical, Inc. of Burlington, Mass. In another embodiment, an RF cannula's shaft includes a closed distal end and a hole on the side for outflow of injected fluids. Examples of blunt-tip RF cannula include the blunt tip RFK cannula. The shaft of an RF cannula can be straight, such as in the example of the CC cannula. The shaft of an RF cannula can be curved at its distal end, such as in the example of the RFK cannula. The curvature of the cannula can be 15 degrees or more. The curvature of the cannula can be configured to facilitate the manipulation of the cannula when it is placed within tissue. RF cannula are available in sizes 23, 22, 21, 20, 18, and 16 gauge. Examples of RF electrodes configured to be used with RF cannulae include the Cosman CSK electrode, Cosman TCD electrode, and Cosman TCN electrode. Such RF electrodes typically include a temperature sensor at their distal end to monitor the temperature of the active tip and tissue in contact with the active tip of the cannula. Such RF electrodes are thinner than RF cannula and RF electrode configured to be used without a cannula, for example 28 gauge. The length of such RF electrodes are match to the length of the RF cannulae with which they are intended to be used so that the temperature sensor include in the electrode's distal tip fall within the active tip of the cannula when the electrode is placed inside the cannula. The Cosman CSK and TCD electrodes have a shaft that is stainless steel. The Cosman TCN electrode has a shaft that is Nitinol. One limitation of such RF cannula and electrode systems, such as the Cosman CSK electrode and Cosman CC cannula, is that fluid injection into the cannula cannot be achieved when the electrode is positioned within the cannula. One limitation of such RF electrodes configured to be used with RF cannula is that they are not catheters. One limitation of such RF electrodes configured to be used with RF cannula is that they are not configured for placement in the epidural space. One limitation of such RF cannulae is that they are not flexible enough to be guided through the epidural space. One limitation of such RF cannulae with sharp bevels is that they have sharp cutting edges that can damage a catheter that is introduced into a living body though such a cannula. One limitation of such RF cannulae with sharp bevels is that they can damage the dura and other sensitive structures if placed in the epidural space. One limitation of such RF cannulae in the prior art is that their bevels are not configured both to reduce the likelihood of damage to the dura and to reduce damage a catheter when a catheter is introduced into the epidural space through an RF cannula. One limitation of such RF cannulae with sharp bevels is that they are not configured for the introduction of medical catheters, such as epidural catheters and catheter-type electrodes, into the human body. One limitation of blunt-tip RF cannulae is that they are not configured to introduce a catheter into the human body through their inner lumen. Related information is given in Cosman Medical brochure "Four Electrode RF Generator", brochure number 11682 rev A, copyright 2010, Cosman Medical, Inc., and is hereby incorporated by reference herein in its entirety.

In one embodiment, U.S. Pat. No. 7,862,563 by E R Cosman Sr and E R Cosman Jr presents a unitized injection electrode with an electrically-insulated shaft, an exposed metallic tip, a temperature sensor within the exposed metallic tip, cables that connect to the electrode via a single, flexible leader connector that splits into two parts of which the first is terminated by a connector configured to carry high-frequency and stimulation signals and temperature-measurement signals, and the second is terminated by an injection port through which fluid can be injected into the shaft and out the distal end of the electrode. One limitation of the prior art in U.S. Pat. No. 7,862,563 is that it does not show a unitized injection electrode for which the metallic tip and insulated shaft are constructed using a spring coil and a central stiffening wire. One limitation of the prior art in U.S. Pat. No. 7,862,563 is that it does not show the application of a unitized injection electrode in the epidural space.

Radiofrequency injection electrodes have a shaft including metal tubing with sharp distal end for insertion into tissue, for example to reach a spinal target. Example of RF injection electrodes include the the CU electrode, the CR electrode, and the CP electrode models, manufactured for Cosman Medical, Inc. in Burlington, Mass. Related information is given in Cosman Medical brochure "Four Electrode RF Generator", brochure number 11682 rev A, copyright 2010, Cosman Medical, Inc., and is hereby incorporated by reference herein in its entirety. The CU, CR, and CP models have shaft length lengths 6 cm (2.4 inches), 10 cm (3.9 inches), or 15 cm (5.9 inches). The shaft of an RF injection electrode in the prior art are configured to penetrate the skin surface, muscle, and other solid bodily tissues to enable percutaneous placement of the active tip at nerves outside and around the bony spinal column. The shaft of an RF injection electrodes in the prior art is electrically insulated except for uninsulated distal length, termed the active tip, has an electrical connection to a signal generator for delivery of stimulation or RF signal outputs to the target tissue via the active tip. Each RF injection electrode has a flexible injection tube and a port to allow injection of contrast, anaesthetic, or saline solution fluid to the target tissue. The CU electrode incorporates a temperature sensor positioned within the exposed, conductive tip portion. The CR and CP electrodes do not incorporate a temperature sensor. The CP electrode can be used to effect a stimulation-guided nerve block, whereby an electrical stimulation signal is applied to the CP electrode via its electrical connector, stimulation signals are applied to nerve tissue nearby the conductive tip of the CP electrode, and anesthetic fluid is injected through the CP shaft once desired stimulation response is achieved by positioning of the exposed tip. The CR electrode can be used to effect a stimulation-guided RF therapy without temperature control, whereby an electrical stimulation signal is applied to the CR electrode via its electrical connector, the stimulation signal is applied to nerve tissue nearby the conductive tip of the CR electrode in order to position the exposed tip of the electrode near target nerves, RF generator output is applied to the CR electrode via the same electrical connector, RF output is applied to tissue nearby the exposed tip of the electrode without temperature monitoring. The CR electrode can also be used to effect non-stimulation-guided RF therapy, whereby stimulation guidance is not utilized. The CU electrode can be used to effect a stimulation-guided RF therapy with temperature monitoring and control, whereby an electrical stimulation signal is applied to tissue via the CU electrode to position its exposed tip near target nerves, and RF output is applied to tissue near the exposed tip to effect medical treatment. The CU electrode can also be used to effect non-stimulation-guided RF therapy, whereby stimulation guidance is not utilized. One limitation of the prior art in RF injection electrodes is that they are not configured to be guided into and through the epidural space. One limitation of the prior art in RF injection electrodes is that their tips are sharp. One limitation of the prior art in RF injection electrodes is that their shaft does not include a spring coil. One limitation of the prior art in RF injection electrodes is that they are not introduced into the human body via an introducer needle. One limitation of the prior art in RF injection electrodes is that they are not configured to introduce a catheter into the human body.

In the prior art, the TEW electrode system, manufactured by Cosman Medical, Inc. of Burlington, Mass., includes an electrode with a spring-coil tip that has a temperature sensor at its distal closed end. Related information is given in Cosman Medical brochure "Four Electrode RF Generator", brochure number 11682 rev A, copyright 2010, Cosman Medical, Inc., and is hereby incorporated by reference herein in its entirety. The TEW electrode is introduced into the human body by means of a fully-electrically-insulated metal cannula. The TEW cannula does not have an active tip. The TEW cannula includes a sharp, flat bevel, and a removable stylet. The TEW electrode is designed for RF treatment of the trigeminal facial nerve via the foremen ovale of the human skull. The TEW electrode is not electrically insulated. The shaft of the TEW electrode is a metallic tube to the distal end of which is attached a spring coil. The coil tip of the TEW electrode is configured to emerge from the end of the cannula and into the body without diverging substantially from its predetermined curve. The TEW electrode's spring coil is no longer than 0.33 inches. The TEW electrode's spring coil emerges from the distal end of the cannula by no more than 0.33 inches. One limitation of the TEW electrode is that it is not configured to be threaded though the epidural space. One limitation of the TEW electrode is that it is not configured to be threaded through 12 inches to 34 inches of the epidural space. One limitation of the TEW electrode is that it is not long enough to apply RF therapy to multiple spinal nerves via a single skin puncture and the epidural space. One limitation of the TEW electrode is that it does not have an integral injection port. One limitation of the TEW electrode is that it is that it not configured to allow for outflow of fluids from its spring coil tip. One limitation of the TEW cannula is that it is configured for the introduction of a catheter into the human body. One limitation of the TEW cannula is that it does not have an active tip. One limitation of the TEW cannula is that when an electrode is placed within its inner lumen, electrical signals applied to the cannula by the electrode are not transmitted to tissue in contact with any substantial part of the cannula. One limitation of the TEW cannula is that it does not have an tip characteristic of an epidural needle. One limitation of the TEW cannula is that it is not configured for placement in the epidural space and to perform RF therapy in the epidural space.

In the prior art, the Flextrode RF electrode system, manufactured by Cosman Medical, Inc. of Burlington, Mass., includes an electrode and an introducer cannula. Related information is given in Cosman Medical brochure "Four Electrode RF Generator", brochure number 11682 rev A, copyright 2010, Cosman Medical, Inc., and is hereby incorporated by reference herein in its entirety. The flextrode electrode's shaft is approximately 15 cm (5.9 inches) in length and is constructed from a metal tube whose distal end has a spiral cut over the distal 1.25 inches. A temperature sensor is located at the distal, closed end of the shaft. The electrode is introduced into the human body via the introducer cannula which includes a sharped distal end with a flat bevel, and whose shaft is electrically insulated over substantially all of its length, except for at most 1-2 mm at the distal end. When the electrode is introduced through the cannula, 11 mm of the electrode extends beyond the cannulas distal end into the tissue. The Flextrode electrode is not electrically insulated. RF energy is applied to the tissue by the length of the Flextrode electrode that extends beyond the cannula's distal tip and the uninsulated distal tip of the cannula. The Flextrode is configured to penetrate tissue, such as the fibrous tissue of the intervertebral disc, where it emerges from the distal end of the cannula. The Flextrode's stiffness is configured so that its tip can move through the curved tip of the introducer cannula but remain substantially straight as it penetrates tissue. One limitation of the Flextrode electrode is that it is not configured for placement in the epidural space. One limitation of the Flextrode electrode is that it is configured for injection of fluids into the human body. One limitation of the Flextrode cannula is that its bevel is not configured for the introduction of catheters into the human body. One limitation of the Flextrode cannula is that its bevel is not configured for the introduction of catheters whose external surface is soft material, such a plastic, into the human body. One limitation of the Flextrode cannula is that its bevel is not an epidural bevel, such as a tuohy bevel, RX bevel, Wavepoint bevel, Cath Glide bevel, or the bevel shown in Higuchi. One limitation of the Flextrode cannula is that sharp surfaces of its bevel can damage a soft catheter passing through it.

The Radionics DiscTrode RF electrode system includes an electrode and an introducer cannula. Related information is given in an article by PM Finch entitled "The Use of Radiofrequency Heat Lesions in the Treatment of Lumbar Discogenic Pain", Pain Practice, Volume 2, Number 3, 2002, pages 235-240, which is here incorporated by reference herein in its entirety. The disctrode electrode's shaft is approximately 9 inches in length and is constructed from a metal tube whose distal end has thin cuts over the distal 2.5 inches. A temperature sensor is located at the distal, closed end of the shaft. The electrode is induced into the human body via the introducer cannula which has a sharped, flat bevel at its distal end, and whose shaft is substantially electrically insulated, except for 1-2 mm at the distal tip bevel. When the electrode is introduced through the cannula, 5 cm (2 inches) of the electrode extends beyond the cannula's distal end into the tissue. The disctrode electrode is not electrically insulated. RF energy is applied to the tissue by the length of the disctrode electrode that extends beyond the cannula's distal tip and the uninsulated distal tip of the cannula. The disctrode is configured to penetrate tissue, such as the fibrous tissue of the intervertebral disc, where it emerges from the distal end of the cannula. The disctrode's stiffness is configured so that its tip can move through the curved tip of the introducer cannula but remain substantially straight as it penetrates tissue. One limitation of the DiscTrode electrode is that it is not configured for placement in the epidural space. One limitation of the DiscTrode electrode is that it is configured for injection of fluids into the human body. One limitation of the DiscTrode cannula is that its bevel is not configured for the introduction of catheters into the human body. One limitation of the DiscTrode cannula is that its bevel is not configured for the introduction of catheters whose external surface is soft material, such a plastic, into the human body. One limitation of the DiscTrode cannula is that its bevel is not an epidural bevel, such as a tuohy bevel, RX bevel, Wavepoint bevel, Cath Glide bevel, or the bevel shown in Higuchi. One limitation of the DiscTrode cannula is that sharp surfaces of its bevel can damage a soft catheter passing through it.

The Oratec Spinecath system includes a catheter and an introducer cannula. Related information is given in an article by PM Finch entitled "The Use of Radiofrequency Heat Lesions in the Treatment of LumbarDiscogenic Pain", Pain Practice, Volume 2, Number 3, 2002, pages 235-240, which is here incorporated by reference herein in its entirety. The catheter's shaft consists of a resistive coil that is entirely covered by electrical insulation. RF energy applied to the coil heats the internal resistive coil and tissue is heated by thermal conduction. RF current is not applied to the tissue. A temperature sensor is located in the spinecath catheter. The electrode is induced into the human body via the introducer cannula which has a sharped, flat bevel at its distal end. The spinecath emerges from the distal end of the cannula by approximately 5 cm (2 inches). One limitation of the spinecath catheter is that it is not configured for placement in the epidural space. One limitation of the spinecath catheter is that it is not configured for injection of fluids into the human body. One limitation of the spinecath catheter is that it is not a radiofrequency electrode with an active tip. One limitation of the spinecath catheter is that it does not apply RF signals to tissue that are in contact with it. One limitation of the spinecath cannula is that it is not configured to function as an RF cannula. One limitation of the spinecath cannula is that it does not have an epidural bevel, such as a tuohy bevel, RX bevel, Wavepoint bevel, Cath Glide bevel, or the bevel shown in Higuchi. One limitation of the spinecath cannula is that it is not configured for introduction of epidural catheters. One limitation of the spinecath cannula is that it is not electrically insulated.

The use of catheters in the epidural space to treat pain is well known. A flexible catheter is introduced into the epidural space through an epidural needle inserted percutaneously through the sacral hiatus, through an intervertebral foramina, or through vertebral interspaces. An epidural needle includes a hollow metal shaft with inner lumen, an hub including a port such as a luer port, a distal bevel configured for placement in the epidural space, and a removable stylet rod configured for placement in the epidural space. The bevel of an epidural needle typically has rounded surfaces and edges configured to reduce the likelihood of damage to sensitive structures around the epidural space, to reduce the likelihood of penetration of the dura, and to reduce the likelihood of damage to a catheter that is introduced through the epidural needle's hollow shaft. Examples of epidural introducer needles include the touhy needle, the RX needle disclosed in U.S. Pat. No. 5,810,788 authored by Racz, and the Cath Glide needle manufactured by Spectra Medical Devices, Inc. of Wilmington, Mass. An injection adaptor is a separate device that can be attached to the proximal end of the catheter to provide for the injection of fluids into the proximal end of the catheter that outflow into patient anatomy through the distal end of the catheter. Examples of injection adaptors for epidural catheters include the tuohy-borst adaptor and the catheter connection hub disclosed in U.S. Pat. No. 8,038,667 authored by Racz and Bullard. Injection adaptors in the prior art have two openings, one distal opening into which the catheter is clamped with a fluid seal, and one proximal opening through which fluid can be injected and a stylet can be advanced into the inner lumen of the catheter; the proximal opening is typically a luer injection port, and the stylet wire must be removed in order that injections are made into the hub and thus the catheter. Techniques such as lysis of adhesions, chemical neurolysis of nerve roots, and other medial methods are well known. Related information is in "Epidural Lysis of Adhesions and Percutaneous Neuroplasty" by Gabor B. Racz, Miles R. Day, James E. Heavner, Jeffrey P. Smith, Jared Scott, Carl E. Noe, Laslo Nagy and Hana finer (2012), in the book "Pain Management—Current Issues and Opinions", Dr. Gabor Racz (Ed.), ISBN: 978-953-307-813-7, InTech, and is hereby incorporated by reference in its entirety. Examples of epidural catheters include the Tun-L-XL catheter manufactured by EpiMed International, Farmers Branch, Tex. The Tun-L-XL catheter comprises a stainless steel spring coil whose distal end is welded into a ball, and which is covered by a plastic tube over its entire length except for the distal end. The coil wire is closely coiled except for a region of the exposed, distal coil where the cool loops are loosely wound to provide for preferential outflow of injected fluids. The coil can have a metal safety strap welded at the proximal and distal end of the coil. A stylet comprising a metal wire and a plastic hub attached to the proximal end of the wire is inserted into the proximal end of the catheter to stiffen it. The stylet is removed, an injection adaptor is attached to the proximal end of the catheter, and fluids can be injected. Nerve stimulation signals can be delivered through the exposed metallic tip of the catheter by connecting the proximal end of the stylet to the output of a nerve stimulator, perhaps by means of an alligator clip, while the stylet is positioned inside the catheter. One limitation of the prior art in epidural catheters is that an electrode with a temperature monitoring is not used as a stylet. One limitation of the prior art in epidural catheters is that the stylet does not have an integrated connection cable to an electrical generator. One limitation of the prior art in epidural catheters is that the stylet does not have an integrated connection cable to an RF generator that includes both a wire for conducting an RF signals and a wire for conducting temperature signals. One limitation of the prior art in epidural catheters is that prior catheters do not provided for temperature-controlled RF lesioning. One limitation of the prior art in epidural catheters is prior catheter systems are not a unitized injection electrode. One limitation of the prior art in epidural catheters is prior catheter systems are not a unitized injection electrode whose shaft includes a spring coil. One limitation of the prior art in introducer needles for catheters is that the needles are not electrically insulated along their shafts. One limitation of the prior art in introducer needles for medical catheters is that the needles do not both provide a tip configured for introduction of a catheter, and provide an insulated shaft that defines an active tip for the targeted delivery of electrical signals, such as nerve stimulation signals and RF signals. One limitation of the prior art in introducer needles for catheters is that the needles' most distal bevel surface is not curved when viewed from the side of the bevel. One limitation of the prior art in injection adaptors for epidural catheters is that fluid cannot be injected into the injection adaptor when the stylet is inserted into the injection adaptor. One limitation of the prior art in injection adaptors for epidural catheters is that the injection adaptors do not include two fluid seals. One limitation of the prior art in injection adaptors for epidural catheters is that the adaptors do not include a first fluid seal for connection to a catheter and a second fluid seal to prevent outflow from the stylet port. One limitation of the prior art in injection adaptors for epidural catheters is that the adaptors do not contain three ports, one for the catheter, one for the stylet, and one for injection of fluids. One limitation in stylets for epidural catheters is that the stylet does not provide a port for injection into the catheter into which the stylet is placed.

U.S. Pat. No. 6,551,289 by A Higuchi and H Hyugaji presents an outer needle of an anesthetic needle assembly to be injected into an epidural area comprising a distal end formed with an annular cutting edge, wherein the distal end is gently curved, and the annular cutting edge has a forward half portion in the form of bifurcated convex surfaces over a plane including outer major and minor axes of said annular cutting edge, said annular cutting edge having an outer frontal corner part with a cutting angle that is larger than a crossing angle between said major axis and a longitudinal line of an outer surface of said outer needle in a plane including said major axis and perpendicular to said minor axis. One limitation of the needle in Higuchi is that it has a gentle curve at its distal end. One limitation of the needle in Higuchi is that the shaft is not substantially straight at the bevel.

NeuroCath epidural catheters and the Wavepoint epidural needles are sold by Neurotherm, Inc. of Wilmington, Mass. Related information is given in Neurotherm brochure "Epidural Product Line", brochure number SS 129 Rev.0, copyright 2011, Neurotherm, Inc., and is hereby incorporated by reference herein in its entirety. One limitation of the Wavepoint epidural needles is that they are not electrically insulated.

U.S. Pat. No. 2,716,983 by EF Windishchman et al presents a needle for the medical arts that includes a bevel at the needle's distal end wherein the bevel's distal surface is flat, the bevel's middle surface is flat, and the bevel's proximal surface can be either flat with a fillet between the middle and proximal surfaces, or curved.

U.S. Pat. No. 6,246,912 by M E Sluijter, W J Rittman, and E R Cosman presents in FIG. 9 a catheter electrode with one or more electrical contacts, where the catheter electrode is placed in the epidural space and applies high frequency signals via its electrical contacts. The electrical contact are tubular rings bonded to the substrate catheter and connected to wires internal to the catheter. The catheter may have reinforced metal spirals in its construction. One limitation of the art presented in U.S. Pat. No. 6,246,912 is that the catheter electrode does not provide for the injection of fluids. One limitation of the art presented in U.S. Pat. No. 6,246,912 is that the catheter electrode does not apply high frequency signals to the tissue by the same spring coil that is part of its shaft construction.

U.S. Pat. No. 8,075,556 by A Betts presents a specific construction of a device configured for placement in the spinal canal and delivery of RF energy. Betts describes a catheter delivery device to transmit radiofrequency energy to a spinal canal, comprising: a needle having an open proximal end and an open distal end, and a lumen that extends from the open proximal end to the open distal end; a catheter having a blunt, metallic tip on a distal end of the catheter that transmits a radio frequency energy to the treatment site, wherein the catheter is telescopically disposed within the needle lumen to allow the tip to be maneuverably positioned within the spinal canal; a catheter hub coupled to a proximal end of the catheter a metallic wire element telescopically disposed within a lumen of the catheter; and an adapter hub coupled to a proximal end of the wire element, wherein the adapter hub is cooperatively engageable to the catheter hub to form a single shaft, wherein a proximal end of the adapter hub is configured couple to a radio frequency generating device, and wherein the adapter hub and the catheter hub are sized and dimensioned relative to one another such that engagement of the adapter hub to the catheter hub allows a distal end of the wire element to touch a seating surface of the tip such that the wire element delivers a radio frequency energy from the radio frequency generating device to the tip. One limitation of the prior art in Betts is that the catheter has an adaptor hub. One limitation of the system described in Betts is that a standard epidural catheter is not used. One limitation of the system described in Betts is that construction of the catheter using a metal coil is not described. One limitation of the system described in Betts is that a safety strap within the catheter shaft is not described. One limitation of the absence of a metallic safety strap is that the impedance of the catheter shaft can distort and/or diminish electrical signals conducted along the shaft. One limitation of the system described in Betts is that RF is not delivered without seating of the RF wire in the inner surface of the distal end of the catheter. One limitation of the system described in Betts is that the system does not provide for temperature monitoring. One limitation of the system described in Betts is that the system does not provide for temperature-monitored RF therapy delivered through the catheter. One limitation of the system described in Betts is that the RF wire does include a temperature sensor. One limitation of the system described in Betts is that it is not a unitized injection electrode. One limitation of the system described in Betts is that the RF wire is separate from the catheter. One limitation of the system described in Betts is that injection through the catheter cannot be effected while the RF wire is in place within the catheter. One limitation of the system described in Betts is that it does not provide for simultaneous injection of fluids and delivery of electrical signals. One limitation of the prior art in Betts is that the needle is not covered by electrical insulation to define an active tip. Another limitation of the prior art in Betts is that the needle is not connected to an electrical energy source, such as a stimulator, or an RF generator. Another limitation of the prior art in Betts is that the introducer needle for a medical catheter electrode is not used as a path for return currents from the medical catheter electrode. One limitation of the prior art in Betts is that fluid cannot be injected through the catheter hub and into the catheter when the metallic wire element is telescopically disposed within a lumen of the catheter. One limitation of the catheter hub described in Betts is that it does not provide for simultaneous injection of fluids and delivery of electrical signals. One limitation of the catheter hub is does not describe more than one fluid clamp.

US patent application 2004/0210290 by Omar-Pasha describes a catheter electrode for pulsed RF treatment of nerves in the epidural space. One limitation of the prior art in Omar-Pasha is that it does not describe the use of a coil to construct the catheter electrode. Another limitation of the prior art in Omar-Pasha is it does not describe an RF electrode system in which an RF electrode stylet is inserted into a standard epidural catheter. One limitation of the prior art in Omar-Pasha is that the catheter electrode does not have a stylet port, nor a stylet port with a clamp. One limitation of the prior art in Omar-Pasha is that the catheter electrode does not have a separable injection adaptor.

The Pulsetrode electrode manufactured by BioAmpere Research SRL, Verona, Italy is a flexible electrode comprising a plastic shaft, three ring electrodes near its distal end, a hub, an injection port connected to a tube that is connected directly to the hub, a generator wire that connects directly to the hub, a moveable stylet is inserted into the injection port and travels along the shaft of the electrode. The Pulsetrode is configured for placement in the epidural space and delivery of radiofrequency fields to anatomy. Related information is given in Bioampere Research brochure "Pulsetrode" and is hereby incorporated by reference herein in its entirety. One limitation of the Pulsetrode is that it does not describe the use of a coil to construct the catheter electrode. One limitation of the Pulsetrode is that an active electrode tip of the catheter is constructed from the same coil that is included in the catheter shaft. Another limitation of the Pulsetrode is that it is not an RF electrode system in which an RF electrode stylet is inserted into a standard epidural catheter. Another limitation of the Pulsetrode is that the distal end of the electrode is electrically insulated. Another limitation of the Pulsetrode is that the active tip is not the sole active tip. One limitation of the Pulsetrode electrode is that the stylet must be removed from the electrode in order that injection take place. Another limitation of the pulsetrode electrode is that the stylet port is not capable of producing a fluid-tight seal around the stylet. Another limitation of the pulsetrode electrode is that the injection port is not separate from the stylet port. Another limitation of the pulsetrode electrode is that the injection port is not separable from the catheter.

Needles, catheters, and catheter guidewires are used in medicine for a variety of applications, including without limitation injecting of anesthetics, neurolytic agents, injection of medicine, and injection of radiographic contrast. Needles and catheters are used in medicine to inject and insert substances and devices in a variety of targets in the human body including muscles, nerves, organs, blood vessels, bone, connective tissue, body cavities, bodily spaces, bodily potential spaces, the urinary tract, reproductive tracts, and peri-neural spaces and potential spaces such as the epidural space.

The Cool-Tip Electrode of Radionics, Inc. and Valley Lab, Inc. is a 16-gauge (or 1.6 millimeter diameter) electrode with partially-insulated shaft and water-cooling channel inside its rigid, straight cannula shaft. The Cool-Tip electrode has an uninsulated active tip. The brochure from Radionics, document number 921-91-001 Rev. B, is hereby incorporated by reference in its entirety. The Cool-Tip Electrode is used for making large RF heat ablations of cancerous tumors, primarily in soft-tissue organs and bone. It has a closed trocar point that includes a metal plug that is welded to the metal tubing that is part of the electrode shaft. The distal end of the metal plug is sharpened to form a three sided, axially symmetric trocar. The distal end is a closed and sealed metal structure. The sharpened portion of the distal tip does not include the metal tubing itself, but rather the sharpened end of the metal plug that is welded to the metal tubing. The Cool-Tip electrode has the limitation that it does not provide a hollow tube for injection of fluids. The Cool-Tip electrode has the limitation that it is straight.

The present invention seeks to overcome the limitations and disadvantages of the prior art.

SUMMARY OF THE INVENTION

In one aspect, the present invention relates to a medical catheter system that includes an introducer needle, an injection adaptor hub, and a flexible catheter. In certain embodiments, the introducer needle includes electrical insulation that covers at least a portion of the needle's shaft. In certain embodiments, the catheter system includes an epidural needle, an injection adaptor hub, and an epidural catheter. In certain embodiments, the catheter can provide for the delivery of electrical signals, such as radiofrequency and nerve stimulation signals, to the living body. In certain embodiments, the epidural needle includes electrical insulation that covers at least a portion of the needle's shaft.

In one aspect, the present invention relates to a medical catheter system that includes an introducer needle and a flexible catheter that includes an injection port and that is configured for the injection of fluids into the living body. In certain embodiments, the introducer needle can include electrical insulation that covers at least a portion of the needle's shaft.

In one aspect, the present invention relates to methods for use of medical catheter systems. In certain embodiments, the present invention relates to methods of pain relief. In certain embodiments, the present invention relates to methods of epidural anesthesia. In one aspect, the present invention relates to the use of an electrode catheter to energize the introducer through which the electrode catheter is introduced into a living body.

In one aspect, the present invention relates to a medical electrode system that includes an introducer needle, an injection adaptor hub, a flexible catheter configured to delivery an electrical signal to a living body, an electrode configured to delivery an electrical signal to the catheter, and an electrical signal generator. In certain embodiments, the electrode includes a temperature measurement device and the electrical signal generator includes a temperature control circuit. In certain embodiments, the electrical signal includes an RF signal. In certain embodiments, the electrical signal includes a nerve stimulation signal. In certain embodiments, the injection adaptor hub is integral to the catheter. In certain embodiments, the electrode is integral to the catheter. In certain embodiments, the catheter is a unitized injection electrode catheter. In certain embodiments, the introducer needle can include electrical insulation that covers at least a portion of the needle's shaft.

In one aspect, the present invention relates to method for the use of medical, electrode catheter systems. In certain embodiments, the present invention relates to methods of electric field therapy. In certain embodiments, the present invention relates to electric field therapy applied to nerves in the epidural space. In certain embodiments, the present invention relates to methods of radiofrequency pain therapy. In certain embodiments, the present invention relates to methods of radiofrequency lesioning. In certain embodiments, the present invention relates to methods of cancer therapy.

In one aspect, the present invention relates to a system and method for an electrode system having a flexible shaft. In one aspect, the present invention relates to flexible radiofrequency electrode configured for placement in the epidural space. In one aspect, the present invention relates to a flexible electrode that provides for stimulation-guidance and the injection of fluids into the epidural space. In one aspect, the present invention relates to a flexible electrode that provides for nerve-stimulation-guidance of the catheter placement.

In one aspect, the present invention relates to the construction of catheter-style medical electrodes. In one aspect, the present invention relates to the use of a coil in the construction of a flexible electrode. In one aspect, the present invention relates to the use of a coil in the construction of a flexible, temperature-sensing, radiofrequency electrode. In one aspect, the present invention relates to a flexible injection electrode system that provides for injection of fluids and whose shaft includes a metal coil that is covered over at least a part of its length by electrical insulation, that is uncovered over at least a part of its length for the application of electrical signals to tissue.

In one aspect, the present invention relates to a catheter electrode system that is "unitized" wherein a flexible catheter electrode includes an injection port, a generator connection, and a temperature sensor. In one aspect, the present invention relates to a one-piece, flexible electrode wherein the electrode's shaft is constructed using a spring coil whose proximal end is covered by an electrically-insulated sheath, and whose distal end is closed by a weld that incorporates the spring coil, an RF wire, a thermocouple wire, and an internal structuring wire, such as a safety strap or movable stylet. In one aspect, the present invention relates to a one-piece, flexible electrode wherein the electrode's shaft is constructed using a spring coil whose proximal end is covered by an electrically-insulated sheath, and whose distal end includes an opening and a weld that incorporates the spring coil, an RF wire, a thermocouple wires, and an internal structuring wire, such as a safety strap or moveable stylet.

In one aspect, the present invention relates to a catheter electrode system that includes a catheter with metallic active tip and a temperature-sensing electrode configured to be positioned within an inner lumen of the catheter and to energize the catheter's active tip; One advantage of this aspect is that the electrode can both deliver electrical signals to a catheter tip, monitor the temperature at the catheter tip, and provide variable stiffening of the catheter shaft and tip.

In one aspect, the present invention relates to an injection adaptor hub for a medical catheter.

In one aspect, the present invention relates to an injection adaptor hub that includes a first clamp configured to create a watertight seal between the injection adaptor hub and a catheter, a second clamp configured to create a watertight seal between the injection adaptor hub and the catheter's stylet, and an injection port configured to conduct fluid into the catheter. In certain embodiments, the first clamp and the second clamp are tuohy-borst style clamps.

In one aspect, the present invention relates to an injection adaptor hub that includes a first clamp configured to create a watertight seal between the injection adaptor hub and a catheter, a second clamp configured to create a watertight seal between the injection adaptor hub and an electrode, and an injection port configured to conduct fluid into the catheter, wherein the electrode is configured to deliver electrical signals through a portion of the catheter to a living body. In certain embodiments, the electrode can be a temperature-sensing RF electrode. In certain embodiments, the first clamp and the second clamp are tuohy-borst style clamps.

In one aspect, the present invention relates to an injection adaptor hub and an injection stylet, wherein the injection adaptor hub includes a first clamp configured to create a watertight seal between the injection adaptor hub and a catheter, a second clamp configured to create a watertight seal between the injection adaptor hub and the catheter's stylet, and wherein the injection stylet includes an injection port configured to conduct fluid into the catheter and an elongated shaft configured to reside in an inner lumen of the catheter. In certain embodiments, the first clamp and the second clamp are tuohy-borst style clamps.

In one aspect, the present invention relates to an injection adaptor hub and an injection electrode, wherein the injection adaptor hub includes a first clamp configured to create a watertight seal between the injection adaptor hub and a catheter, a second clamp configured to create a watertight seal between the injection adaptor hub and the injection electrode, and wherein the injection stylet includes an injection port configured to conduct fluid into the catheter, an elongated shaft configured to reside in an inner lumen of the catheter, and a conductive element configured to deliver electrical signals through a portion of the catheter to a living body. In certain embodiments, the injection electrode can be a temperature-sensing RF electrode.

In one aspect, the present invention relates to a method of injection through a medical catheter by means of an injection hub while the catheter's stylet is positioned within an inner lumen of the catheter. In one aspect, the present invention relates to a method of injection through a medical catheter by means of an injection hub while an electrode is positioned within an inner lumen of the catheter.

In one aspect, the present invention relates to a needle that is configured both for the introduction of a catheter into a living body, and the delivery of electrical signals through a part of the needle's shaft.

In one aspect, the present invention relates to a medical needle bevel that is configured for placement in the epidural space of the human body. In one aspect, the present invention relates to a needle bevel that is configured for the introduction of a flexible catheter into the living body. In one aspect, the present invention relates to a needle bevel that is configured for the introduction of an epidural catheter into the living body. In one aspect, the present invention relates to a needle bevel that is configured both to penetrate solid tissue and to minimize damage to a flexible catheter passing through the bevel. In one aspect, the present invention relates to a needle bevel that includes at least two surfaces, wherein the most distal surface is a curved surface. In one aspect, the present invention relates to a needle bevel that includes at least two surfaces, wherein the most distal surface is a curved surface, the heel of the bevel is smoothed to reduce cutting edges, and the inner edges of the bevel are smoothed to reduce cutting edges. In one aspect, the present invention relates to a needle system that includes a cannula and a stylet, wherein the cannula's bevel includes at least two surfaces, wherein the most distal surface is a curved surface, and wherein the stylet engages with the cannula such that the combined bevel is substantially a flat, angled bevel.

In one aspect, the present invention relates to a needle that includes a hollow shaft, a bevel that is configured for the introduction of a flexible catheter into the living body, and electrical insulation covering a part of the needle's shaft. In one aspect, the present invention relates to a needle that includes a tubular metal shaft, a bevel that is configured for the introduction of a flexible catheter into the living body, and electrical insulation covering a part of the needle's shaft. In one aspect, the present invention relates to a needle that includes a tubular metal shaft, a bevel that is configured for the introduction of a flexible catheter into the living body, and electrical insulation covering the proximal end of the needle's shaft. In one aspect, the present invention relates to a needle that includes a tubular metal shaft, a bevel that is configured for the introduction of a flexible catheter into the living body, and electrical insulation covering to the proximal end of the needle's shaft and fixedly attached to the needle's shaft. In one aspect, the present invention relates to a needle that includes a tubular metal shaft, a bevel that includes a rounded proximal heel and a rounded inner edge, and electrical insulation covering the proximal end of the needle's shaft and fixedly attached to the needle's shaft.

In one aspect, the present invention relates to a needle that includes a hollow shaft, an epidural bevel, and electrical insulation covering a part of needle's shaft. In one aspect, the present invention relates to a needle that includes a hollow shaft, an epidural bevel, and electrical insulation covering the proximal end of the needle's shaft, leaving the distal end of the needle's shaft electrically-uninsulated. In one aspect, the present invention relates to a needle system for the medical arts that includes a needle and a stylet, wherein the needle includes a hollow shaft, an epidural bevel, and electrical insulation covering a part of the needle shaft, and wherein the stylet is an elongated structure that can be positioned in the inner lumen of the needle.

In one aspect, the present invention relates to an RF cannula that includes an epidural bevel. In one aspect, the present invention relates to an RF cannula that includes a bevel that is configured for percutaneous placement in the epidural space and for introduction of an epidural catheter into the epidural space. In one aspect, the present invention relates to an RF cannula that is configured to penetrate solid tissue and to minimize the likelihood of damage of a catheter passing through the cannula's inner lumen. In one aspect, the present invention relates to an RF cannula wherein the edges of the cannula's bevel heel is rounded to reduce sharp edges and wherein the inner edge of the cannula's bevel are rounded to reduce sharp edges. In one aspect, the present invention relates to an RF cannula that is configured for epidural anesthesia.

In one aspect, the present invention relates to a needle that is configured for both epidural anesthesia and radiofrequency lesioning.

In one aspect, the present invention relates to an RF cannula that includes a bevel configured for placement in the epidural space. In one aspect, the present invention relates to an RF cannula that includes a bevel configured for placement in the epidural space, and a physically-separate RF electrode configured to electrify the RF cannula. In one aspect, the present invention relates to an RF electrode that includes a bevel configured for placement in the epidural space.

In one aspect, the present invention relates to a method of introducing an RF cannula into the living body and energizing the RF cannula using an electrode catheter. In one aspect, the present invention relates to a method of introducing an RF cannula into the living body, energizing the RF cannula using an electrode catheter, and advancing the electrode catheter beyond the RF cannula into the living body and energizing the electrode catheter. In one aspect, the present invention relates to a method of introducing an RF cannula into the epidural space and energizing the RF cannula using an electrode catheter.

In one aspect, the present invention relates to a method of introducing an RF cannula into the epidural space and energizing the RF cannula using an RF electrode. In one aspect, the present invention relates to a method of introducing an RF cannula into the epidural space via the sacral hiatus and energizing the RF cannula using an RF electrode. In one aspect, the present invention relates to a method of introducing an RF electrode into the epidural space and performing an RF pain management procedure.

In one aspect, the present invention relates to a needle that includes a bevel configured for introducing a catheter, a hollow shaft that is covered by electrical insulation to define a conductive active tip configured to deliver electrical signals to tissue, and a connection configured to conduct an electrical signal to the active tip. In one aspect, the present invention relates to an RF cannula that includes an epidural bevel configured for introducing an epidural catheter, a shaft that is partially insulated to define an active tip configured to conduct electrical signals to tissue in contact with the tip, and a wire configured to conduct an RF signal to the active tip. In one aspect, the present invention relates to an RF cannula that includes an epidural bevel configured for introducing an epidural catheter, a shaft that is partially insulated to define both an active tip configured to conduct electrical signals to tissue in contact with the active tip, and an conductive connection point configured to conduct electrical signal to the active tip.

In one aspect, the present invention relates to a method wherein an RF cannula is connected to the reference jack of an RF generator, an electrode catheter is connected to the RF output of the RF generator, the needle is placed in the living body, the electrode catheter is inserted into the living body through the needle, and RF current flows from the active tip of the needle to the active tip of the electrode catheter.

DESCRIPTION OF THE DRAWINGS

Like reference symbols in the various drawings indicate like elements.

Figure 4A:
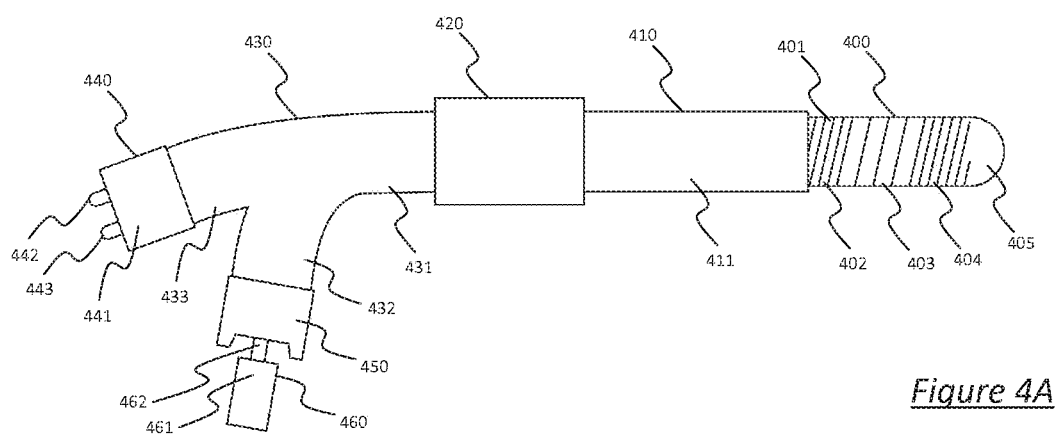
FIG. 4A is a schematic diagram showing connector in an external view a unitized injection electrode with a flexible active tip, a flexible shaft depicted in a straight position, an injection port, a generator connector, and a moveable stylet.
Figure 4B:
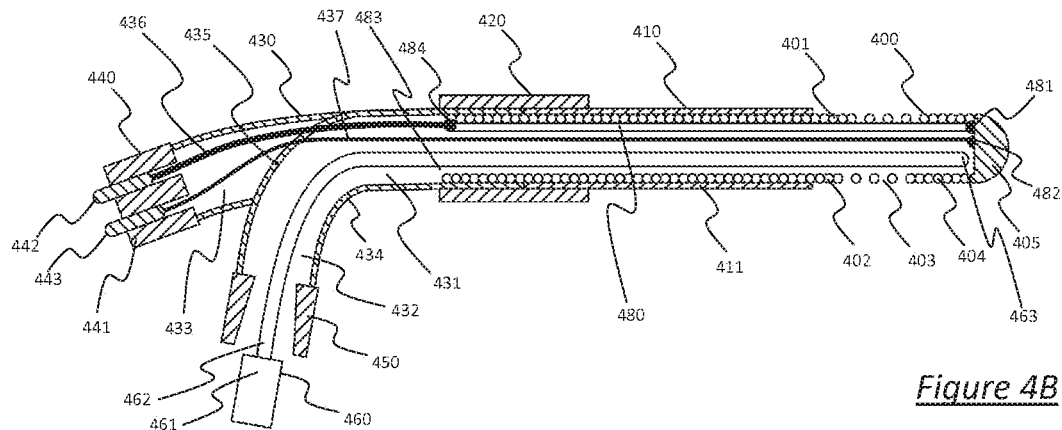
FIG. 4B is a schematic diagram showing in a sectional view a moveable stylet positioned inside a unitized injection electrode where a coil is used in the construction of the shaft and active tip, where the electrode has a temperature sensor, injection port, and a generator connector.

A reference to a figure by its numeric index alone is a reference to all figures having that numeric index as their prefix; for example, "FIG. 4" refers to FIG. 4A and FIG. 4B collectively.

DETAILED DESCRIPTION

Referring to FIGS. 1A, 1B, 1C, and 1D, FIG. 1 present several embodiments of a medical catheter system, in accordance with the present invention, wherein the medical catheter system includes an injection catheter system 160, an introducer needle 170, and an electrical power supply 180, wherein the catheter system 160 and introducer needle 170 are configured for placement in the human body. Catheter system 160 includes a connection 140 to power supply 180, an injection port 150, a hub 120, a shaft 110 with a distal end and a proximal end, and a tip 100. The hub 120 can be at the proximal end of the catheter shaft 110. The tip 100 can be at the distal end of the shaft 110. The needle 170 can include a hub 171 at its proximal end, a shaft 172, electrical insulation 173 covering the shaft 172, and an electrically-conductive distal tip 174. In certain embodiments, the needle hub 171 includes an injection port, such as a female luer port. The tip 100 can include a temperature sensor. The catheter 160 can include multiple temperature sensors, in certain embodiments. The needle can penetrate the living body 190. The needle 170 can include a shaft 172 that is constructed from a metal tube. The bevel at the distal end 174 of the needle's shaft 172 can be an epidural needle bevel, such as a touhy bevel. In certain embodiments, the needle has features both of an RF cannula and an epidural needle. The catheter tip 100 and shaft 110 can pass through an inner lumen of the needle 170 into the living body 190, such as the human body. The living body can includes a brain 191, a spinal cord 192, and peripheral nerves 193. In certain embodiments, the needle's distal tip 174 can be percutaneously positioned in the epidural space of the living body 190, the catheter shaft 110 can be introduced into the epidural space of the living body 190, and the tip 100 of the catheter 160 can be positioned nearby a nerve 193 in the epidural space. In one example, electrode 160 enters the epidural space via a median or paramedian approach. In one example, electrode 160 enters the epidural space via the sacral hiatus. In one example, electrode 160 enters the epidural space via an intervertebral foramina of the spinal column. In one example, the active tip 100 of the electrode 160 is positioned near a dorsal spinal nerve root. In one example, the active tip 100 of the electrode 160 is positioned near a dorsal root ganglion (DRG). In one example, the active tip 100 of the electrode 160 is positioned near a spinal nerve. The catheter 160 can be an electrode catheter. The shaft 110 can include electrically insulation surrounding an electrical conductor, and the active tip 100 can be electrically conductive, so that electrical signals delivered to connector 140 is conducted through generator cable 133, tube 131, hub 120, shaft 110, active tip 100, and to tissue 190 in contact with the active tip 100, but not to tissue in contact with the shaft 110 of the catheter 160. A syringe 159 can be connected to port 150 and fluid injected into port 150 is conducted through tubing 131, hub 120, shaft 110, and out from holes that can be positioned along the shaft 110, the tip 100, or the distal end of the tip 100. In certain embodiments, port 150 is a luer port, such as a female luer port. The generator 180 can include a first output pole 186 and a second output pole 185. The generator 180 can produce an electrical potential between output pole 185 and output pole 186. In certain embodiments, generator 180 can produce a radiofrequency signal. In certain embodiments, generator 180 can produce a pulsed radiofrequency signal. In certain embodiments, generator 180 can produce a nerve stimulation signal. In certain embodiments, the generator 180 can produce a PENS signal. In certain embodiments, the generator 180 can produce a TENS signal. In certain embodiments, the generator 180 can produce a muscle stimulation signal. In certain embodiments, the generator 180 can be a medical RF generator. In certain embodiments, generator 180 can produce a continuous radiofrequency signal. In certain embodiments, generator 180 can produce a pulsed radiofrequency signal. In certain embodiments, the generator 180 can be a direct current generator. In certain embodiments, the generator 180 can produce a neuromodulation signal. In certain embodiments, generator 180 can produce a high frequency electrical signal. In certain embodiments, generator 180 can include additional output poles and can impose an electrical potential on each pole and can impose a high-impedance pathway between any pair of output poles. In certain embodiments, the generator 180 can include temperature-measurement circuitry. In certain embodiments, the generator 180 can control its output level in response to a temperature signal measured by the catheter 160. In certain embodiments, the generator 180 can control the temperature measured at tip 100 by amplitude modulation of an RF signal output. The generator 180 can produce a voltage, current, or power output level. In certain embodiments, the catheter system can be used to apply pulsed radiofrequency fields to nerves in the epidural space, such as a dorsal nerve root or a doral root ganglion, of the living body 190, for example, for the treatment of neuropathic pain. In certain embodiments, the system can be used to produce heat lesions in the living body, for example, heat lesions of nerve roots in the epidural space for the purpose of controlling pain in a patient suffering from terminal cancer. One advantage of the method of RF heat lesioning of nerve roots is that it provides for the treatment of cancer pain without greater control of targetry than does injection of fluid neurolytic agents. In certain embodiments, the active tip 100 of the electrode can be at the distal end of the catheter 160. In certain embodiments, the active tip 100 of the electrode 160 can have electrical insulation distal to the active tip 100 along the shaft 110. In certain embodiments, the electrode 100 can have multiple active tips that can be connect to generator 180 output potentials via a switching system. In certain embodiments, the needle 170 can be energized by a standard RF electrode, such as one with a shaft constructed from a stainless steel hypotube and including a thermocouple temperature sensor. In certain embodiments, the needle 170 can include a curve in its shaft 172. In certain embodiments, the needle 170 can have a bend at the active tip 174 of the cannula 170. In certain embodiments, the needle 170 can have a bend in its shaft 172 such that when the catheter 160 is positioned inside the cannula 170, at the distal end 100 of the catheter 160 is aligned with the distal end of the cannula shaft 174, the active tip 100 of the catheter 160 is positioned at the location of a bend in the shaft 172 of the cannula 170. One advantage of a curve in the shaft 172 is that when the active tip 100 is positioned within the shaft 172 near the location of the curve, the active 100 is more likely to make contact with the inner lumen of the shaft 172 and thereby more reliably conduct electrical signals from the active tip 100 to the shaft 172. In certain embodiments, needle 170 can be tissue-piercing. In some embodiments, the electrode shaft 110 includes a feature that provides for enhanced visualization of the shaft 110 using ultrasound imaging. In some embodiments, the active tip 100 includes a feature that provides for enhanced visualization of the tip 100 using ultrasound imaging.

Figure 1A:
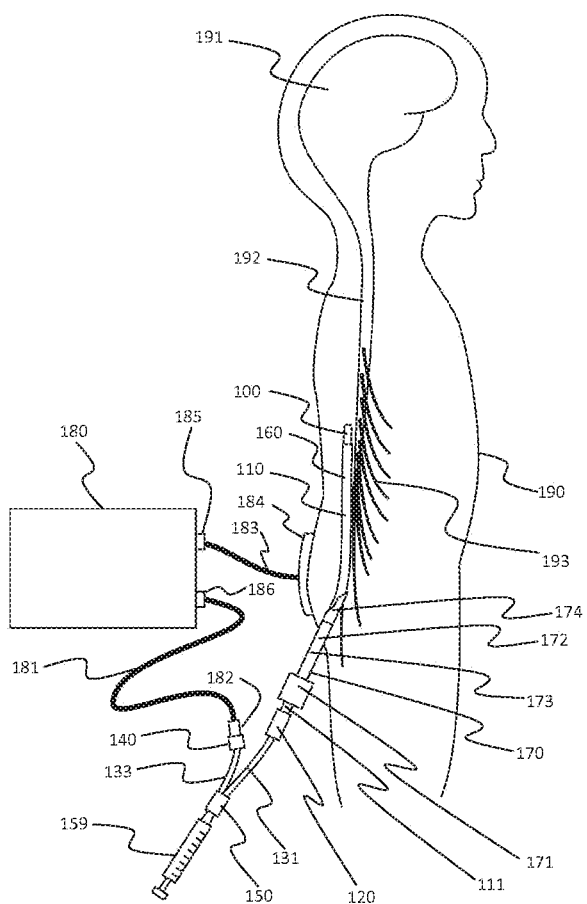
FIG. 1A is a schematic diagram showing a catheter system including an injection catheter electrode, an epidural RF cannula, an electrical generator, and a ground pad, wherein the cannula is placed in the epidural space of living body, the catheter is advanced beyond the cannula into the epidural space, and the catheter is energized by the generator in a monopolar manner, where a ground pad carries return currents from the catheter through the living body.
Figure 1B:
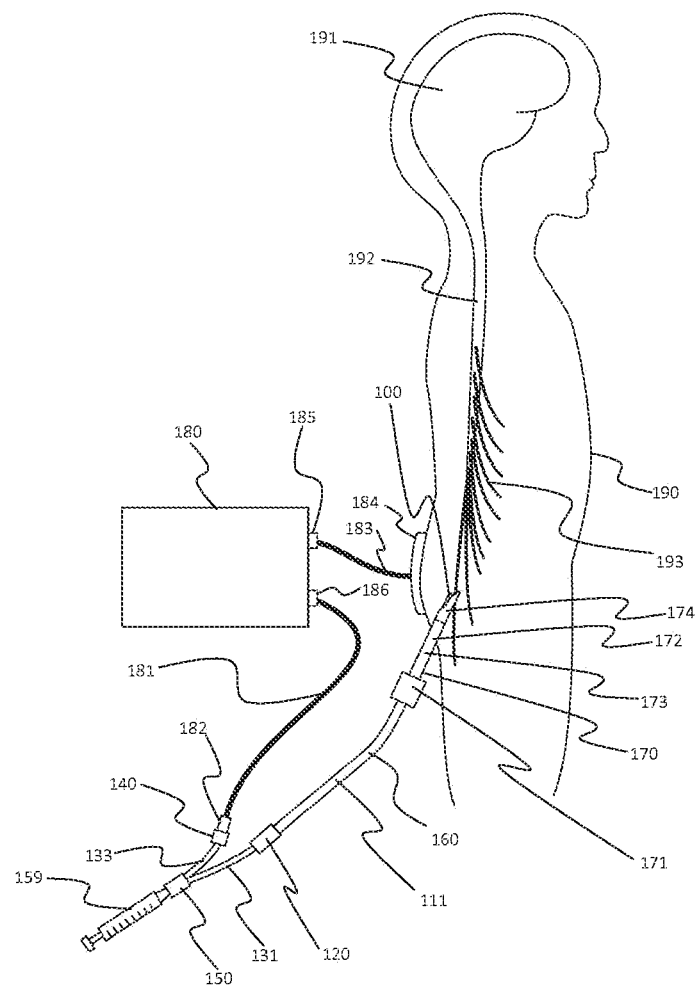
FIG. 1B is a schematic diagram showing a catheter system including an injection catheter electrode, an epidural RF cannula, an electrical generator, and a ground pad, wherein the cannula is placed in the epidural space of a living body, the conductive active tip of the catheter is positioned such that it conducts electrical signals the cannula, and the catheter and cannula are both energized by the generator in a monopolar manner, where a ground pad carries return currents from the catheter and cannula through the living body.

Referring now to FIG. 1A and FIG. 1B, several embodiments of a medical catheter system are presented. Cable 181 includes connector 182, connector 182 is attached to catheter connector 140, and cable 181 conducts the signal output from generator jack 186 to the catheter 160. Cable 183 is attached to ground pad 184, ground pad 184 is placed on the surface of body 190, and cable 183 conducts electrical signals from generator jack 185 to the ground pad 184. In one example, pole 185 can be the reference jack of generator 180. The shaft 110 of catheter 160 passes through the inner lumen of needle 170. Element 111 is the portion of catheter shaft 110 that is proximal to the needle 170. When generator 180 produces and electrical output, current passes between the electrode active tip 100 and the reference ground pad 184; this configuration can be referred to as a "monopolar" configuration.

Referring to FIG. 1A specifically, the catheter is advanced into the living body such that the entirely of the active tip 100 extends beyond the distal end of the needle 170. In this configuration, the needle is electrically insulated from electrical signals applied to the catheter 160 by means of the electrical insulation covering the shaft 110. In this configuration, electrical signals from the generator 180 are applied to the tissue through the active tip 100 of the catheter, and not through the needle 170.

Referring to FIG. 1B specifically, the catheter 160 is positioned within the needle 170 such that the active tip 100 of the catheter 160 contacts a portion of the conductive inner lumen of the needle 170. In this configuration, electrical signals applied to the catheter 160 are applied to tissue in contact with the conductive active tip 174 of the needle 170. In one example, the catheter 160 is positioned such that the tip 100 is within the tip 174 of the needle; one advantage of this positioning is that it provides for temperature-controlled RF lesioning of tissue in contact with the active tip 174 of the needle. In another example, a part of the active tip 100 of the electrode 160 can protrude from the distal end of the needle 170; one advantage of this configuration is that the protruding portion of tip 100 and the tip 174 form a combined, enlarged active tip.

In certain embodiments, a monopolar method of electric field therapy includes the steps of (1m) inserting into a living body 190 a cannula 170 that includes a tip bevel configured to prevent damage to a catheter 160 passing through the tip bevel opening 174, (2m) inserting an electrode catheter 160 through the needle 170, (3m) applying a reference electrode 184, such as a ground pad or an indifferent electrode, to the living body 190, and (4m) applying an electric signal between the active tip 100 of the electrode 160 and the reference electrode 184. In certain embodiments, the electric signal in the said monpolar method of electric field therapy can include a radiofrequency signal. In certain embodiments, the electric signal in the said monpolar method of electric field therapy can include a nerve stimulation signal. In certain embodiments, the electric signal in the In certain embodiments, the said monpolar method of electric field therapy can include the step of (5m) positioning the active tip 100 of the catheter 160 within the needle 170 such that the electrical signal is applied to the living body 190 through the active tip 174 of the needle 170. In certain embodiments, the said monpolar method of electric field therapy can include the step of (6m) positioning the active tip 100 of the catheter 160 beyond the needle 170 such that the electrical signal is applied to the living body 190 through the active tip 100 of the electrode 160. In certain embodiments, the said monpolar method can include the step (6m) of injecting a fluid agent, such as a radiographic contrast agent, an anesthetic fluid, a fluid configured for lysis of epidural adhesion, a neurolytic agent, or an alcohol into the living body via the catheter 160 or the needle 170. In certain embodiments, the said monpolar method includes steps (1m), (2m), (3m), (4m), (5m), and (6m) of the said monpolar method. In certain embodiments, the said monpolar method can include the step of introducing the needle 170 and catheter 160 into the epidural space of the living body 190. In certain embodiments, step (4m) includes adjustment of the electric signal to control a temperature measured by catheter 160. In certain embodiments, the electric signal in step (4m), such as a nerve stimulation signal, can be used strictly for the purpose of positioning active tip 100 or active tip 174, rather than for a therapeutic purpose per se. One advantage of the said monopolar method of electric field therapy is that electrical field therapy can be applied to nerve adjacent to the active tip 174 of the cannula 170 and to a nerve at another location at which the active tip 100 of the catheter 100 can be positioned.

Figure 1C:
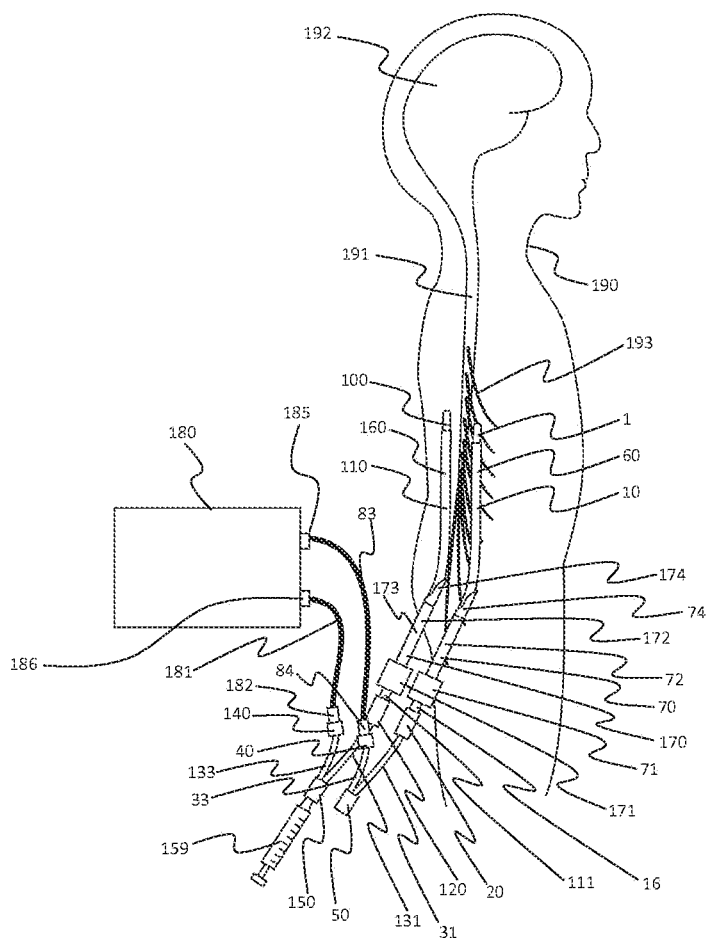
FIG. 1C is a schematic diagram showing a catheter system including two injection catheter electrodes, two epidural RF cannulae, and an electrical generator, wherein the cannulae are placed in the epidural space of a living body, each catheter is introduced into the epidural space through one of the cannulae, and the generator energizes the catheters in a bipolar manner.

Referring to FIG. 1C, the catheter system includes a second needle 70 and injection electrode catheter 60. In certain embodiments, the needle 70 can have an embodiment that can be taken by the needle 170. In certain embodiments, the catheter 60 can have an embodiment that can be taken by catheter 160. Catheter system 60 includes a connection 40 to the power supply 180, an injection port 50, a hub 20, a shaft 10 with a distal end and a proximal end, and a tip 1. The hub 20 can be at the proximal end of the catheter shaft 10. The tip 1 can be at the distal end of the shaft 10. The needle 70 can include a hub 71 at its proximal end, a shaft 72, electrical insulation 73 covering the shaft 72, and an electrically-conductive distal tip 74. The tip 1 can include a temperature sensor. The needle can penetrate the living body 190. The needle 70 can include a shaft 72 that is constructed from a metal tube. The bevel at the distal end 74 of the needle's shaft 72 can be an epidural needle bevel, such as a touhy bevel. The catheter tip 1 and shaft 10 can pass through an inner lumen of the needle 70 into the living body 90, such as the human body. A syringe 159 can be attached to port 50 and thereby fluid an be injection through the catheter 60 into the living body. Output pole 185 can be connected to catheter connector 50 by means of cable 83 and cable connector 84 and thereby the electrical potential of jack 185 is applied to active tip 1 of catheter 60. When an electrical output, such a nerve stimulation output or radiofrequency output is applied between jacks 185 and 186, electrical current flows through the living body between active tip 100 of catheter 160 and active tip 1 of catheter 60; this configuration can be referred to as a "bipolar" configuration. One advantage of a bipolar configuration that includes two catheter electrodes is that electric field therapy can be applied without the use of a reference or ground pad or indifferent electrode. One advantage of the bipolar configuration that includes two catheter electrodes is that the electric field can be focused between the active tips 1 and 100 of the catheter electrodes 60 and 160. In some configurations, one or both of the electrodes 60 and 160 can be positioned within the electrode's respective needle 70 or 170, and the active tip 74 or 174 can be energized by the generator 180.

In certain embodiments, a bipolar method of electric field therapy includes the steps of (1b) inserting into a living body 190 a first cannula 170 that includes a tip bevel configured to prevent damage to a catheter 160 passing through the tip bevel opening 174, (2b) inserting a first electrode catheter 160 through the first needle 170, (3b) inserting into a living body 190 a second cannula 70 that includes a tip bevel configured to prevent damage to a catheter 60 passing through the tip bevel opening 74, (4b) inserting a second electrode catheter 60 through the first needle 70, (5b) applying an electric signal between the first catheter 160 and the second catheter 60. In certain embodiments, the electric signal in the said bipolar method of electric field therapy can include a radiofrequency signal. In certain embodiments, the electric signal in the said bipolar method of electric field therapy can include a nerve stimulation signal. In certain embodiments, the said bipolar method of electric field therapy can include the step of (6b) positioning the active tip 100 of the catheter 160 within the needle 170 such that the electrical signal is applied to the living body 190 through the active tip 174 of the needle 170. In certain embodiments, the said bipolar method of electric field therapy can include the step of (7b) positioning the active tip 1 of the catheter 60 within the needle 70 such that the electrical signal is applied to the living body 190 through the active tip 74 of the needle 70. In certain embodiments, the said bipolar method of electric field therapy can include the step of (8b) positioning the active tip 100 of the catheter 160 beyond the needle 170 such that the electrical signal is applied to the living body 190 through the active tip 100 of the electrode 160. In certain embodiments, the said bipolar method of electric field therapy can include the step of (9b) positioning the active tip 1 of the catheter 60 beyond the needle 70 such that the electrical signal is applied to the living body 190 through the active tip 1 of the electrode 60. In certain embodiments, the said bipolar method can include the step (10b) of injecting a fluid agent, such as a radiographic contrast agent, an anesthetic fluid, a fluid configured for lysis of epidural adhesion, a neurolytic agent, or an alcohol via the catheter 160 or the needle 170. In certain embodiments, the said bipolar method can include the step (11b) of injecting a fluid agent, such as a radiographic contrast agent, an anesthetic fluid, a fluid configured for lysis of epidural adhesion, a neurolytic agent, or an alcohol via the catheter 60 or the needle 70. In certain embodiments, the said bipolar method includes steps (1b), (2b), (3b), (4b), (5b), (6b), (7b), (8b), (9b), (10b), and (11b). In certain embodiments, the said biplar method can include the step of introducing the needle 170 and catheter 160 into the epidural space of the living body 190. In certain embodiments, the said biplar method can include the step of introducing the needle 70 and catheter 60 into the epidural space of the living body 190. In certain embodiments, the said bipolar method can include the step of introducing the needles 70 and 170 and catheters 60 and 160 into the epidural space of the living body 190. In certain embodiments, step (5b) includes adjustment of the electric signal to control a temperature measured by either catheter 160 or catheter 60. In certain embodiments, a method of electric field therapy can include steps from both the said monopolar method of electric field therapy and the said bipolar method of electric field therapy. In certain embodiments, the electric signal in step (5b), such as a nerve stimulation signal, can be used strictly for the purpose of positioning active tip 100, active tip 174, active tip 1, or active tip 74, rather than for a therapeutic purpose per se.

Figure 1D:
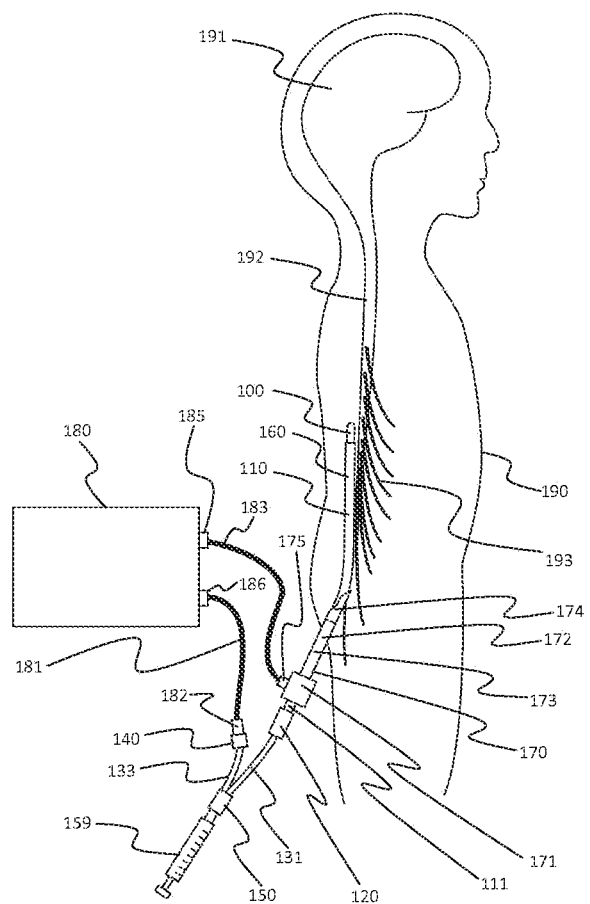
FIG. 1D is a schematic diagram showing a catheter system including an injection catheter electrode, an epidural RF cannula including a generator connection, an electrical generator, wherein the cannula is placed in the epidural space of living body, the catheter is advanced beyond the cannula into the epidural space, and the catheter and cannula are energized by the generator such that the catheter and cannula carry return currents from each other through the living body.

Referring to FIG. 1D, the catheter system omits a ground pad and includes a connection 175 between the output pole 185 of the generator 180 to the cannula 170. In certain embodiments, the connection 175 is an alligator clip attached to an element of the needle 170, such as a uninsulated portion of the shaft outside the living body 190, that is in electrical communication with the active tip 174 of the cannula 170. In certain embodiments, the connection 175 is a cable connected to the conductive shaft 172 of the needle 170. In certain embodiments, the connection 175 is included in the hub 171 of the cannula 170. The active tip 100 of the electrode 160 is advance beyond the distal end of the needle 170 such that the tip 100 is not in direct contact with the needle 170. The electrical insulation on shaft 110 of the catheter 160 prevents direct flow of electrical current between the needle 170 and the catheter 160. In this configuration, an electrical signal applied between jacks 186 and 185 generates electrical current between the active tip 100 of catheter 160 and the active tip 174 of needle 170. In certain embodiments, the needle 170 can be one of the embodiments presented in FIG. 13 and FIG. 14. One advantage of the system presented in FIG. 1D is that electric field therapy, such as pulsed RF field therapy, can be applied by means of a catheter electrode 160 without with use of a ground pad. One advantage of the system presented in FIG. 1D is that electric field therapy, such as pulsed RF field therapy, can be applied to structures adjacent to the active tip 174 of the needle 170 and structures adjacent to the active tip 100 of the catheter 160 at the same time.

In certain embodiments, an electrode-needle method of electric field therapy includes the steps of (1e) inserting into a living body 190 a cannula 170 that includes a tip bevel configured to prevent damage to a catheter 160 passing through the tip bevel opening 174, (2e) inserting an electrode catheter 160 through the needle 170 such that the active tip 100 of the electrode 160 is not in contact with the needle 170, and (3e) applying an electric signal between the electrode 160 and needle 170. In certain embodiments of step (3e) electric current flows between the active tip 100 of the catheter 160 and the active tip 174 of the needle 170. In certain embodiments, the electric signal in the said electrode-needle method of electric field therapy can include a radiofrequency signal. In certain embodiments, the electric signal in the said electrode-needled method of electric field therapy can include a nerve stimulation signal. In certain embodiments, the said electrode-needle method of electric field therapy can include the step (4e) of injecting a fluid agent, such as a radiographic contrast agent, an anesthetic fluid, a fluid configured for lysis of epidural adhesion, a neurolytic agent, or an alcohol into the living body via the catheter 160 or the needle 170. In certain embodiments, the said electrode-needle method includes steps (1e), (2e), (3e), and (4e) of the said electrode-needle method. In certain embodiments, the said electrode-needle method can include the step of introducing the needle 170 and catheter 160 into the epidural space of the living body 190. In certain embodiments, step (3m) includes adjustment of the electric signal to control a temperature measured by catheter 160. In certain embodiments, the electric signal in step (3e), such as a nerve stimulation signal, can be used strictly for the purpose of positioning active tip 100 or active tip 174, rather than for a therapeutic purpose per se. In certain embodiments, embodiments of catheter systems presented in FIG. 1 can be energized in mixed monopolar-bipolar configurations wherein multiple catheters and ground pads are simultaneously energized.

Referring to FIG. 1 generally, in certain embodiments, catheter 160 can have a different construction from that presented in FIG. 1. In certain embodiments, catheter system 160 can be a flexible injection electrode. In certain embodiments, catheter system 160 can include a catheter that is energized by a physically-separate electrode, for example, by placing the electrode into an inner lumen of the catheter. In certain embodiments, catheter system 160 can include a catheter shaft 110 that is separable from the injection hub 120. In certain embodiments, the catheter shaft 110 can include a metal coil spring. In certain embodiments, the tip 100 can be an uninsulated metallic coil, such as a round-wire spring coil, a flat-wire spring coil, a spiral cut metal tube, a laser-cut metal tube. In certain embodiments, the tip 100 can be stainless steel. In certain embodiments, the shaft 110 and tip 100 can include the same coil. In certain embodiments, the outer surface of shaft 110 can be electrically conductive and in electrically communication with the active tip 100. In certain embodiments, catheter system 160 can be one of the embodiments presented in FIGS. 1, 2, 3, 4, 5, 6, 7, 8, 9, 10, and 11. In certain embodiments, needle 170 can be an epidural needle, for example a needle with a tuohy bevel. In certain embodiments, the needle 170 can be a spinal needle. In certain embodiments, needle 170 can be one of the embodiments presented in FIGS. 12, 13, and 14. In certain embodiments, the needle 170 has a removable stylet that is used to make the needle substantially solid during insertion, and removed to allow for passage of fluids and devices into the body through the inner lumen of the needle 170. In certain embodiments, needle 170 can omit electrical insulation 173. In certain embodiments, hub 120 can be an injection adaptor hub for a catheter. In certain embodiments, the catheter 160 can be a non-electrode catheter.

In certain embodiments, the systems and methods presented in FIG. 1 can provide for stimulation-guided epidural anesthesia and temperature-monitored radiofrequency treatment, including pulsed radiofrequency treatment, of nerves. In certain embodiments, the systems and methods presented in FIG. 1 can provide for the application of high frequency electric fields to nerve by means of placing an electrode via the epidural space. In certain embodiments, the systems and methods presented in FIG. 1 can provide for the application of high-frequency electric fields to nerve by means of placing an electrode within the neural foramina. In certain embodiments, the systems and methods presented in FIG. 1 can provide for cost-effective manufacturing of a catheter electrode configured for placement in the epidural space. In certain embodiments, the systems and methods presented in FIG. 1 can provide for cost-effective manufacturing of a temperature-monitoring catheter electrode configured for placement in the epidural space. In certain embodiments, the systems and methods presented in FIG. 1 can provide for the construction of a catheter electrode capable of delivery of nerve stimulation signals, delivery of radiofrequency signals, and fluid injection for medical procedures, such as pain management. In certain embodiments of the system and methods presented in FIG. 1, the nerve stimulation signals produced by generator 180 can be used to position the electrode 160 for the purpose of an epidural anesthesia procedure, such as lysis of adhesions, chemical epidural neurolysis, epidural injection of alcohol, and epidural injection of phenol. In certain embodiments of the system and methods presented in FIG. 1, the electrode 160 can provide for the injection of fluids, such as radiocontrast agents, anesthetics, neurolytics agents, alcohol, phenol, saline, hyaluronidase, local anesthetic, corticosteroids, hypertonic saline. In certain embodiments of the system and methods presented in FIG. 1, the electrode tip 100 and shaft 110 can be visible in x-ray images, such as fluoroscopy; one advantage of these embodiments is that radiographic imaging can be used to position the electrode 160 in the human body 190. In certain embodiments, the systems and methods presented in FIG. 1 can be used to relieve pain. In certain embodiments, the systems and methods presented in FIG. 1 can be used to relieve pain by means of applying pulsed RF electric fields to a dorsal root ganglion. In certain embodiments, the systems and methods presented in FIG. 1 can be used to relieve pain by means of applying pulsed RF therapy at a spinal nerve. In certain embodiments, the systems and methods presented in FIG. 1 can be used to relieve pain due to cancer. In certain embodiments, the systems and methods presented in FIG. 1 can be used to relieve pain due to cancer by means of radiofrequency heat lesioning of a dorsal nerve root; one advantage of heat lesioning of a nerve roots is improved control of the neurolytic zone relative to injection of neurolytic fluids, such as alcohol. One advantage of the application of radiofrequency signals, such as pulsed RF, using an epidurally placed electrode is that nerve structures at multiple levels of the spine can be targeted by moving the epidural electrode through the epidural space.

In certain embodiments, needle 170 can introduce catheter 160 through the skin of the human body. In certain embodiments, needle 170 can introduce catheter 160 through a natural opening in the human body, such as the urethra. In certain embodiments, needle 170 can introduce catheter 160 into a blood vessel of the human body. In certain embodiments, needle 170 can introduce catheter 160 into the epidural space of the human body. In certain embodiments, needle 170 can introduce catheter 160 into the subdural spaces of the human body. In certain embodiments, the entirety of the needle shaft 172 can be electrically insulated; one advantage of a fully insulated cannula 170 is that electrical signals cannot be inadvertently applied to the tissue on contact with the cannula 170 when the catheter's active tip 100 is in contact with the cannula 170.

Referring to FIG. 2, meaning FIGS. 2A, 2B, 2C, 2D, and 2E, in accordance with several aspects of the present invention, a unitized injection electrode is presented that comprises an active tip 200, an electrically insulated shaft 210, a hub 220, cables 230, electrical signal connector 240, and injection port 250. The electrode can be constructed so that its active tip 200, insulated shaft 210, hub 220, cables 230, signal connector 240, and injection port 250 are inseparably connected. The distal end of the electrode is the end of the active tip 200, and the proximal end of the electrode is end of the cables 230. Electrode structures that are more distal are closer to the distal tip 205. Electrode structures that are more proximal are closer to the generator connector 240 and/or to the injection port 250.

The active tip 200 is constructed from coil 201 and closed distal end 205. The closed distal end 205 can be a weld, which can be formed by laser, electrical discharge, or other methods known to one skilled in the art. The closed 205 distal end can be formed with conductive glue. The closed distal end 205 can be created using solder. The close distal end can be formed using glue. The closed distal end 205 can be configured to be electrically conductive. The closed distal end 205 can be configured to be electrically connected to the coil 201. The tip 200 can be configured to deliver electrical signals, such as stimulation and RF signals, to tissue, such as nerves. The tip 200 can be configured to allow for the outflow of fluid. The tip 200 can be configured to allow for preferential outflow of fluid from one or more parts of the tip. In the embodiment presented in FIG. 2, the tip 200 has a proximal region 202 which is closely-coiled wire. The tip 200 has a middle region 203 in which the coils are separated to allow for fluid outflow. For example, the outflow region 203 can have a ratio between wire diameter and inter-wire spacing of 1:1. The tip 200 has a distal region 204 which is closely-coiled wire. It is understood one or more of the tip regions 202, 203, and 204 can be omitted in other embodiments of the electrode.

The closed distal end 205 can have the same outer diameter as the outer diameter of the rest of the active tip 200. The closed distal end 205 can be full radiused. The closed distal end 205 can be hemispherical. The closed distal end 205 can be flat. The closed distal end 205 can have a smaller diameter than the outer diameter of the rest of the active tip 200. The closed distal end 205 can have a larger diameter than the outer diameter of the rest of the active tip 200. In another embodiment of the present invention, the distal end 205 can be open; an advantage of this embodiment is that fluid can exit the electrode from the distal end.

The insulated shaft 210 is constructed of electrical insulation 211 that surrounds the coil 201 within it. The coil 201 within the shaft can be closely coiled wire like that of the proximal tip region 202. In one embodiment, the coil 201 can extend through the entire length of the shaft 210. In one embodiment, the coil 201 can extend only part of the length of the insulated shaft 210 and connect to another structure that has different flexibility, such as a tube or a spiral-cut tube. In one embodiment, the coil 201 can extend though the shaft 210 and the hub 220. In one embodiment, the coil 201 can extend though the shaft 210, the hub 220, and the cables 230.

The tip 200 and shaft 210 can be flexible. The tip 200 and shaft 210 can be configured for placement within the epidural space in the human body. The coil 201 can be a stainless steel spring coil. In one example, the coil 201 can be a spring coil used in the construction of epidural catheters, as is familiar to one skilled in the art of epidural anesthesia. The coil 201 can be constructed of wound round wire. The coil 201 can be constructed of wound flat wire. The coil 201 can be laser-cut tubing. The coil 201 can be laser-cut stainless-steel hypodermic tubing. The electrical insulation 211 can be constructed from one or more pieces and/or applications of medical grade plastic tubing, fluoropolymers, fluoroelastomers, silicone, polyester, polyolefin, polyimide, and other materials that are familiar to one skilled in the art of RF electrodes and epidural catheters. The electrical insulation 211 can be constructed from materials configured to produce shaft stiffness appropriate for epidural placement in the human body. The electrical insulation 211 can be a single a tube of fluoropolymer material, such as PTFE, FEP, ETFE, PET. The electrical insulation 211 can be heat shrink tubing that is shrunk over the coil 201. The electrical insulation 211 can be applied by coating the wire of the coil 201 before that wire is wound into the coil 201. The electrical insulation 211 can be PTFE heat shrink tubing that is shrunk over the coil 201. The electrical insulation 211 can be FEP heat shrink tubing that is shrunk over the coil 201. The electrical insulation 211 can be ETFE heat shrink tubing that is shrunk over the coil 201. The electrical insulation 211 can be PET heat shrink tubing that is shrunk over the coil 201. The electrical insulation 211 can consist of two layers of plastic material that surround the spring coil 201, as is familiar to one skilled in the art of epidural anesthesia catheters. The electrical insulation 211 can be produced by applying a layer of a first material to the coil, for example by spraying or painting, and then applying a second material, such as a tube, over the first material. The coil 201 can be wound wire of 0.004 inch diameter. The coil 201 can be wound wire of 0.005 inch diameter. The coil 201 can be wound wire of 0.006 inch diameter. The coil 201 can be wound wire of 0.007 inch diameter. The coil 201 can be wound wire of less than 0.004 inch diameter. The coil 201 can be wound wire of greater than 0.007 inch diameter. The outer diameter of the coil 201 can be in the range 21 gauge to 18 gauge. The outer diameter of the coil 201 can be smaller than 21 gauge. The outer diameter of the coil 201 can be larger than 18 gauge. The outer diameter of the coil 201 can be 20 gauge. The outer diameter of the coil 201 can be 19 gauge. The electrical insulation 211 can have wall thickness in the range 0.003 inches to 0.008 inches. The electrical insulation 211 can have wall thickness less than 0.003 inches. The electrical insulation 211 can have wall thickness greater than 0.008 inches. The electrical insulation 211 can have wall thickness 0.005 inches. The outflow section of the coil 203 can have spaces between adjacent coil loops that is substantially equal to the thickness of the wire from which the coil is wound. The outflow section of the coil 203 can have spaces between adjacent coil loops that is in the range 0.003 inches to 0.008 inches. The outflow section of the coil 203 can have spaces between adjacent coil loops that is less than 0.003 inches. The outflow section of the coil 203 can have spaces between adjacent coil loops that is greater than 0.008 inches. The outflow section of the coil 203 can have spaces between adjacent coil loops that is 0.005 inches. The outflow section of the coil 203 can have spaces between adjacent coil loops that is 0.006 inches. The length of the outflow section of the coil can be in the range 0.100 to 0.140 inches. The length of the outflow section of the coil can be less than 0.100. The length of the outflow section of the coil can be greater than 0.140 inches. The length of the outflow section of the coil can be 0.120 inches.

In another embodiment of the electrode, more than one segment of insulation can be applied along the length of the electrode shaft, with bare coil 201 between each segment; an advantage of this embodiment is that RF energy can be applied to multiple separated tissue regions without applying RF energy directly to intervening regions. In another embodiment, a segment of insulation can cover closed end 205 and the distal end 204 of the tip 200. In another embodiment of the electrode, the insulation can be configured such that at one or more segments of the shaft, there is a gap in the insulation on one side of the shaft that exposes the underlying coil 201, and insulation covers the other opposite side of the coil; an advantage of this embodiment is that RF energy can be applied to tissue in contact with only one side of the electrode.

The tip 200 can have length between 2 mm and 60 mm. The tip 200 can be longer than 60 mm. The length of the active tip 200 can be 5 mm. The length of the active tip 200 can be 10 mm. The length of the active tip 200 can be 15 mm. The length of the active tip 200 can be 20 mm. The length of the active tip 200 can be 25 mm. The length of the active tip 200 can be 30 mm. The active tip 200 can have length configured to the application of RF signals to nerves for pain management. The active tip 200 can have length configured for epidural placement and injection of epidural anesthetics.

The length of the shaft 210 can be between 12 inches and 33 inches. The length of the shaft 210 can be configured for epidural anesthesia procedures, as if familiar one skilled in the art. The length of the shaft 210 can be longer than 33 inches. The length of the shaft 210 can be shorter than 12 inches. The length of the shaft 210 can be 16 inches. The length of the shaft 210 can be configured to reach the L2 vertebral level percutaneously and epidurally via the sacral hiatus.

The hub 220 can have a diameter larger than the insulated shaft 210. The hub 220 can be configured to facilitate rotation of the electrode shaft 210 and tip 200. The hub 220 can be omitted and the cables 230 can connect directly to the shaft 210. The hub 220 can have similar outer dimension and aspect as tuohy-borst adaptors that are typically attached to the end of epidural catheters, as is familiar one skilled in the art. The hub 220 can have outer diameter in the range 0.250 inches to 0.500 inches. The hub 220 can have outer diameter less than 0.250 inches. The hub 220 can have outer diameter greater than 0.500 inches.

The cable 230 can be flexible. The cable 230 can be rigid. The cable 230 can have both rigid and flexible element. The cable 230 can have a hollow inner lumen capable of carrying injected fluids into the electrode shaft 210 and tip 200. The cable 230 can contain a tube capable of carrying wires for connection to the jacks on an RF generator. In one embodiment, the cables 230 can be construction from flexible tubes, glue, and wires for connection to the generator. In one embodiment, the cables 230 can be construction from flexible tubes, glue, a Y-splitter structure, and wires for connection to the generator. In one embodiment, the cable 230 can be constructed like the cable of the Cosman CU electrode, sold by Cosman Medical, Inc. In other embodiments, the cable can be constructed using the systems and methods presented in U.S. Pat. No. 7,862,563 by E R Cosman Sr and E R Cosman Jr. In the embodiment shown in FIG. 2, the cable 230 has a single root 231 that connects to the hub 220, a branch 232 that connects to and carries fluid from injection port 250, and a branch 233 that connects to and carries wires from the connector 240.

The electrical signal connector 240 can be configured to carry signals from an RF generator to the active tip 200 of the electrode, as is familiar to one skilled in the art. In one embodiment, the connector 240 can be configured to connect to a nerve stimulation device The connector 240 can be configured to carry sensory nerve stimulation signals, motor nerve stimulation signals, thermal RF signals, pulsed RF signals, signals with carrier frequency in the radiofrequency range, signals with carrier frequency 500 kHz, signals with one component in the radiofrequency range, signals with one component in the range 250-1000 kHz. The connector 240 can be configured to carry temperature measurement signal(s) from the electrode to an RF generator or another temperature measurement device, as if familiar to one skilled in the art. In the embodiment presented in FIG. 2, the generator plug 240 comprises two pins 242 and 243, of which one can both connect to one output pole of an RF generator and to one pole of the RF generator's temperature sensing circuit, and of which the other can connect to the second pole of the RF generator's temperature sensing circuit. For example, pin 242 can connect to one lead from a thermocouple or thermistor sensor in the active tip 200 of the electrode, and pin 243 can connect to the other lead from the said thermocouple or thermistor sensor in the active tip 200 of the electrode. The connector 240 can be configured to carry other signals, such as additional temperature measurement signals, as is familiar to one skilled in the art. In one embodiment, the connector 240 can have more than two pins. In one embodiment, the connector 240 can have three pins. In one embodiment, the connector 240 can have at least three pins, of which one carries therapeutic and/or diagnostic signals from a generator to the electrode, and the other two connect to a thermocouple contained in the electrode.

The injection port 250 can be configured to carry injected fluids into and through the cables 230, the hub 220, the shaft 210, and out the tip 200. The injection port 250 can be configured to aspirate fluids from the electrode tip 200, for example to confirm proper placement of the electrode tip 200, as is familiar one skilled in the art of epidural anesthesia. The injection port can be a female luer injection port. The port 250 can have a luer lock. The port 250 can have a cap. The cable 232 connecting the luer injection port can have an external clamp to prevent outflow of fluids.

One advantage of the embodiments of a one-piece electrode catheter presented in FIG. 2 is ease of manufacturing.

Figure 2A:
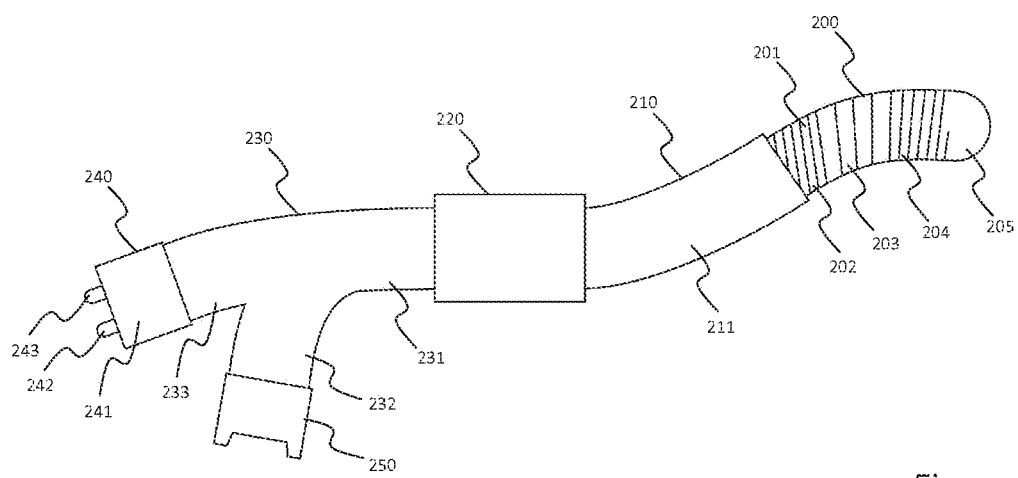
FIG. 2A is a schematic diagram showing in an external view a unitized injection electrode with a flexible active tip, a flexible shaft, an injection port, and a generator connector.

FIG. 2A presents one embodiment of the present invention in which the shaft 210 and tip 200 are positioned in one example of a flexed position.

Figure 2B:
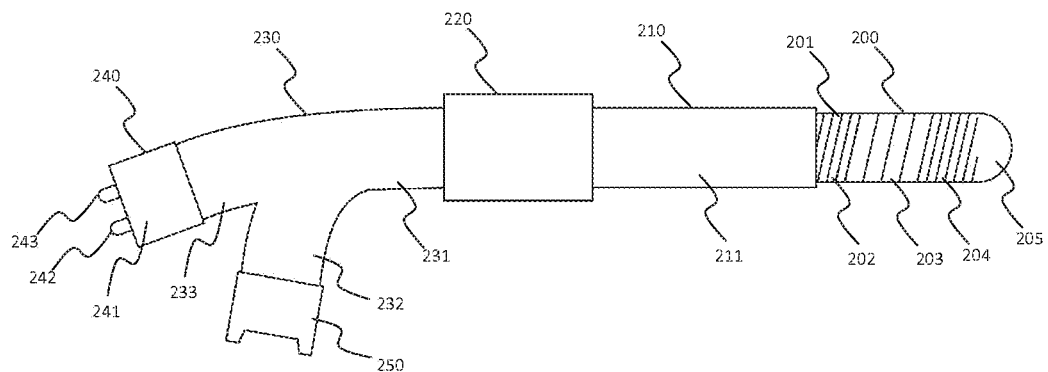
FIG. 2B is a schematic diagram showing in an external view a unitized injection electrode with a flexible active tip, a flexible shaft depicted in a straight position, an injection port, and a generator connector.

FIG. 2B presents the electrode shown in FIG. 2A, where its flexible tip 200 and flexible shaft 210 are in substantially straight position.

Figure 2C:
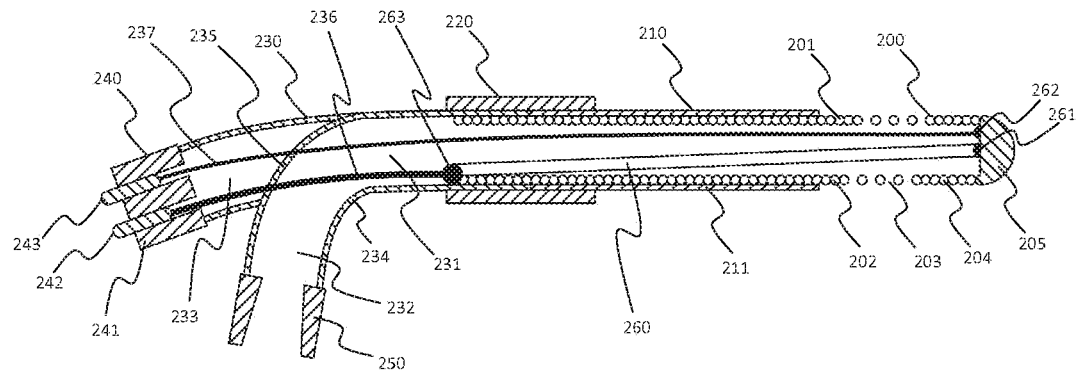
FIG. 2C is a schematic diagram showing in a sectional view a unitized injection electrode where a coil is used in the construction of the shaft and active tip, and where the electrode has a an integrated stylet, temperature sensor, injection port, and a generator connector.
Figure 2D:
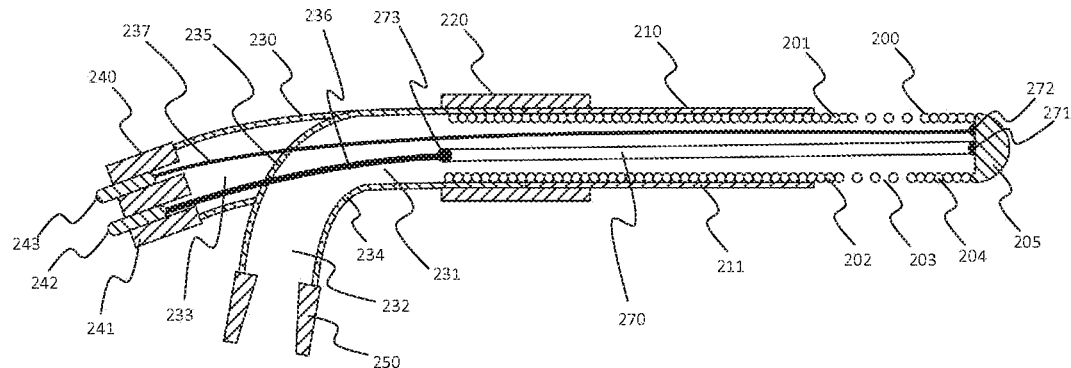
FIG. 2D is a schematic diagram showing in a sectional view a unitized injection electrode where a coil is used in the construction of the shaft and active tip, and where the electrode has a an integrated stylet, temperature sensor, injection port, and a generator connector.
Figure 2E:
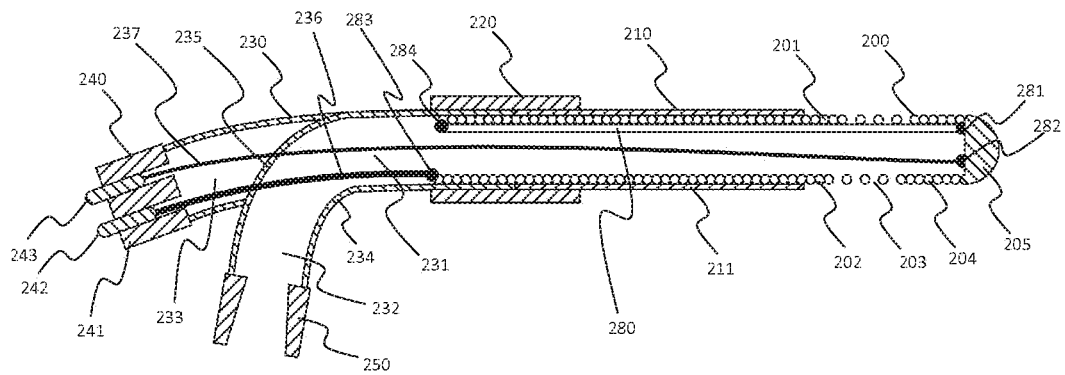
FIG. 2E is a schematic diagram showing in a sectional view a unitized injection electrode where a coil is used in the construction of the shaft and active tip, and where the electrode has a an integrated safety strap, temperature sensor, injection port, and a generator connector.

FIG. 2C, FIG. 2D, and FIG. 2E present three embodiments of the internal construction of the electrode from FIGS. 2A and 2B, shown in cross-sectional views. Referring now to FIG. 2C, FIG. 2D, and FIG. 2E, the coil 201 is shown in a cross-sectional view wherein round-wire winds appear substantially elliptical. In another embodiment of coil 201, the cross-section of the coil 201 does not appear as an ellipse, for example if flat wire is used to construct the coil 201, the cross section has a substantially rectangular. In one example, the coil 201 is a stainless steel spring coil, which is familiar to one skilled in the art of epidural catheters. The closed distal end 205 of the tip 200 is shown in cross-section. The insulation 211 is shown in a cross-sectional view wherein its tubular structure appears on both sides of the coil 201. In one example, the insulation 211 is a flexible plastic tube, familiar to one skilled in the art of epidural catheters. In one example, the insulation 211 is constructed from a flexible plastic tube within which is another coating, as is familiar to one skilled in the art of epidural catheters. The hub 220 is shown in cross-section wherein its tubular structure appears on both sides of the insulation 211 and the tubing 234. In one example, the hub 220 is a rigid structure composed of a plastic tube and glue that prevents fluid leakage out from the coil 201, insulation 211, and injection tube 234. The injection tube 234 is shown in a cross-sectional view wherein its tubular structure appears on opposite sides of the central lumen of the injection branch 232 and the root 231 of the cable 230. The injection tube 234 connects the injection port 250 and the hub 220. The injection tube 234 provides a channel through which fluids injected into the injection port 250 can flow into the shaft 210, into the tip 200, and then out from spaces between the coil loops of the tip 200, preferentially through the larger gaps between coil loops in the outflow section 203 of the tip 200. The injection port 250 is shown in a cross-sectional view wherein it appears on opposite sides of the opening at the end of the injection port branch 232 of the cable 230. The port 250 can be a female luer connector. The connector branch 233 of the cable 230 is shown in cross-sectional view so that its walls appear on opposite sides of the internal space through which wires 236 and 237 travel from the generator connector 240 into the root 231 of the cable 230. The connector 240 is shown in a cross-sectional view wherein pins 242 and 243 and mounted within the body 241, which appears in three parts around and between the pins 242 and 243. It is understood that the wires 236 and 237 can each be constructed from multiple pieces of wire, rod, tubing, solder joints, crimps, hooks, and other elements familiar to one skilled in the art of medial device manufacturing.

The wall 235 of the injection tube 234 limits fluid flow into the connector branch 233 of the cable 230. It is understood that this wall portion 235 can, in another embodiment, be constructed of a different material from that of the tube 234; for example, from a glue plug. The wires 236 and 237 travel through the wall 235. It is understood that other embodiments of the construction of the cables 230 can be used to provide both connection to a generator and a pathway for injection of fluids. For example, the cable constructions presented in U.S. Pat. No. 7,862,563 by E R Cosman Sr and E R Cosman Jr can be used. For example, the cable 230 can be constructed like the cable of the Cosman CU electrode, sold by Cosman Medical, Inc.

The wire 236 can be configured to carry electrical signal output from an RF generator and/or a stimulation waveform generator. The wire 236 can be composed of a conductive material, such as copper. The wire 236 can be coated with an electrical insulator. The wire 236 can be bare. The wire 236 can be configured to connect via pin 242 to both the electrical signal output of a generator, such as an RF generator, and to the first terminal of a temperature-monitoring circuit, which can be integrated into the same generator or which can be housed in a separate unit. The wire 237 can be configured to connect via pin 243 to the second terminal of the said temperature monitoring circuit. The wire 237 can be an electrically-insulated constantan wire. In another embodiment, pin 242 connects to the electrical signal output of a generator, wire 236 carries signals from the output of said generator, pin 243 has isolated prongs each of which connects to a isolated terminal of a temperature-monitoring circuit, and wire 237 is an bifilar thermocouple wire, such as a copper-constantan bifilar.

Referring now specifically to FIG. 2C, the unitized injection electrode includes a central wire 260 within the inner lumen of the coil 201. The central wire 260 can be configured to stiffen the shaft 210 and the tip 200 of the electrode. The central wire 260 can improve torque transmission from the proximal end of the shaft 210 to the distal end of the shaft 210. The central wire 260 can be configured to provide sufficient stiffness for epidural placement of the electrode, and limited stiffness to prevent puncture of sensitive structures around the epidural space, as is familiar to one skilled in the art of epidural catheters. The central wire 260 can be a stainless steel rod. The central wire 260 can be copper. The central wire 260 can be a tapered metal rod. The central wire 260 can be a rod with a substantially circular cross section. The central wire 260 can be a hollow tube. The central wire 260 can be a plastic rod. The central wire 260 can be a rod with a substantially rectangular cross section. The central wire 260 can be electrically conductive. The central wire 260 can be electrically insulative. The rod 260 can be a bare metal structure. The rod 260 can be covered by an electrically-insulative coating. The central wire 260 can have an outer dimension in the range 0.001" to 0.016". The central wire 260 can have an outer diameter 0.010". The central wire can have an outer diameter 0.011". The central wire 260 can have an outer diameter 0.012". The central wire can have an outer diameter 0.013". The central wire 260 can have an outer diameter 0.014". The central wire can have an outer diameter greater than 0.016". The central wire 260 can have an outer diameter configured to fit within the coil 201 and to allow injected fluid to flow from one end of the coil to the other. The central wire 260 can be configured to conduct electrical signals, such as high frequency signals, RF output, and nerve stimulation signals, from a generator to the tip 200 of the electrode. The central wire 260 can be configured to reduce the impedance of electrical potentials, such as high frequency electrical waveforms, radiofrequency potentials, and nerve stimulation waveforms, between the generator connector 240 and the uninsulated metallic electrode tip 200. The dimensions of the central wire 260 can be configured to provide a flow path of desired area for injected fluids along the electrode shaft.

The central wire 260 can be attached at the distal end of the coil 201 and at the proximal end of the coil 201; one advantage of this embodiment of the invention is that the central wire 260 prevents extension of the coil 201 if its distal end 204 or the closed end 205 is caught in some anatomy, such as between two vertebra. The central wire 260 can carry electrical signals from the generator to the tip 200 of the coil 201; one advantage of this of this embodiment of the invention is that it reduces the electrical impedance between the generator and the active tip 200 of the electrode. The central wire 260 can be configured to maintain a bent configuration. The central wire 260 can be configured to maintain a bent configuration when bent by the user, such as a physician. An advantage of central wire 260 holding a bend is that a bend can be imposed in the electrode shaft. An advantage of a bent electrode shaft is that the bend can maneuvering of the electrode in the human body, such as in the epidural space.

The central wire 260 is connected at junction 263 to both the proximal end of the coil 201 and to the wire 236. The junction 263 can be electrically conductive. The junction 263 can create an electrically connection between the wire 263 and the coil 201. The junction 263 can create an electrical connection between the wire 263 and the central rod 260. The junction 263 can be configured to transmit electrical signals from the wire 263 to the coil 201, either by direct electrical connection of the wire 263 to the coil 201, by electrical connection between the wire 263 and rod 260 and then electrical connection between the rod 260 and the coil 201 at junction 261, or both. In one example, the junction 263 is a solder joint. In another example, the junction 263 includes both a weld and a solder joint. In another example, the junction 263 includes glue. In another example, the junction 263 includes a mechanical lock. In another example the junction 263 is a weld, such as a laser weld. In one example, the junction 263 is a solder joint that incorporates the coil 201, the wire 236, and the central wire 260. In another example, the junction 263 is a solder joint between the wire 236 and the central wire 260, and the central wire 260 is configured so that it mechanically locks with the coil 201; for instance, the central wire 260 can be folded over on itself so that it hooks around the proximal end of the coil 201. In another example, the junction can be a laser weld between the central wire 260 and the coil 201, and a solder joint between the wire 236 and the coil 201. It is understood that the junction 263 can take other forms as is familiar to one skilled in the art of medical device manufacturing. In another embodiment, the central wire 260 can be anchored to another element of the hub 220.

The central wire 260 is connected to the closed distal end 205 of the tip 200 at junction 261. The junction 261 can be electrically conductive. The junction 261 can be electrically insulative. The junction 261 can be configured so that the rod 260 and the closed distal end 205 connected electrically. In one example, the junction 261 is part of the weld that formed the closed distal end 205. It is understood that the junction 263 can take other forms as is familiar to one skilled in the art of medical device manufacturing, including without limitation, gluing, welding, soldering, crimping, hooking, mechanical locking.

The wire 237 is connected to the closed distal end 205 of the tip 200 at junction 262. The junction 262 can be electrically conductive. The junction 262 can be electrically insulative. The junction 262 can be configured so that the rod 260 and the closed distal end 205 connected electrically. In one example, the junction 262 is part of the weld that formed the closed distal end 205. It is understood that the junction 263 can take other forms as is familiar to one skilled in the art of medical device manufacturing, including without limitation, gluing, welding, soldering, crimping, hooking, mechanical locking. In one embodiment the wire 237 is an insulated constantan wire, the coil 201 is stainless steel, and the junction 262 is electrically conductive such that it forms a thermocouple junction. In one embodiment the wire 237 is an insulated metal wire, the coil 201 is composed of a dissimilar metal, and the junction 262 is electrically conductive such that it forms a thermocouple junction. In one embodiment, the closed distal end 205 is a weld that incorporates both the wire 237 and the coil 201. In one embodiment, the closed distal end 205 is a solder joint that incorporates both the wire 237 and the coil 201. In one embodiment, the wire 237 is a thermocouple bifilar, such as a copper-constantan bifilar, as is familiar to one skilled in the art of thermocouples, and the junction includes an element that forms the thermocouple junction between the two wires of the bifilar 237, for example by means of a weld, and an element that mechanically attaches the distal end of the bifilar wire 237 to the closed end of the coil 205.

It is understood in different embodiments that the wire 237 can take any one of a number of paths along the shaft 210, for example, entirely within the coil inner lumen, between the coil 201 and insulation 210, or passing into the inner lumen and out into the space between the insulation 211 and the coil 201 by passing between adjacent loops of the coil 201 any number of times.

In one example, the closed end of the coil is a weld that connects the wire 237, the rod 260, and the coil 201. In one example, the closed end of the coil is a solder joint that connects the wire 237, the rod 260, and the coil 201.

In one example, the wire 236, the central wire 260 and the coil 201 itself carry electrical output of an electrosurgical generator, such as radiofrequency and/or stimulation waveforms, to the tip 200 of the electrode. In one example, wires 236 and 237 connect to opposite poles of a temperature sensor, such as a thermocouple junction, at the tip 200 of the electrode, and conduct signals from said temperature sensor to a temperature monitoring system.

In another embodiment, the temperature connection 243, the wire 237, and the junction 262 can be omitted. In this embodiment, electrical signals are conducted through the electrode without temperature monitoring. An advantage of this embodiment is that it is easier to build. An advantage of this embodiment is that the electrode provides for stimulation-guided placement in the epidural space. An advantage of this embodiment is that it can be used for non-temperature-monitored application of RF therapy, such as thermal RF lesioning and pulsed RF treatment.

In one embodiment of the present invention, an example of which is shown in FIG. 2C, the unitized electrode is configured for placement in the epidural space, temperature monitoring of the electrode's active tip, and delivery of radiofrequency signals via the electrode's active tip; wherein the electrode consists of a metallic coil with a proximal and distal end, an electrically insulative sheath that covers the proximal length of the coil and leaves the distal end of the coil exposed, a temperature sensor in exposed distal end of the coil, a port that allows for injection of fluids into the inner lumen of the coil, and a connector to an electrosurgical generator. In a more specific embodiment, the unitized electrode includes a central wire that mechanically connects the distal end of the coil to proximal hub structures. In a more specific embodiment, the said spring coil is stainless steel. In a more specific embodiment, a thermocouple junction is formed at the distal tip of the electrode by welding a constantan wire to the coil and to the central metallic wire.

Referring now to FIG. 2D, the unitized injection electrode includes a central wire 270. In this embodiment, junction 273 connects the central wire 270 and the wire 236, and junction 271 connects the central wire 270 to the closed distal end 205 of the active tip 200. Junction 272 is the connection of the wire 237 to the closed distal end 205 of the active tip 200. In one embodiment, high frequency electrical signals are carried to the active tip 200 of the electrode via wire 236 and rod 270. In one embodiment, the junction between wires 237 and 270 at the closed distal end 205 form a thermocouple junction. In one embodiment, the wire 236 is a bifilar wire that carries signals from a temperature sensor at junction 272. The junction 273 and wire 236 can be configured to anchor the rod 270 to the generator connector; an advantage of this configuration is that the wire 270 prevents the tip 200 from separating from the electrode. The junction 273 can include elements familiar to one skilled in the art of medical device construction, including soldering, welding, crimping, clamping, gluing, hooking, and twisting. In one example, the rod 270 is cover by electrically insulation along its length, so that signals carried by wire 236 are not conveyed to the closed distal end 205 by the coil 201. In another example, the rod 270 is uninsulated so that electrical signals are carried to the active tip 200 via the coil 201 if the coil touches the central wire 270. The central wire 270 can be a metal rod. The central wire 270 can be a flat wire with rectangular cross section. The central wire 270 can have outer diameter at a value in the range 0.001 to 0.018 inches. The central wire 270 can have outer diameter 0.011 inches. The central wire 270 can have a rectangular cross section with cross section substantially similar to 0.003 inches by 0.009 inches. The central wire 270 can be dimension and geometry configured to provide desired separation force between the tip 200 and the hub 220. The central wire 270 can be dimension and geometry configured to provide desired separation force between the distal end of the coil 201 and the proximal end of the coil 201. The central wire 270 can be configured to produce a desired flexibility for the shaft 210 and tip 200. The central wire 270 can be configured to maintain a bent configuration. The central wire 270 can be configured to maintain a bent configuration when bent by the user, such as a physician. An advantage of central wire 270 holding a bend is that a bend can be imposed in the electrode shaft. An advantage of a bent electrode shaft is that the bend can maneuvering of the electrode in the human body, such as in the epidural space. The central wire 270 can be configured so that the electrode is suitable for placement in the epidural space.

Referring now to FIG. 2E, the unitized injection electrode includes a safety strap 280. The safety strap 280 is connected to the distal end of the coil 201 at junction 281 and to the proximal end of the coil 201 at junction 283. The wire 236 is connected to the coil 201 at junction 283. The wire 237 is connected to the distal end of the coil 201 at junction 282. The wire 236 and the coil 201 itself can carry RF output and/or stimulation output to the active tip 200 of the electrode from a medical electrosurgical generator to which connector 240 is attached. In one embodiment, the junction between the spring coil 201 and the wire 237 at the closed distal end 205 of the coil 201 forms a temperature sensor, such as a thermocouple, and the wires 236 and 237 carry signals from said temperature sensor to the connector 240. In another embodiment, the wire 237 is a bifilar wire, such as a copper-constantan thermocouple wire, and junction 272 is a temperature-sensing junction, such as a thermocouple weld, that is mechanically anchored to the tip 200. The safety strap 280 can be a metal rod. The safety strap 280 can be a flat wire with rectangular cross section. The safety strap 280 can have outer diameter at a value in the range 0.001 to 0.018 inches. The safety strap 280 can have outer diameter 0.010 inches. The safety strap 280 can have a rectangular cross section with cross section substantially similar to 0.003 inches by 0.009 inches. The safety strap 280 can be dimension and geometry configured to provide desired separation force between the tip 200 and the hub 220. The safety strap 280 can be dimension and geometry configured to provide desired separation force between the distal end of the coil 201 and the proximal end of the coil 201. The safety strap 280 can be configured to produce a desired flexibility for the shaft 210 and tip 200. The safety strap 280 can be configured to maintain a bent configuration. The safety strap 280 can be configured to maintain a bent configuration when bent by the user, such as a physician. An advantage of safety strap 280 holding a bend is that a bend can be imposed in the electrode shaft. An advantage of a bent electrode shaft is that the bend can maneuvering of the electrode in the human body, such as in the epidural space. The safety strap 280 can be configured so that the electrode is suitable for placement in the epidural space.

Figure 3:
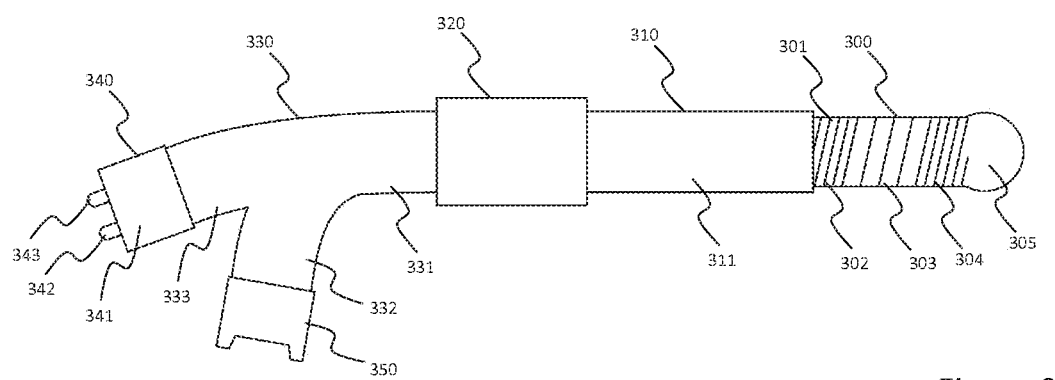
FIG. 3 is a schematic diagram showing a unitized injection electrode with a flexible active tip, closed distal end with diameter larger than the outer diameter of the proximal part of the active tip, a flexible shaft, an injection port, and a generator connector in an external view.

FIG. 3 presents a unitized injection electrode for which the closed distal end 305 has a larger outer diameter than the outer diameter of the rest of the active tip 300, in accordance with several aspects of the present invention. In one embodiment, the electrode in FIG. 3 is analogous to the electrode presented in FIG. 2. The electrode comprises a flexible active tip 300, an electrically-insulated flexible shaft 310, a hub 320, cables 330, electrical signal connector 340, and injection port 350. The electrode can be constructed so that its active tip 300, insulated shaft 310, hub 320, cables 330, signal connector 340, and injection port 350 are inseparably connected. The distal end of the electrode is the end of the active tip 300, and the proximal end of the electrode is end of the cables 230. As in the electrode presented in FIG. 2A, in one embodiment, the tip 300 and shaft 310 include a coil 301, and electrical insulation 311 covers the coil in the shaft region 310 and is absent in the tip region 300, to form the metallic active tip 300 of the electrode. The tip includes an outflow region 303 that can be configured to preferentially emit fluids injected into the port 350. The active tip 300 can be configured to be energized by a generator attached to connector 340. Temperature can be measured at the active tip 300 by a temperature measurement circuit attached to the connector 340. The length of the electrode's shaft 310 can be configured for epidural placement. The length of the electrode's active metallic tip 300 can be in the range 2-30 mm or more, and it can be configured by performing RF and pulsed RF therapy.

FIGS. 4A and 4B each present a unitized injection electrode with movable stylet 460, in accordance with several aspects of the present invention. The electrode with stylet 460 can be configured for placement in the epidural space. Referring to both FIG. 4A and FIG. 4B, the stylet 460 comprises a hub 461 and shaft 462. The electrode, within which the sytlet 460 can move, comprises an active tip 400, an electrically insulated shaft 410, a hub 420, cables 430, electrical signal connector 440, and injection port 450. The electrode can be constructed so that its active tip 400, insulated shaft 410, hub 420, cables 430, signal connector 440, and injection port 450 are inseparably connected. In FIGS. 4A and 4B, the sylet 460 is shown positioned within the unitized injection electrode. The tip 400 can be constructed from a metallic coil 401, such as stainless steel spring coil, and have regions of tight coiling 402 and 404, and regions of looser coiling 403 to allow for preferential outflow of fluids injection into port 450, and a closed distal end 405 that is, in one embodiment, blunt and atraumatic. The coil 401 can extend into the shaft region 410, where it is covered by electrical insulation 411. The active tip 400 can be configured to be energized by a generator attached to connector 440. Temperature can be measured at the active tip 400 by a temperature measurement circuit attached to the connector 440. The stylet hub 461 can be configured to be grasped by human fingers. The stylet hub 461 can be omitted. The electrode hub 420 can be omitted. The length of the electrode's shaft 410 can be configured for epidural placement. The length of the electrode's shaft 410 can be in the range 12 to 33 inches. The length of the electrode's active metallic tip 400 can be in the range 2-30 mm or more, and it can be configured by performing RF and pulsed RF therapy. The diameter of the electrode shaft 410 and tip 400 can be in the range 21 gauge to 18 gauge. Electrode shaft 410 and tip 400 can be substantially equal to 19 gauge. Electrode shaft 410 and tip 400 can be substantially equal to 20 gauge. Electrode shaft 410 and tip 400 can configured for epidural placement.

The distal end of the electrode is the end of the active tip 400, and the proximal end of the electrode is end of the cables 430. Electrode structures that are more distal are closer to the distal tip 405. Electrode structures that are more proximal are closer to the generator connector 440 and/or to the injection port 450. The distal end of the stylet 460 is the distal tip 463. The proximal end of the stylet 460 is the handle 461.

When inserted, the stylet 460 can enter the port 450, travel through branch 432 and 431 of the cables 430, the hub 420, shaft 410, and all, part, or none of the tip 400. In one embodiment, not shown, the cable branches 431 and 432 can present a straight path through which the stylet moves. In one embodiment, the cable branches 431 and 432 can be rigid in whole or in part to facilitate movement of the stylet shaft 462 within them. In one embodiment the cable branch 433 that is associated with the generator connector 440 is flexible. In another embodiment the cable branch 433 that is associated with the generator connector 440 is rigid.

The shaft 410 and tip 400 can both be flexible when the stylet 460 is inserted and when the stylet 460 is not inserted. The stylet can be physically separable 460 from the electrode. An advantage of the embodiment where the stylet 460 can be fully withdrawn and removed from the electrode is that when the stylet is fully removed from the electrode, fluids can be injected into port 450 and delivered to anatomy nearby the electrode tip 400. The stylet 460 can be physically inseparable from the electrode, for example, by providing a mechanical element that prevents removal of the stylet from the electrode. The electrode and stylet 460 can be configured to enable the user to move the stylet 460 within the inner lumen of the electrode; an advantage of a unitized injection electrode with a moveable stylet 460, is that the stylet 460 can be moved to adjust the flexibility of the electrode tip 400 and shaft 410. The electrode and stylet 460 can be configured for placement in the epidural space of the human body. The electrode can be configured to provide for radiofrequency treatment and injection of fluids, such as radiocontrast agents, anesthetics, neurolytics agents, alcohol, phenol, saline, hyaluronidase, local anesthetic, corticosteroids, hypertonic saline. The electrode can be configured to monitor the temperature at the tip 400 of the electrode. The electrode and stylet 460 can be configured for stimulation-guided epidural anesthesia, such as lysis of adhesions. The electrode can be configured to be radiopaque. The stylet shaft 462 can be configured to be radiopaque. An advantage of the electrode being radiovisible is that x-ray guidance, such a fluoroscopy, can be used to position the electrode in the human body. An advantage of the stylet 460 being radiovisible is that x-ray guidance, such a fluoroscopy, can be used to position the electrode in the human body. The construction of the stylet 460 can be that of epidural catheters. The stylet shaft 462 can be a stainless steel rode. The stylet shaft 462 can have outer diameter that is a value in the range 0.001 inches to 0.018 inches. The stylet shaft 462 can have outer diameter greater than 0.018 inches. The stylet shaft 462 can have outer diameter that is 0.010 inches. The stylet shaft 462 can be configured to be flexible enough to move through the cables 430, shaft 410, and tip 400. The stylet shaft 462 can be configured to maintain a bent configuration. An advantage of the sytlet 460 holding a bend is that a bend can be imposed in the electrode shaft when the stylet 460 is in place. An advantage of a bent electrode shaft is that the bend can maneuvering of the electrode in the human body, such as in the epidural space.

Referring now to FIG. 4A, an external view of a unitized injection electrode and stylet 460 is shown.

Referring now to FIG. 4B, a cross-section of the unitized injection electrode is presented and shows one embodiment of its construction. The shaft 462 of the stylet 460 is within the inner lumen of the coil 401, which appears as a series of substantially circular elements in the cross-sectional view. The tip of the stylet 463 can touch the inner surface of the electrode's distal end 405 when the stylet is fully inserted. The tip of the stylet 463 can be configured so that is cannot touch the inner surface of the electrode's distal end 405 when the stylet is fully inserted. One advantage of the distal tip of the stylet's 463 not being able to touch the inner surface of the electrode's distal end when fully inserted is that it ensures the distal end of the coil 401, for instance the region 404, is less stiff than the rest of the tip 400 and shaft 410 at all times.

Pin 442 of connector 440 can be configured to connect to the electrical output of a medical electrical generator, such as an RF generator or a nerve stimulator. Pin 442 is connected to wire 436. Wire 436 is connector to the coil 401 and the safety strap 480 at junction 484. Safety strap 480 is connected to the coil 401 at its distal end 405 at junction 481. Pin 442, wire 236, coil 401, strap 480 can be configured to carry electrical signals, such as RF generator output, to the active tip 400 of the electrode from a medical generator connected to pin 442. In another example, the safety strap 480 can be electrically insulative. The wire 436 can include a conductive metal, such as copper. The safety strap 480 can include a conductive metal, such as stainless steel. The safety strap 480 can be a stainless steel flat wire. The cross-section of the safety strap can be substantially rectangular with dimension substantially similar to 0.005 inches by 0.010 inches. One advantage of the safety strap 480 being a flat wire is that the safety strap 480 has a low profile. One advantage of the safety strap 480 being a flat wire is that the safety strap 480 obstructs less of the fluid flow path within the lumen of the coil 401. One advantage of the safety strap 480 being a flat wire is that a larger diameter stylet shaft 462 can passed into the inner lumen of the coil 401. The safety strap 480 can be configured to help prevent the coil 401 from changing length and/or uncoiling within the body. In another embodiment, the safety strap 480 can be omitted, in which case junction 484 is between wire 436 and coil 401, and the coil 401 itself carries electrical signals to its active tip 400.

In one embodiment pin 443 connects to one pole of temperature-monitoring circuit and pin 442 connects to the other pole of said temperature-monitoring circuit. In this embodiment, wire 437 connects to pin 443 and is electrically-insulated constantan wire, and the safety strap 480 and coil 401 can both be stainless steel. The distal end of the coil 405 can be a weld that connects the coil 401, the strap 480, and the constantan wire 237 to form a thermocouple junction from which the said temperature-monitoring circuit measures temperatures. In another embodiment, pin 443 has two electrically-isolated prongs that connect to both poles of a temperature-monitoring circuit, the wire 437 is a bifilar of dissimilar metals, such as copper-constantan thermocouple wire, the junction 482 is the thermocouple formed by connection of the two wires of the bifilar 437 to form a thermocouple, and the temperature-monitoring circuit measures temperature from the thermocouple 482; the thermocouple 482 can be connected to the coil 401 within the length of the tip or to its closed distal end 405.

It is understood, that the wire 437 can be positioned outside the coil for all or part of the length of the hub 420 and shaft 411. It is understood, that the wire 437 can pass into and out of the coil 401 along its length by passing between adjacent loops of the coil 401. One advantage of the wire 437 being outside the inner lumen of the coil 401 is that it is like likely to be damaged by the movable stylet shaft 462.

Figure 5A:
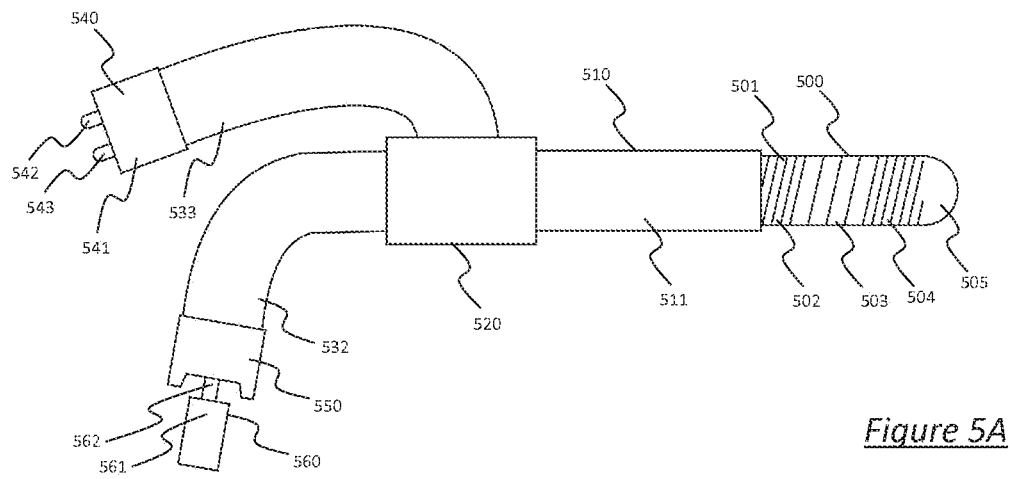
FIG. 5A is a schematic diagram showing connector in an external view a unitized injection electrode system with a flexible active tip, a flexible shaft depicted in a straight position, an injection port, a generator connector, and a moveable stylet, where the injection port and generator connector are each connected separately by means of a dedicated tube to the proximal end of the electrode.
Figure 5B:
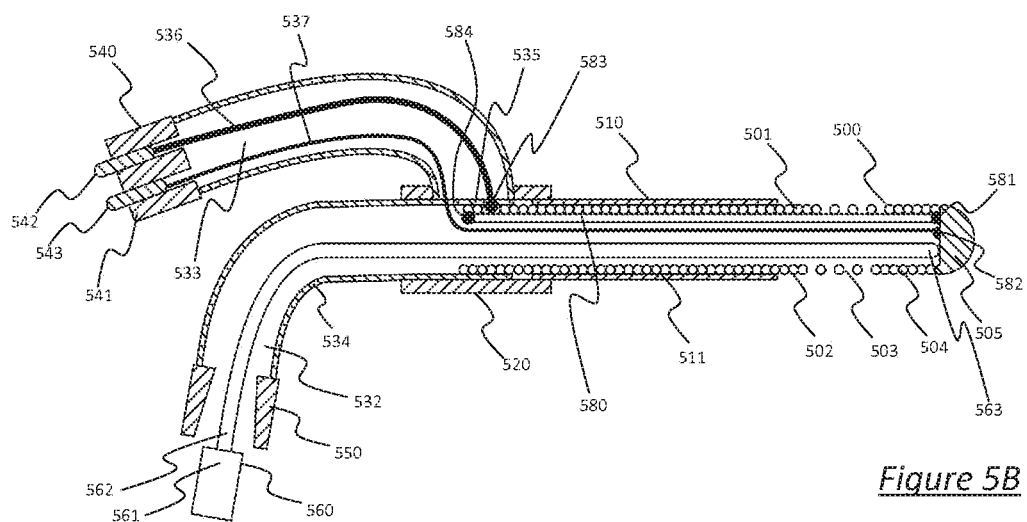
FIG. 5B is a schematic diagram showing in a sectional view a moveable stylet positioned inside a unitized injection electrode where a coil is used in the construction of the shaft and active tip, where the electrode has a temperature sensor, injection port, and a generator connector, and where the injection port and generator connector are each connected separately by means of a dedicated tube to the proximal end of the electrode.

FIG. 5 presents a unitized injection electrode with moveable stylet in accordance several aspects with the present invention. FIG. 5A shows an external view of the unitized injection electrode. FIG. 5B shows one embodiment of the internal construction of the unitized injection electrode in a cross-section view. In one embodiment, the embodiments presented in FIG. 5A and FIG. 5B are analogous to the embodiments presented in FIG. 4A and FIG. 4B, with the difference that in FIG. 5, the injection cable branch, labeled 532 in FIG. 5 and labeled 432 in FIG. 4, and the generator cable branch, labeled 533 in FIG. 5 and labeled 433 in FIG. 4, are connected directly to the hub, labeled 520 in FIG. 5 labeled 420 in FIG. 4, whereas in FIG. 4 the injection cable branch and generator cable branch connect to a root cable branch 431 that connects to the hub 420. In one embodiment, the injection electrode with moveable stylet is configured for RF therapy. In one embodiment, the injection electrode with moveable stylet is configured to be placed in the epidural space. In one embodiment, the injection electrode with moveable stylet 560 is configured for injection of fluid through the tip 500. In one embodiment, the stylet 560 can be removed from the electrode to allow for delivery of fluids from the tip 500 by means of injection into port 550. In one example, the electrode shaft 510 and tip 500 are flexible. In one embodiment, the injection electrode is configured to measure the temperature of tissue in contact with the active tip 500 of the electrode. In one embodiment, the injection electrode is configured to effect temperature-controlled radiofrequency treatment, including pulsed radiofrequency therapy, of nerves by means of placement of the electrode in the epidural space of a human patient in order to manage said patient's pain. In one embodiment, the unitized injection electrode with moveable stylet is configured to apply radiofrequency electric fields, including pulsed radiofrequency electric fields, to spinal nerves, spinal nerve roots, dorsal spinal nerve roots, and/or dorsal root ganglia, by placement of the electrode in the epidural space and/or the spinal foramina.

The distal end of the electrode is the end of the active tip 500, and the proximal end of the electrode is end of the cables 530. Electrode structures that are more distal are closer to the distal tip 505. Electrode structures that are more proximal are closer to the generator connector 540 and/or to the injection port 550. The distal end of the stylet 560 is the distal tip 563. The proximal end of the stylet 560 is the handle 561.

The unitized injection electrode has tip 500 comprising a metallic coil 501 with distal end 505, shaft 510 comprising electrical insulation 511 covering the metallic coil 501, hub 520, generator cable 533, connector 540 comprising body 541 and pins 542 and 543, injection cable 532, injection port 550, and movable stylet 560 comprising hub 561 and shaft 562. In one embodiment, elements 500, 510, 520, 533, 540, 532, and 550 are inseparably connected. In one embodiment injection tube 532 is straight. In one embodiment injection tube 532 is curved. In one embodiment injection tube 532 is flexible. In one embodiment injection tube 532 is rigid. In one embodiment generator cable 533 is flexible. In one embodiment generator cable 533 is rigid. In one embodiment, the stylet shaft 562 is a metal rod. In one embodiment, the stylet shaft 562 is a strainless steel rod. In one embodiment, the stylet shaft 562 is a nitinol rod. One advantage of a moveable stylet 560 is that the flexibility of the electrode shaft 510 and tip 500 can be adjusted by movement of the stylet 560.

In another embodiment, the injection tubing 532 can be omitted and the injection port 550 directly connected to the hub 520. In another embodiment, the generator cable 533 can be omitted and the connector 540 directly connected to the hub 520. In another embodiment, the hub 520 can be omitted, and the injection cable 532 and the generator cable 533 directly connected to the electrode shaft 510. In another embodiment, the hub 520 can be omitted, the injection tube 532 omitted, the injection port 550 directly connected to the electrode shaft 510, and the generator cable 533 directly connected to the electrode shaft 510. In another embodiment, the hub 520 can be omitted, the electrode cable 532 omitted, the injection tube 532 directly connected to the electrode shaft 510, and the generator connector 540 directly connected to the electrode shaft 510. In another embodiment, the hub 520 can be omitted, the electrode cable 532 omitted, the injection tube 532 omitted, the injection port 550 directly connected to the electrode shaft 510, and the generator connector 540 directly connected to the electrode shaft 510. In another embodiment, the injection tube 532 and the injection port 550 can be omitted, the stylet 560 can be inserted directly into the inner lumen of the coil 501, and a separate injection port, such as a tuohy-borst adaptor, can be connected to the shaft when the stylet 560 is withdrawn from electrode to provide for injection of fluid through the electrode into tissue in which the electrode tip is placed.

Referring now to FIG. 5A specifically, an external view of the electrode is shown with the stylet 560 in place within the electrode.

Referring now to FIG. 5B specifically, a cross-sectional view of one embodiment of the internal construction of the electrode is shown with the stylet 560 in place within the inner lumen of the electrode. In one embodiment, the stylet shaft 562 is configured so that when it fully inserted into the electrode, the distal tip 563 of the stylet shaft 562 contacts the inner surface of the distal tip 505 of the electrode. In another embodiment, the stylet shaft 562 is configured so that when it fully inserted into the electrode, the distal tip 563 of the stylet shaft 562 is does not contact the inner surface of the distal tip 505 of the electrode. Element 535 is configured to limit or prevent the flow of fluid into the generator cable 533. Wire 536 and 537 pass through element 535. In one embodiment, element 535 includes the wall of the injection tube 532. In one embodiment, element 535 includes glue, such as a glue plug. In one embodiment, element 535 includes the wall of the shaft insulation 511. In one embodiment, wire 537 can passes into the inner lumen of the coil 501 via its proximal end, as illustrated in FIG. 5B. In another embodiment, wire 537 can enter the inner lumen of coil 501 by passing between links of the coil 501. Pin 542 is electrically connected to wire 536, which is electrically connected to coil 501 at junction 583, which can be, for example, a weld or solder joint. In one embodiment, electrical output from a generator connected to pin 542 is conducted to the active tip 500 of the electrode via wire 536, junction 583, and coil 501. Pin 543 is electrically connected to wire 537, which is connected to the distal end 505 of the electrode at junction 582. In one embodiment, distal end 505 is a weld that incorporates the wire 537. In one embodiment, distal end 505 is a solder joint that incorporates the wire 537. In one embodiment, distal end 505 is a glue joint that connects to the wire 537. In one embodiment, wire 537 is a constantan wire, the coil 501 is stainless steel, the connection between the coil 501 and the wire 537 is a thermocouple junction, pin 542 is configured to be attached to a temperature-measurement circuit, pin 542 is configured to be attached to the same temperature-measurement circuit, and thereby the temperature of tissue in contact with the distal tip 505 of the electrode. In another embodiment, wire 537 comprises insulated constantan and copper wires whose junction 582 is a thermocouple junction, pin 543 comprises two electrically-isolated pins of which each is connected tone of the two wires comprising wire 537, said two electrically-isolated pins are configured to be connected to a temperature-measurement system, and thereby the temperature of tissue in contact with the electrode tip 500 can be measured. The safety strap 580 can connect to the distal and proximal end of the coil 501 at junctions 581 and 584, respectively. One advantage of the safety strap 580 is that it makes the shaft 510 and tip 500 more robust. In one embodiment, the safety strap 580 can be metallic, such as a stainless steel flat wire. One advantage of a metallic safety strap 580 is that it reduces the electrical impedance between the proximal and distal ends of the coil 501. One advantage of a metallic safety strap 580 is that electrical signals are conducted with less distortion from wire 536 to the active tip 500 of the electrode. In another embodiment, the safety strap 580 can be omitted. In another embodiment, the wire 537 can include elements, such as a wire, that is configured to serve as a safety strap.

Figure 6A:
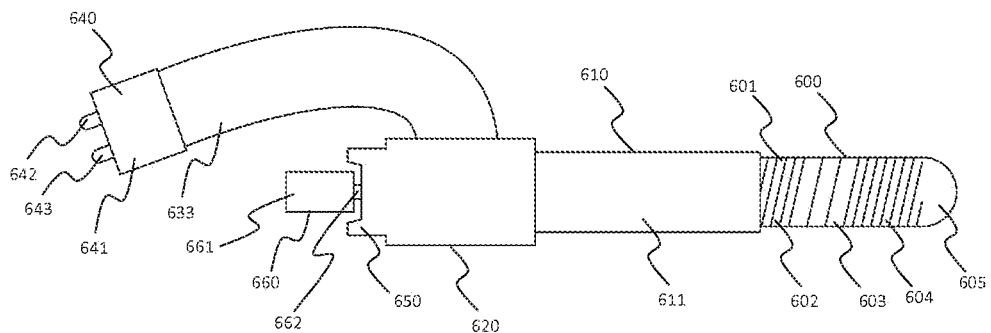
FIG. 6A is a schematic diagram showing connector in an external view a unitized injection electrode system with a flexible active tip, a flexible shaft, an injection port, a generator connector, and a moveable stylet, where the injection port is integrated into the hub at the proximal end of the electrode.
Figure 6B:
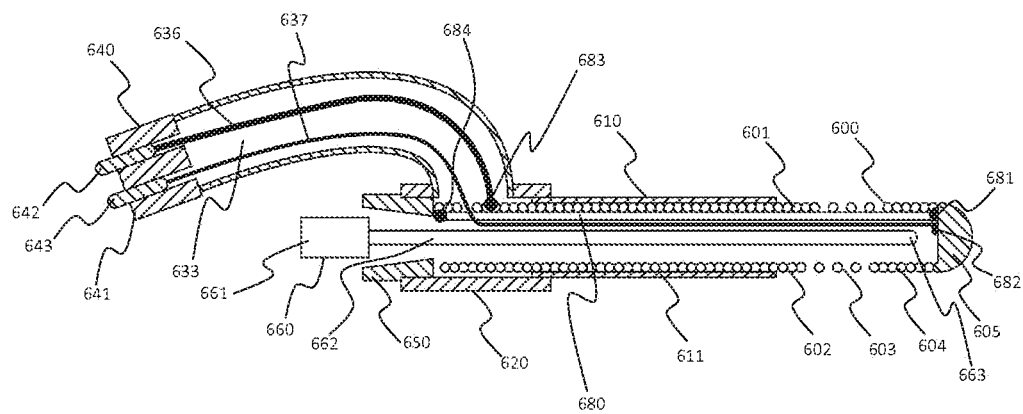
FIG. 6B is a schematic diagram showing in a sectional view a moveable stylet positioned inside a unitized injection electrode where a coil is used in the construction of the shaft and active tip, where the electrode has a temperature sensor, injection port, and a generator connector, and where the injection port is integrated into the hub at the proximal end of the electrode.

FIG. 6 presents a unitized injection electrode with moveable stylet, in accordance with several aspects of the present invention. FIG. 6A shows an external view of the unitized injection electrode. FIG. 6B shows one embodiment of the internal construction of the unitized injection electrode in a cross-section view, with the exterior of the stylet 660 shown. In one embodiment, the embodiments presented in FIG. 6A and FIG. 6B are equivalent to the embodiments presented in FIG. 5A and FIG. 5B, with the difference that the injection cable branch labeled 532 in FIG. 5 is omitted in FIG. 6, and the injection port, labeled 550 in FIG. 5 and labeled 650 in FIG. 6, is directly connected to the hub 620 in FIG. 6. One advantage of the direct connection of the injection port 650 to the hub 620 the pathway for fluid injection can be reduced.

The unitized injection electrode has tip 600 comprising a metallic coil 601 with distal end 605, shaft 610 comprising electrical insulation 611 covering the metallic coil 601, hub 620, generator cable 633, connector 640 comprising body 641 and pins 642 and 643, injection port 650, and movable stylet 660 comprising hub 661 and shaft 662. In one embodiment, elements 600, 610, 620, 633, 640, and 650 are inseparably connected. The tip 600 can have a region 603 for which the coil loops are more loosely spaced than in other regions, such as region 601 and 602.

The distal end of the electrode is the end of the active tip 600, and the proximal end of the electrode is end of the cables 630. Electrode structures that are more distal are closer to the distal tip 605. Electrode structures that are more proximal are closer to the generator connector 640 and/or to the injection port 650. The distal end of the stylet 660 is the distal tip 663. The proximal end of the stylet 660 is the handle 661.

Referring now to FIG. 6B specifically, the electrode has wire 636, wire 637, and safety strap 680. Wire 637 can be a constantan wire that connects to pin 643, and that connects to the distal end 605 of the coil 601 at junction 682 to form a thermocouple junction. Wire 637 can be a thermocouple bifilar terminated by a thermocouple junction 682 that connects to two pins composing pin 643. Pin 643 is configured to provide for monitoring of the tip temperature by connection to a temperature-measurement device. Wire 637 connects to pin 642 and to coil 601 to provide for conduction of electrical signals from a electrosurgical generator attached to pin 642 to the active tip 600 of the electrode. In embodiments where a thermocouple junction is formed between a constantan wire 637 and the distal end 605 or the coil 601, the pin 642 can connect to a temperature-measuring device to provide for monitoring of the temperature of tissue in contact with the active tip 600.

Wire 637 can enter the lumen coil 601 by passing between two loops of coil 601. In another embodiment, the wire 637 can enter the lumen of the coil 601 be passing into the proximal end of the coil 601. In another embodiment, the wire 637 can enter the inner lumen of the coil 601 at a more distal point along the shaft than pictured in FIG. 6B; an advantage of this embodiment is that the stylet shaft 662 and the wire 637 can touch each other over a shorter length. It is understood that a structure can be added to the end of the generator cable 633 where it connects to the hub 620 that is configured to limit flow of fluids into the generator cable 633, such as a glue plug.

Figure 7:
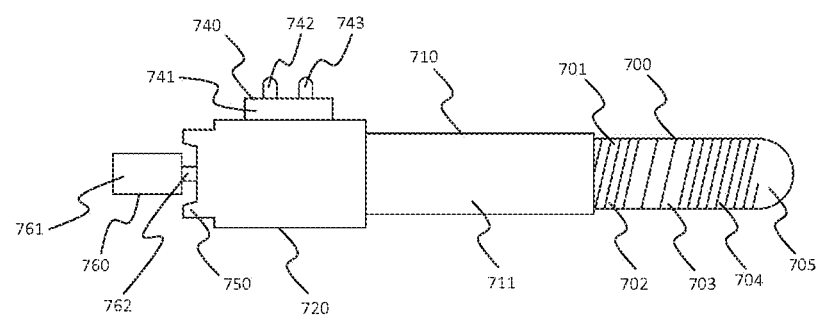
FIG. 7 is a schematic diagram showing connector in an external view a unitized injection electrode system with a flexible active tip, a flexible shaft, an injection port, a generator connector, and a moveable stylet, where the injection port and generator connector are both integrated into the hub at the proximal end of the electrode.

FIG. 7 presents a unitized injection electrode with moveable stylet in an external view, in accordance with several aspects of the present invention. In one embodiment, the embodiments presented in FIG. 7 are equivalent to the embodiments presented in FIG. 6A and FIG. 6B, with the difference that the generator cable branch labeled 633 in FIG. 6 is omitted in FIG. 7, and the injection port, labeled 650 in FIG. 6 and labeled 750 in FIG. 7, is directly connected to the hub 720 in FIG. 7. The unitized injection electrode has tip 700 comprising a metallic coil 701 with distal end 705, shaft 710 comprising electrical insulation 711 covering the metallic coil 701, hub 720, connector 740 comprising body 741 and pins 742 and 743, injection port 750, and movable stylet 760 comprising hub 761 and shaft 762. In one embodiment, elements 700, 710, 720, 740, and 750 are inseparably connected. The tip 700 can have a region 703 for which the coil loops are more loosely spaced than in other regions, such as region 701 and 702.

Figure 8A:
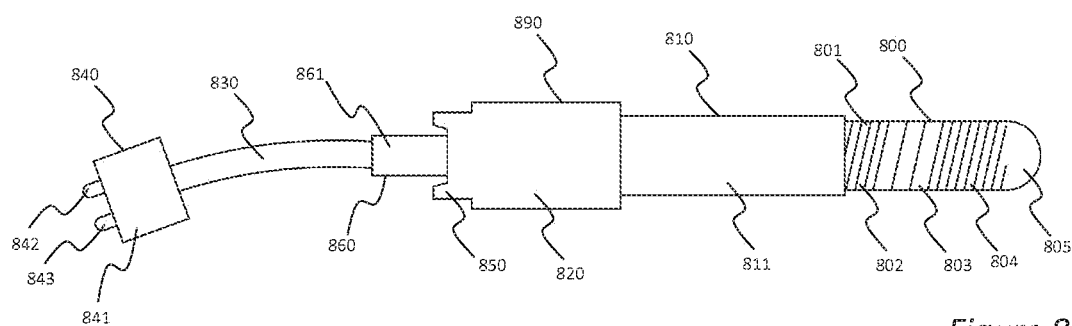
FIG. 8A is a schematic diagram showing in an external view an electrode system comprising a flexible catheter, injection hub, and stylet electrode.
Figure 8B:
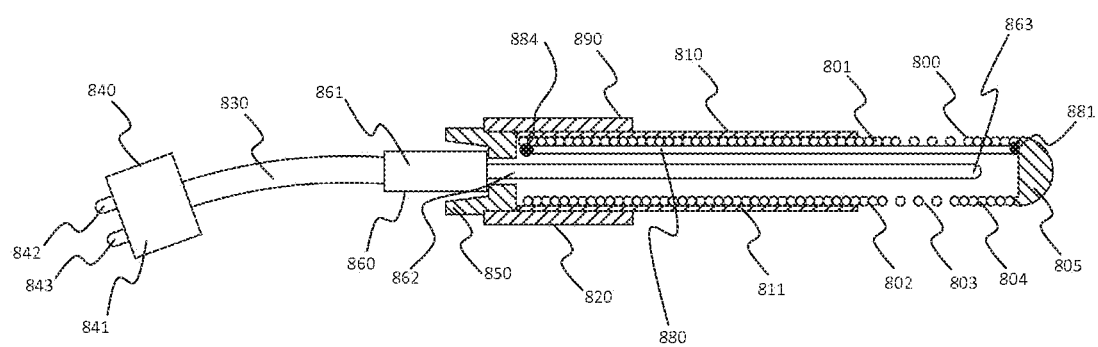
FIG. 8B is a schematic diagram showing in a sectional view an electrode system comprising a flexible catheter, injection hub, and stylet electrode.

FIG. 8 present an injection electrode system comprising a catheter 890 and separate, movable stylet electrode 860, in accordance with several aspects of the present invention. FIG. 8A presents one embodiment of the injection electrode system in an external view. FIG. 8B presents one embodiment of the internal construction of the injection electrode system, wherein the catheter 890 is shown in a cross-sectional view and the electrode 860 is shown from its exterior, positioned within the catheter 890. Referring to both FIG. 8A and FIG. 8B, the catheter 890 comprises a tip comprising coil 801 and distal end 805, shaft 810 comprising insulation 811 outside the coil 801, hub 820, and injection port 850. The electrode 860 comprises shaft 862, hub 860, cable 830, generator connector 840 comprising body 841 and pins 842 and 843. The distal end of the catheter is the end of the distal point 805, and the proximal end of the electrode is end of the hub 820. Catheter structures that are more distal are closer to the distal tip 805. Catheter structures that are more proximal are closer to the port 850. The distal end of the stylet electrode 860 is the distal tip 863. The proximal end of the stylet electrode 860 is the handle 861. In certain embodiments, the distal end 805 can be open; one advantage of an open distal end 805 is that injected fluid can exit the distal end of the catheter 890. In certain embodiments, the distal end 805 can be closed; one advantage of a closed end is that tissue cannot enter the distal end of the catheter 890.

In one embodiment, when the electrode 860 is positions within the inner lumen of the catheter 890 and electrical signals are delivered to the electrode shaft 862 by connecting the electrode to an electrical signal generator via connector 840, contact between the electrode shaft 862 and the inner surfaces of the metallic coil 801, said electrical signals are conducted to the active tip 800 of the catheter 890 and thereby delivered to tissue in contact with the active tip 800. In one embodiment, the injection electrode system in FIG. 8 can be used in the embodiments presented in FIG. 1A and FIG. 1B. The injection electrode system can provide for radiofrequency therapy by means of catheter 890 placement in the spinal canal. The injection electrode system can provide epidural anesthesia. The injection electrode system can provide stimulation-guided RF and pulsed RF treatment of nervous structures, such as the DRG, via placement of the catheter 890 within the spinal canal. The injection electrode system can provide for stimulation-guided epidural anesthesia, such a lysis of adhesions. The injection electrode system can provide for temperature-monitoring of the catheter tip 800 during medical use.

The port 850 can be integrated inseparably into the hub 820. In one embodiment, the hub 820 and injection port 850 can be inseparably connected to the shaft 810. In another embodiment, a unitized hub 820 and injection port 850 can be separable from the shaft; for example. The unitized hub 820 and injection port 850 can take the form of a tuohy-borst adaptor or another common type of injection adaptor that is familiar to one skilled in the art of epidural anesthesia. The electrode can be moveable within the catheter. The electrode can be fully removed from the catheter. The electrode can be fully removed from the catheter to provide access to the injection port 850 for the injection of fluid through the catheter and outflowing from the catheter tip 800, for example, for the purpose of effective epidural anesthesia.

In certain embodiments, the shaft 810 and tip 800 of the catheter 890 can have the same construction to the shaft and tip of electrodes presented in FIGS. 2, 3, 4, 5, 6, and 7. In one embodiment, the coil 801 can be a stainless steel spring coil of round wire. In one embodiment, the coil 801 can be a stainless steel spring coil of flat wire. In one embodiment, the coil 801 can be a laser cut stainless steel tube. It is understood that in other embodiments, the coil 801 is not present over the entire length of the shaft 810; for example, the proximal end of the coil 801 can be connected to metal tubing, such as stainless steel hypotube, to provide for a stiffer proximal part of the shaft. It is understood that multiple pieces of coil can be connected to form the coil 801. In certain embodiments, the catheter electrode system presented in FIG. 8A and FIG. 8B has the same construction and function as the injection electrode system presented in FIG. 9A and FIG. 9B.

The electrode 890 can have constructions that are familiar to one skilled in the art of RF pain management. For example, electrode 890 can have a construction similar to that of the Cosman CSK electrode. For example, electrode 890 can have a construction similar to that of the Cosman TCD electrode. For example, electrode 890 can have a construction similar to that of the Cosman TCN electrode, whose shaft includes nitinol. The electrode 890 can be a temperature-sensing electrode. The electrode 890 can have a thermocouple temperature sensor at its distal 863. The electrode 860 can be configured to provide for the delivery of radiofrequency current to the catheter 890. The connector 840 can be configured to connect to a radiofrequency generator.

Referring to FIG. 8A and FIG. 8B, the catheter 890 can be an epidural catheter. The catheter 890 can be an intravascular catheter. The catheter 890 can be configured for epidural anesthesia. The stylet electrode 860 can be configured act as a stylet for the catheter 890. The stylet electrode 860 can be configured to deliver electrical signals to the active tip 800 of the catheter 890. The stylet electrode 860 can be configured to deliver RF signals to the active tip 800 of the catheter 890. The stylet electrode 860 can be configured to deliver nerve stimulation signals to the active tip 800 of the catheter 890. The injection electrode system presented in FIG. 8 can be configured to effect radiofrequency treatment, such as pulsed radiofrequency treatment, on nerve structures by means of placement of the electrode system in the epidural space of a human body. One advantage of the injection electrode system presented in FIG. 8 is that manufacture of the electrode 860 and the catheter 890 can proceed in parallel. Another advantage of the injection electrode system presented in FIG. 8 is that standard epidural methods can be used in addition to RF methods in the same medical procedure. Another advantage of the injection electrode system presented in FIG. 8 wherein the unitized hub 820 and injection port 850 is separable from shaft 810 of the catheter 890, is that the needle used to introduce the catheter 890 can be removed from the patient while the catheter 890 is in place within the patient, by sliding said needle over the distal end of the shaft 810, as is familiar one skilled in the art of epidural anesthesia.

Referring now specifically to FIG. 8B, in one embodiment of the injection electrode system, the catheter 890 has a safety strap 880 connected to the proximal end of the coil 801 at junction 884 and to the distal end of the coil 801 at junction 881. The junction 884 can be a weld, such as a laser weld. The junction 881 can be part of the weld, such as a laser weld or an electrical discharge weld, that forms the closed end 805 of the catheter 890. The safety strap 880 can be configured to prevent the coil 801 from uncoiling during use. The safety strap can be a metal wire. The safety strap can be a flat wire. The safety strap can be configured to have a low profile to allow entry of the stylet electrode's shaft 862 into the inner lumen of the coil 801. The safety strap can be configured to have a low profile to maintain an open cross-sectional area within the inner lumen of the coil for the flow of injected and aspirated fluid. In embodiments where the safety strap 880 is a metal wire, the safety strap can improve faithful conduction of electrical signals delivered by the electrode 860 to the active tip 800 of the catheter 890. In some embodiments, the electrode shaft 862 contacts the strap 880 and thereby conducts electrical signals to the tip 800.

Referring to FIG. 8A and FIG. 8B, the length of the catheter 890 can be in the range 12-33 inches. The length of the catheter 890 can be less than 12 inches. The length of the catheter 890 can be greater than 33 inches. The length of the catheter 890 can be 12 inches. The length of the catheter 890 can 33 inches. The length of the catheter 890 can be 16 inches. The length of the catheter 890 can be 24 inches. The outer diameter of the catheter 890 can in the range 18 to 21 gauge. The outer diameter of the catheter 890 can be greater than 18 gauge. The outer diameter of the catheter 890 can be less than 21 gauge. The outer diameter of the catheter 890 can be 20 gauge. The outer diameter of the catheter 890 can be 19 gauge. The diameter of the electrode 860 can be configured to produce a desired stiffness of the assembled catheter shaft 810. The stiffness catheter shaft 810 and tip 800 can be configured to facilitate safe placement of the catheter 890 in the spinal canal. The introducer needle for the catheter can be 15 gauge. The introducer needle for the catheter can be 16 gauge. The introducer needle for the catheter can be 17 gauge. The introducer needle for the catheter can be 18 gauge. The introducer needle can be an epidural needle, such as a tuohy needle.

For embodiments where the hub 820 and injection port 850 are attached to the catheter shaft 810 (either separably as in the case where hub 820 and port 850 are an injection adaptor port, or inseparably as in the case where the hub 820 and port 850 are inseparable attached to the catheter shaft 810), the length of the electrode 860 can be configured so that when the electrode 860 is fully inserted into the catheter 890, the electrode's distal end 863 contacts the inner surface of the distal end 805 of the coil 801. One advantage of this configuration is that it provides tactile physical feedback the user that the electrode 860 is fully inserted in the catheter 890. For embodiments where the hub 820 and injection port 850 are attached to the catheter shaft 810 (either separably as in the case where hub 820 and port 850 are an injection adaptor port, or inseparably as in the case where the hub 820 and port 850 are inseparable attached to the catheter shaft 810), the length of the electrode 860 can be configured so that when the electrode 860 is fully inserted into the catheter 890, the electrode's distal end 863 cannot contact the inner surface of the distal end 805 of the coil 801. For example, as shown in FIG. 8B, the hub 861 of the electrode 860 can abut a surface of the port 850 to prevent further advancement of the electrode shaft 862 to the catheter shaft 810. One advantage of this configuration is that it ensures the distal end of the catheter 890 remains floppy irrespective of the position of the electrode 860 in the catheter 890. For embodiments where the hub 820 and injection port 850 are not attached to the catheter shaft 810 and the electrode 860 is inserted directly in the proximal end of the catheter shaft 810, the length of the electrode 860 can be configured so that when the electrode 860 is fully inserted into the catheter 890, the electrode's distal end 863 contacts the inner surface of the distal end 805 of the coil 801. One advantage of this configuration is that it provides tactile physical feedback the user that the electrode 860 is fully inserted in the catheter 890. For embodiments where the hub 820 and injection port 850 are not attached to the catheter shaft 810 and the electrode 860 is inserted directly in the proximal end of the catheter shaft 810, the length of the electrode 860 can be configured so that when the electrode 860 is fully inserted into the catheter 890, the electrode's distal end 863 cannot contact the inner surface of the distal end 805 of the coil 801. One advantage of this configuration is that it ensures the distal end of the catheter 890 remains floppy irrespective of the position of the electrode 860 in the catheter 890.

Figure 9A:
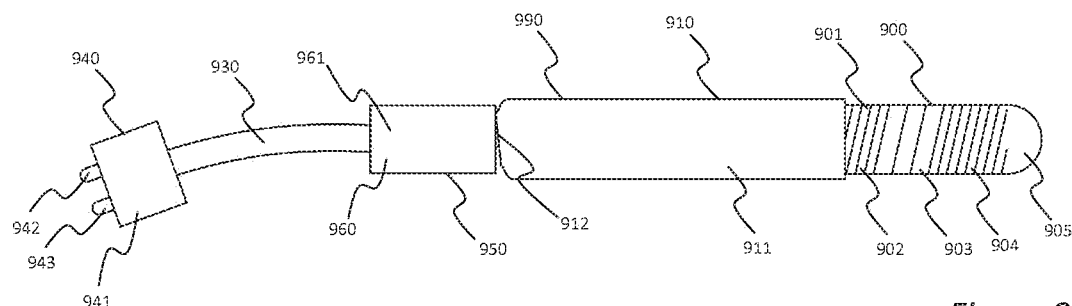
FIG. 9A is a schematic diagram showing in an external view an electrode system comprising a flexible catheter and stylet electrode.
Figure 9B:
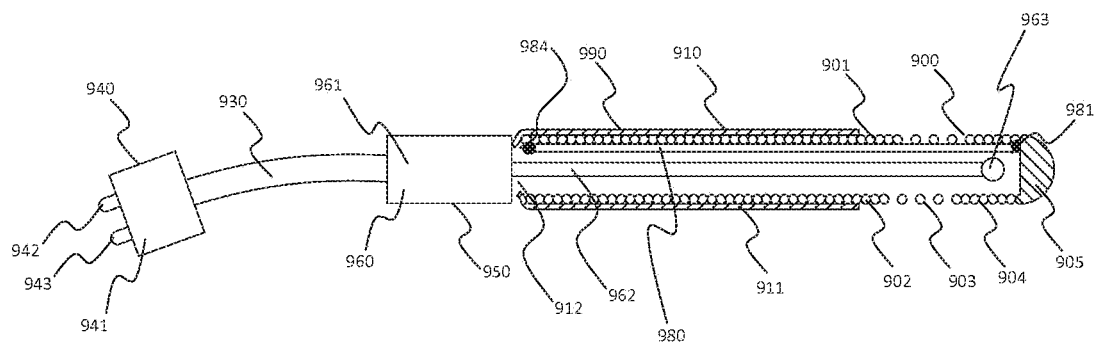
FIG. 9B is a schematic diagram showing in a sectional view an electrode system comprising a flexible catheter and stylet electrode.

FIG. 9 presents a catheter electrode system comprising a catheter 990 and separate, movable stylet electrode 960, in accordance with several aspects of the present invention. The stylet electrode 960 is inserted into an opening at the proximal end 912 of the catheter 990. FIG. 9A presents one embodiment of the injection electrode system in an external view. FIG. 9B presents one embodiment of the internal construction of the injection electrode system, wherein the catheter 990 is shown in a cross-sectional view and the electrode 960 is shown from its exterior, positioned within the catheter 990. Referring to both FIG. 9A and FIG. 9B, the catheter 990 comprises a tip comprising coil 901 and distal end 905, a proximal end 912, and a shaft 910 comprising insulation 911 outside the coil 901. The electrode 960 comprises shaft 962, hub 960, cable 930, generator connector 940 comprising body 941 and pins 942 and 943. In certain embodiments, the electrode 960 can be fully withdrawn from the catheter 990. The distal end of the catheter 990 is the end of the distal point 905, and the proximal end of the catheter 990 is end into which the electrode 960 can be inserted. Catheter structures that are more distal are closer to the distal tip 905. Catheter structures that are more proximal are closer to the end into which the electrode 960 can be inserted. The distal end of the stylet electrode 960 is the distal tip 963. The proximal end of the stylet electrode 960 is the handle 961. In certain embodiments, the distal end 905 can be open; one advantage of an open distal end 905 is that injected fluid can exit the distal end of the catheter 990. In certain embodiments, the distal end 905 can be closed; one advantage of a closed end is that tissue cannot end the distal end of the catheter 990.

In one embodiment, the distal tip 963 of the stylet is enlarged to reduce the likelihood that the stylet 960 will exit the inner lumen of the coil 901 by passing between adjacent loops of the coil 901, such as the spaces of the open coil section 903, for example when the stylet 960 is moved and the catheter's tip 900 is in a bent conformation. In one embodiment, the enlarged distal stylet tip 963 is substantially spherical. In another embodiment, the enlarged distal stylet tip 963 has other shapes matched to the physical characteristics of the coil and physican needs. It is understood that an enlarged distal stylet tip can be used for other embodiments that include a moveable stylet, including these presented in FIGS. 4, 5, 6, 7, 8, 10, and 11.

In one embodiment, the system presented in FIG. 9 contains more than one stylet 960. In one more specific embodiment, one stylet is an electrode and another stylet is a conventional catheter stylet consisting of a rod and a handle. In another more specific embodiment, the said more than one stylet have distinguishing physical characteristics, including without limitation differing lengths, differing stiffnesses, and differing shapes. In certain embodiments, the catheter 990 is configured such that two stylets can be placed in its inner lumen at the same time. In certain embodiments, the catheter 990 is configured such that a straight stylet and a curved stylet can be inserted into the catheter 990 at the same time; one advantage of these embodiments is that the tip of the catheter 990 can be steered by moving the two stylets relative to the catheter 990 and to each other.

In certain embodiments, the catheter electrode system presented in FIG. 9A and FIG. 9B has the same construction and function as the injection electrode system presented in FIG. 8A and FIG. 8B. In certain embodiments, the construction and function of the system presented in FIG. 9 is the same as that presented in FIG. 8 with the difference that the hub 820 and port 850 are not explicitly shown in FIG. 9. It is understood that in certain embodiments, an injection adaptor, for instance a tuohy-borst adaptor or removable injection hub, such as 820 and 850, can be attached to the proximal end 912 of the catheter 990 to provide for injection of fluids. In one embodiment, the catheter 990 is an epidural catheter, familiar to one skilled in the art of epidural anesthesia. In one embodiment, the catheter 990 is an epidural catheter constructed using a metal coil. In one embodiment, the electrode 960 is a radiofrequency electrode configured to move through the inner lumen of the catheter 990. In one embodiment, the electrode 960 is configured to deliver electrical signals, such as radiofrequency, pulsed radiofrequency, and stimulation signals, to the active tip 900 of the catheter. In one embodiment, electrical signals delivered to the electrode 960 by connection of its generator connector 940 to an electrical generator, are in turn conducted to the active tip 900 of catheter 990 by contact between the electrode shaft 962 with the inner surface of the coil 901.

Referring now specifically to FIG. 9B, in one embodiment of the injection electrode system, the catheter 990 has a safety strap 980 connected to the proximal end of the coil 901 at junction 984 and to the distal end of the coil 901 at junction 981. The junction 984 can be a weld, such as a laser weld. The junction 981 can be part of the weld, such as a laser weld or an electrical discharge weld, that forms the closed end 905 of the catheter 990. The safety strap 980 can be configured to prevent the coil 901 from uncoiling during use. The safety strap can be a metal wire. The safety strap can be a flat wire. The safety strap can be configured to have a low profile to allow entry of the stylet electrode's shaft 962 into the inner lumen of the coil 901. The safety strap can be configured to have a low profile to maintain an open cross-sectional area within the inner lumen of the coil for the flow of injected and aspirated fluid. In embodiments where the safety strap 980 is a metal wire, the safety strap can improve faithful conduction of electrical signals delivered by the electrode 960 to the active tip 900 of the catheter 990. In some embodiments, the electrode shaft 962 contact the strap 980 and thereby electrical signals are conducted to the tip 900; one advantage of the safety strap is that the distal end of the electrode 963 does not need to touch the catheter tip 905 in order that electrical signals are conducted to the tip 900. In one embodiment, the electrode 960 can be long enough that its distal end 963 contacts the inner distal surface 905 of the catheter 990 when it is fully inserted into the catheter 990. In one embodiment, the electrode 960 is configured such that its distal end 963 does not contact the inner surface of the distal end 905 of the catheter 990, when the electrode 960 is fully inserted into the catheter 990. For example, as shown in FIG. 9B, the hub 961 of the electrode 960 can be constructed to abut the proximal end of the catheter 890 and thereby prevent the distal end 963 of the electrode shaft 962 from contacting the distal end of the inner lumen of the coil 901.

Referring now to FIGS. 10A, 10B, 10C, 10D, and 10E, FIG. 10 presents certain embodiments of a system that includes a catheter 1015, an injection adaptor 1020, a stylet 1080, and an electrode 1060, in accordance with several aspects of the present invention. The catheter 1015 includes proximal end 1012, shaft 1010, plastic sheath 1011, tip 1001, spring coil 1001, proximal aspect 1002 of the tip 1000, middle aspect 1003 of the tip 1000, distal aspect 1004 of the tip 1000, and distal end 1005. The injection adaptor 1020 includes proximal port 1032, a proximal clamp 1031, a middle body 1043, an injection port 1042, a distal clamp 1041, distal body 1051, and distal port 1052. The stylet 1080 includes proximal handle 1081, shaft 1082, and distal tip 1083. The electrode 1060 includes proximal hub 1061, shaft 1062, distal tip 1063, cable 1064, and generator connector 1065. The generator connector 1065 includes body 1066, output connection 1067, and temperature connection 1068.

In certain embodiments, the catheter 1015 is an epidural catheter. In certain embodiments, the catheter 1015 is an intravascular catheter. In certain embodiments, the catheter 1015 is an intraurethral catheter. In certain embodiments, the plastic sheath 1011 is electrical insulation. In certain embodiments, the spring coil is a stainless steel spring coil. In certain embodiments, the distal end 1005 is a closed end. In certain embodiments, the distal end 1005 includes an opening. The catheter tip 1000 can include openings, for example on the middle aspect of the tip 1003, configured for outflow of fluid from the inner lumen of the catheter 1015. In certain embodiments, the catheter 1015 can have a maximum external diameter of 0.042 inches. In certain embodiments, the tip 1000 of the catheter 1015 has a maximum diameter of 0.034 inches. In certain embodiments, the tip 1000 of the catheter 1015 has a length in the range 0-20 mm. In certain embodiments, the catheter 1015 is one of the embodiments of catheter 890. In certain embodiments, the catheter 1015 is one of the embodiments of the catheter embodiments described in relation to FIG. 8. In certain embodiments, the catheter 1015 is one of the embodiments of catheter 990. In certain embodiments, the catheter 1015 is one of the embodiments of the catheter embodiments described in relation to FIG. 9.

In certain embodiments, port 1042 can accept a syringe. In certain embodiments, the injection port 1042 can include a luer port. Injection port 1042 can include a luer lock. Injection port 1042 can be a male luer. Injection port 1042 can include a flexible tube and a luer port. Port 1032 can be a luer port. In certain embodiments, the injection adaptor 1020 can have dimensions similar to a tuohy-borst adaptor for guidewires. In certain embodiments, the clamp 1031 is a tuohy-borst adaptor. In certain embodiments, the clamp 1031 includes a tube and block, wherein the block includes a slot with narrowing cross section that is configured to close down the tube when the block is relative to the tube. In certain embodiments, the clamp 1031 can provide for the repeated attachment and separation of the adaptor 1020 and the electrode 1060. In certain embodiments, the clamp 1031 can provide for the repeated attachment and separation of the adaptor 1020 and the stylet 1080. In certain embodiments, the clamp 1041 is a tuohy-borst adaptor. In certain embodiments, the clamp 1041 includes a tube and block, wherein the block includes a slot with narrowing cross section that is configured to close down the tube when the block is relative to the tube. In certain embodiments, the clamp 1041 can provide for the repeated attachment and separation of the adaptor 1020 and the catheter 1015.

In certain embodiments, the electrode 1060 includes a temperature sensor, for example in its distal end 1063, and temperature connection 1068 conducts temperature signals from the temperature sensor. In certain embodiments, the electrode does not include a temperature sensor and does not include a temperature connection 1068. In certain embodiments, the electrode 1060 is an RF electrode. In certain embodiments, the electrode is a temperature-sensing RF electrode. In certain embodiments, the electrode is an internally-cooled RF electrode. In certain embodiments, the electrode 1060 is a unitized injection electrode. In certain embodiments, the electrode 1060, the electrode 1060 includes an injection port configured such that when fluid is injected into the electrode's injection port, that fluid flows into the catheter's inner lumen. In certain embodiments, the electrode shaft 1062 has an outer diameter 0.014 inches. The shaft 1062 of the electrode 1060 can be composed of a conductive metal, for example, stainless steel or nitinol. The distal end 1063 of the electrode 1060 can have an outer diameter larger than the outer diameter of the shaft 1062; one advantage of an enlarged distal end 1063 is that the electrode is less likely to exit the inner lumen of the catheter 1015 through fluid-outflow holes in the catheter 1015, particularly when the catheter is in a curved configuration within a living body and the electrode 1060 is moved relative to the catheter 1015. In another embodiment, the distal end 1063 of the electrode 1060 can have the same outer diameter as the shaft 1062.

In certain embodiments, the stylet 1080 includes a RF generator connection in its handle 1081. In certain embodiments, the electrode shaft 1082 has an outer diameter in the range 0.008 to 0.014 inches. In certain embodiments, the shaft 1080 is a metal rod, such as a stainless steel rod or a nitinol rod. The distal end 1083 of the stylet 1080 can have an outer diameter larger than the outer diameter of the shaft 1082; one advantage of an enlarged distal end 1083 is that the stylet is less likely to exit the inner lumen of the catheter 1015 through fluid-outflow holes in the catheter 1015, particularly when the catheter is in a curved configuration within a living body and the stylet 1080 is moved relative to the catheter 1015. In another embodiment, the distal end 1083 of the stylet 1080 can have the same outer diameter as the shaft 1082. In certain embodiments, the stylet 1080 can include an injection port in the hub 1081 and a shaft 1082 that includes a hollow lumen and one or more openings in its distal end 1083; one advantage of these embodiments is that fluid injection into the catheter can be effected via the stylet 1080.

Figure 10A:
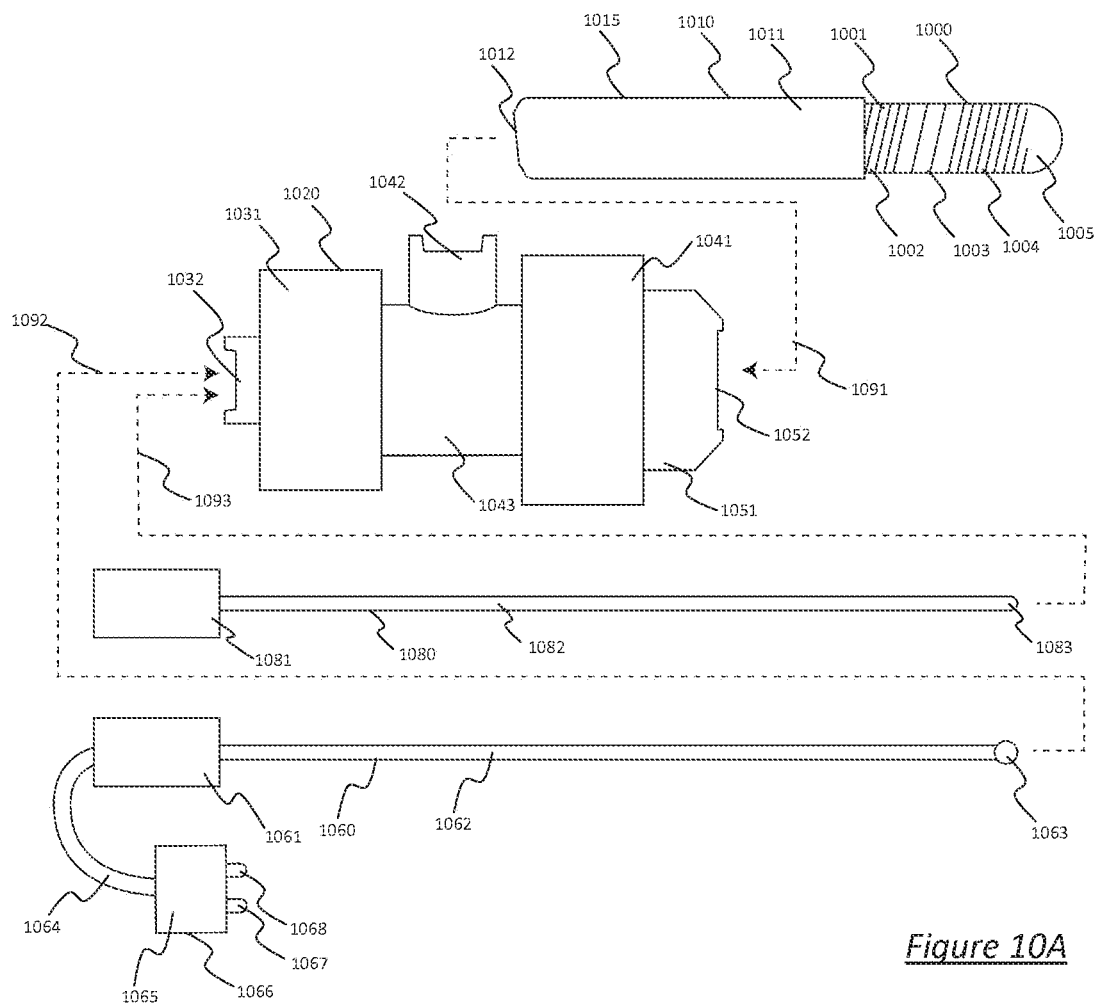
FIG. 10A is a schematic diagram showing an injection catheter system in an external view, wherein the injection catheter system includes a catheter, an injection adaptor hub, a stylet, and a stylet electrode, and wherein the injection adaptor hub includes a fluid clamp for the catheter, a fluid clamp for the electrode and stylet, and an injection port.

Referring now specifically to FIG. 10A, the catheter 1015, electrode 1060, and hub adaptor 1020 are shown in external views. The catheter 1015 can be inserted into port 1052 as shown by arrow 1091, and clamp 1041 can be actuated to fix the injection adaptor to the catheter. The clamp 1041 can provide a fluid seal between the catheter 1015 and the injection adaptor 1020, so that, for example, fluid injected into the injection adaptor 1020 does not leak from the distal port 1052 when the catheter is clamped inside the port 1052. In certain embodiments, the clamp 1041 can be released non-destructively so that the injection adaptor 1020 can be separated from the catheter; one advantage of a separable injection adaptor 1020 is that if the catheter has been introduced into the living body by means of a metal tube, such as the metal tube an epidural needle, the needle can be removed from the living body by sliding the needle off of the proximal end, even if the catheter is still placed in the living body. The catheter stylet 1080 can be inserted into port 1032 as shown by arrow 1093, and clamp 1031 can be actuated to fix the stylet 1080 to the injection adaptor 1020. The clamp 1031 can provide a fluid seal between the stylet 1060 and the injection adaptor 1020; one advantage of this fluid seal is that fluid injected into the adaptor 1020 is prevented from leaking out of port 1032. When the catheter 1015 is placed inside the distal port 1052, the stylet 1080 can pass through the injection adaptor from port 1032 and out of port 1052 into the inner lumen of the catheter 1015. The clamp 1031 can be released non-destructively to release the stylet 1080 from the adapator 1020, thereby allowing the stylet 1080 to move freely into the injection adaptor 1020 and the catheter 1015 and to be removed from the injection adaptor 1020 and catheter 1015. The electrode 1060 can be inserted into port 1032 as shown by arrow 1093, and clamp 1031 can be actuated to fix the electrode 1060 to the injection adaptor 1020. The clamp 1031 can provide a fluid seal between the electrode 1080 and the injection adaptor 1020; one advantage of this fluid seal is that fluid injected into the adaptor 1020 is prevented from leaking out of port 1032. When the catheter 1015 is inserted into port 1052, the electrode 1060 can pass through the hub adaptor 1020 and into the inner lumen of the catheter 1015. The clamp 1031 can be released to release the electrode 1060 from the adapator 1020, thereby allowing it to move freely into the injection adaptor 1020 and the catheter 1015, and to be removed from the injection adaptor 1020 and catheter 1015.

Figure 10B:
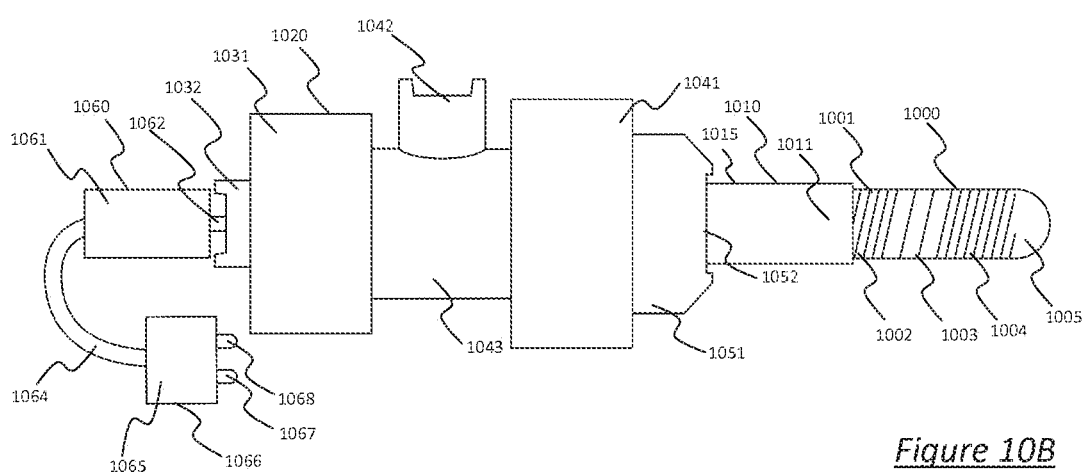
FIG. 10B is a schematic diagram showing an assembled injection catheter system in an external view, wherein the injection catheter system includes a catheter, an injection adaptor hub, a stylet, and a stylet electrode, and wherein the injection adaptor hub includes a fluid clamp for the catheter, a fluid clamp for the stylet or stylet electrode, and an injection port.

Referring now specifically to FIG. 10B, one embodiment of an assembly of the catheter 1015, the injection adaptor 1020, and the electrode 1060 is presented in an external view. The proximal end of the catheter 1015 is clamped in the distal opening 1052 of the injection adaptor 1020, thereby effecting a fluid seal between an outer surface of the catheter 1015 and an inner surface of the adaptor 1020. The electrode 1060 is clamped in the proximal opening 1032 of the injection port 1020, thereby creating a fluid seal between an outer surface of the electrode 1060 and an inner surface of the adaptor 1020. In certain embodiments, a mark is provided on the shaft of the catheter to indicate the proper positioning of the catheter 1015 within the adaptor 1020. In certain embodiments, the adaptor 1020 includes a stop within the opening 1052 that is configured to engage with the catheter 1015, thereby indicating the proper position of the the catheter 1015 within the hub 1020. The shaft 1062 of the electrode 1060 passes through an inner lumen of the adaptor 1020 and into the inner lumen of the catheter 1015. In certain embodiments, the distal end 1063 of the electrode 1060 is mechanically prevented from touching a distal surface 1005 of the catheter 1015, if present, for example, by means of mechanical engagement of the electrode hub 1061 and the port 1032. In certain embodiments, the distal end of the electrode 1063 can touch the distal end of the catheter 1015, if present. In certain embodiments, the adaptor hub provides a fluid pathway between port 1042 and the inner lumen of catheter 1015. One advantage of said fluid pathway is that fluid injected into port 1042 can flow into the catheter 1015 and out of holes in either the shaft 1010, the tip 1000, or both. One advantage of the two fluid clamps 1031 and 1041 is that fluid injected into port 1042 does not leak out of ports 1032 and 1052. One advantage of the two fluid clamps 1031 and 1041 is that fluid, such as anesthetic, radiocontrast, alcohol, biological material, and drugs, can be injected into port 1042 when the electrode 1060 is positioned in the inner lumen of catheter 1015 without said fluid leaking out of the electrode port 1032 and the catheter port 1052. In certain embodiments, the internal construction of the assembly shown in FIG. 10B is that of the assembly shown in FIG. 10D.

Figure 10C:
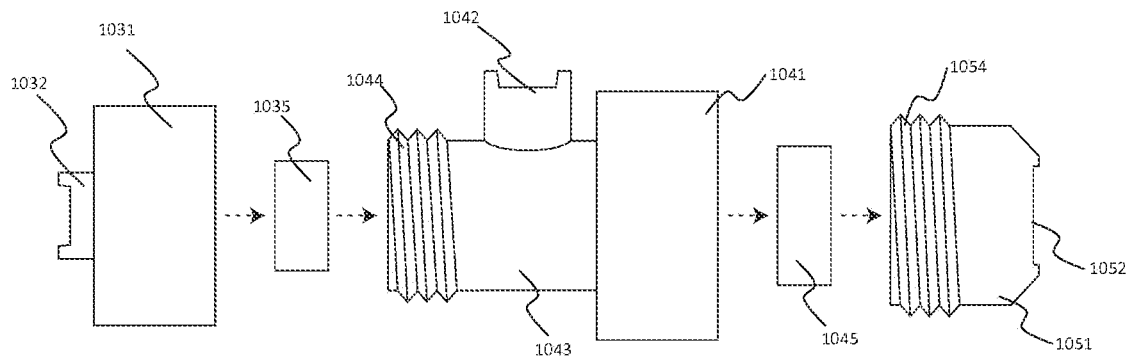
FIG. 10C is a schematic diagram showing the construction of an injection adaptor hub for a catheter that includes a fluid clamp for a catheter, a fluid clamp for a stylet, and an injection port.
Figure 10D:
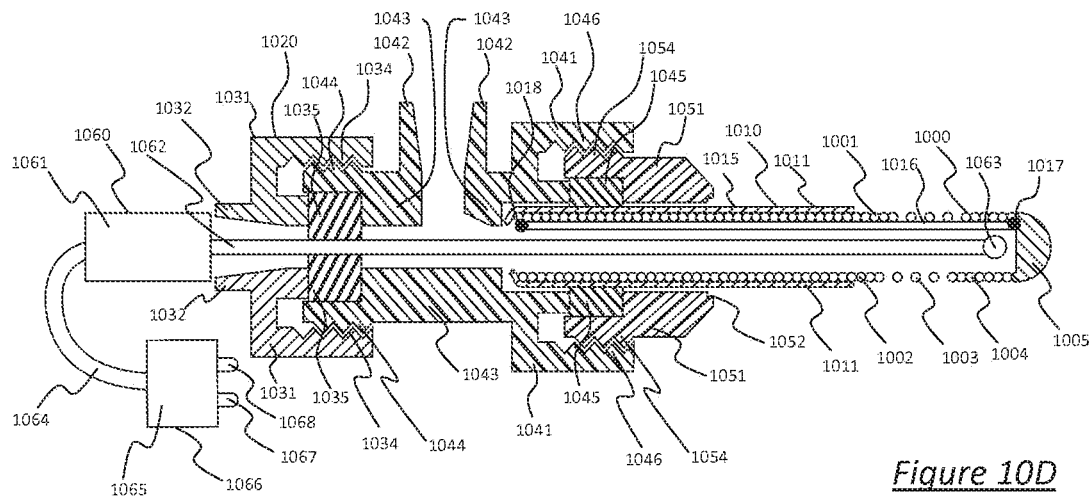
FIG. 10D is a schematic diagram showing an injection catheter system in an cross-sectional view, wherein the injection catheter system includes a catheter, an injection adaptor hub, and a stylet electrode including a flexible cable, and wherein the injection adaptor hub includes a fluid clamp for the catheter, a fluid clamp for the stylet electrode, and an injection port.
Figure 10E:
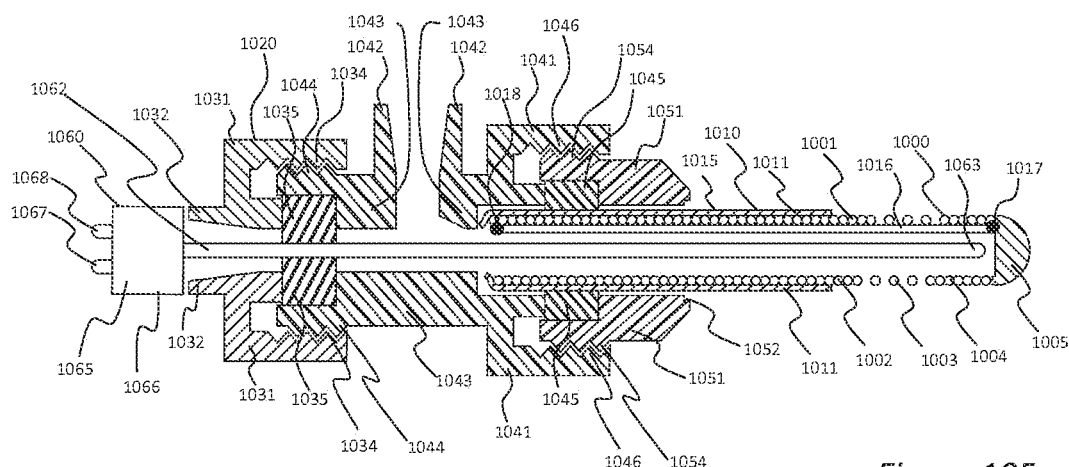
FIG. 10E is a schematic diagram showing an injection catheter system in an cross-sectional view, wherein the injection catheter system includes a catheter, an injection adaptor hub, and a stylet electrode including a handle configured to connect to an electrical generator, and wherein the injection adaptor hub includes a fluid clamp for the catheter, a fluid clamp for the stylet electrode, and an injection port.

Referring now specifically to FIGS. 10C, 10D, and 10E, one embodiment of the construction of injection adaptor hub 1020 is presented. In FIG. 10C, the adaptor 1020 is presented in an exploded, external view. In FIGS. 10D and 10E, the adaptor 1020 and the catheter are each presented in a cross sectional view, and the electrode 1060 is presented in an external view. In this embodiment, the injection adaptor 1032 includes five pieces. The first piece includes port 1032, proximal clamp 1031, and internal threads 1034, and a central through hole, all of which can be composed of a single piece of a hard material, such as a hard plastic, ABS, PVC, polycarbonate, or a metal. The second piece 1035 is a compressible ring, which can be composed of a soft plastic such as polyurethane. The third piece includes the external threads 1044, a middle body 1043, injection port 1042, distal clamp ring 1041, and a central through hole. The fourth piece is a compressive ring, which can be composed of a soft plastic such as polyurethane. The fifth piece is a distal body 1051 that includes external threads 1054, distal port 1052, and a central through hole. As is familiar to those skilled in the art of tuohy-borst adaptors, when ring 1031 is tightened onto middle body 1043 by engagement of threads 1034 and 1044, the gasket 1035 is compressed and the diameter of the central through hole of gasket 1035 is reduced. The gasket 1035 can be configured such that when the electrode 1060 passes through the gasket 1035 and the gasket is compressed between ring 1031 and body 1043, the gasket compresses the electrode shaft 1062 thereby creating a fluid seal among the ring 1031, the ring 1015, and the shaft 1062. As is familiar to those skilled in the art of tuohy-borst adaptors, when ring 1041 is tightened onto distal body 1051 by engagement of threads 1046 and 1054, the gasket 1045 is compressed and the diameter of the central through hole of gasket 1045 is reduced. The gasket 1045 can be configured such that when the catheter 1015 passes through the gasket 1045 and the gasket is compressed between ring 1041 and body 1051, the gasket compresses the catheter shaft 1010 thereby creating a fluid seal among the ring 1041, ring 1045, and ring 1051. When gaskets 1035 and 1045 are both compressed to create two fluid seal, fluid injected into port 1042 flows into the inner lumen of the injection adaptor 1020, into the inner lumen of the catheter 1015, and out from gaps 1003 in the spring coil 1001 of the tip 1000. One advantage of the electrode catheter system presented in FIG. 10 is that fluid can be injected into a living body through the catheter while the electrode 1060 is positioned in the inner lumen of the catheter 1015. One advantage of the embodiments of an injection adaptor 1020 presented in FIG. 10 is that fluid can be injected into a living body through a catheter 1015 while the catheter's stylet 1080 is positioned in the inner lumen of the catheter 1015. One advantage of the embodiments of an injection adaptor 1020 presented in FIG. 10 is that an electrode 1080 or a stylet 1060 can pass straight through the adaptor 1020 and into the catheter.

In certain embodiments of the injection adaptor 1020, the ring 1031 and the injection port can be separate pieces; for example, the 1031 can be rotate about its central axis relative to the port 1032. In certain embodiments of the injection adaptor 1020, the ring 1041 can be separate pieces; for example, the 1041 can be rotate about its central axis relative to the middle body 1043. In certain embodiments, the ring 1031 and middle body 1043 are a single solid piece, and the inner diameter of the ring 1035 and the outer diameter of the electrode shaft 1062 are configured such a fluid seal is created when the electrode shaft 1062 passes through the inner lumen of the ring 1035; for example, the inner diameter of the ring 1035 can be slightly smaller than the outer diameter of the electrode shaft 1062 so that the electrode shaft 1062 compresses the ring 1035 when the electrode 1062 passes through the ring 1035. In certain embodiments, the ring 1041 and distal body 1051 are a single solid piece, and the inner diameter of the ring 1045 and the outer diameter of the catheter shaft 1010 are configured such a fluid seal is created when the catheter shaft 1010 passes through the inner lumen of the ring 1045; for example, the inner diameter of the ring 1045 can be slightly smaller than the outer diameter of the catheter shaft 1010 so that the catheter shaft 1010 compresses the ring 1045 when the catheter shaft 1010 passes through the ring 1045. In certain embodiments of the injection adaptor hub 1020, the adaptor 1020 is constructed by connecting a two touhy-borst adaptors and one T-shaped tube, wherein the first touhy-borst adaptor has a male luer-lock its distal end, the first touhy-borst adaptor distal end is attached to the female luer-lock port at the proximal end of the T-shaped tube, the T-shaped tube has a side port for injection of fluid, the distal end of the T-shaped tube has a male luer-lock, the distal end of the T-shaped tube is attached to the female luer-lock of the cap of the second touhy-borst adaptor, the first touhy-borst adaptor is configured to create a fluid seal around an electrode 1060 or stylet 1080 passing through the first touhy-borst adaptor's center lumen, and the second touhy-borst adaptor is configured to create a fluid seal around a catheter 1015 passing into its distal opening 1052; in one more specific embodiment, the said two tuohy-borst adaptors and one T-shaped tube are standard guidewire components. In other embodiment, a Y-shaped tube replaces the said T-shaped tube. In other embodiments, at least one of the fluid clamps in adaptor 1020 is not a touhy-borst adaptor. In another embodiment, both fluid clamps in adaptor 1020 are not touhy-borst-type clamps. In other embodiments, a fluid clamp in adaptor 1020 can be a structure that pinches a tube around the electrode 1060 or the stylet 1080 passing through the tube. In another embodiment, at least one fluid clamp in adaptor 1020 can be an annular structure whose inner diameter is interferes with the object passing through it. In another embodiment of in adaptor 1020, the fluid clamp around the stylet 1080 or electrode 1060 can be a plastic ring whose inner diameter is equal to or smaller than the stylet's outer diameter, so that the stylet can be moved through the ring and fluid is substantially restrained from passing between the ring and the stylet. In other embodiments, the injection port 1042 can include a fluid clamp.

Referring now specifically to FIG. 10D, one embodiment of an assembled catheter electrode system is presented that includes a catheter 1015, a separable hub 1020, and an electrode 1060, wherein the catheter 1015 and adaptor 1020 are shown in a cross-sectional view, and the electrode 1060 is shown in an external view. In certain embodiments, the system can be configured for application of radiofrequency therapy, such as pulsed radiofrequency therapy, to nerve in the epidural space.

Referring now specifically to FIG. 10E, one embodiment of an assembled catheter electrode system is presented that includes a catheter 1015, a separable injection hub 1020, and an electrode 1060, in which the electrode 1060 includes a generator connector 1066 that is directly attached to the shaft 1062. In one embodiment, the generator connector hub 1066 only contains one pin 1067 for connection to an electrical signal, such as the output of an RF generator or the output of a nerve stimulator. One advantage of a coaxial generator connector 1066 is that the connector can be used to manipulate the electrodes 1060.

In other embodiments of FIGS. 10B, 10D, and 10E, the stylet 1080 can replace the electrode 1060 in the assembly.

Referring to FIG. 10, in certain embodiments, catheter 1015 does not include a spring coil. In certain embodiments, the catheter 1015 is a plastic catheter. In certain embodiments, the catheter 1015 has an open distal end 1005. In certain embodiments, the catheter includes one or more holes on the side of its shaft or tip to provide for the outflow of injected fluid. In certain embodiments, the spring coil 1001 is completely covered by the insulation 1011. In certain embodiments, the catheter 1015 has an exterior surface that is entirely plastic and a closed distal end. In certain embodiments, the catheter 1015 can be steerable. In certain embodiments the catheter 1015 can include a connection to an RF generator. In certain embodiments, the catheter can be a unitized catheter injection electrode. In certain embodiments, the injection hub 1020 can be inseparably connector the catheter 1015.

Referring to FIG. 10, in certain embodiments, the system includes only the catheter 1015, the electrode 1060, and the injection adaptor 1020, and does not include a stylet 1080. In certain embodiments, the system includes only the catheter 1015, the stylet 1080, and the injection adaptor 1020, and does not include an electrode 1060. In certain embodiments, the injection adaptor 1020 is provided separately. In certain embodiments, the injection adaptor 1020 is configured to be adapted to a variety of catheters. In certain embodiments, a standard epidural needle can be included in the system and used to penetrate tissue, such as the skin, to provide for introduction of the catheter 1015 into the human body. In certain embodiments, an epidural needle that includes electrical insulation covering a part of its shaft can be included in the system and used to penetrate tissue, such as the skin, to provide for introduction of the catheter 1015 into the human body. In certain embodiments, and RF generator can be included in the system.

Referring now to FIGS. 11A, 11B, 11C, 11D, 11E, and 11F, FIG. 11 presents certain embodiments of a system that includes a catheter 1115, an injection adaptor 1120, and an injection stylet 1180, in accordance with several aspects of the present invention. The catheter 1115 includes proximal end 1112, shaft 1111, plastic sheath 1111, tip 1101, spring coil 1101, proximal aspect 1102 of the tip 1100, middle aspect 1103 of the tip 1100, distal aspect 1104 of the tip 1100, and distal end 1105. The injection adaptor 1120 includes proximal port 1132, a proximal clamp 1131, a middle body 1143, an injection port 1142, a distal clamp 1141, distal body 1151, and distal port 1152. The injection stylet 1180 includes an injection port 1184, proximal handle 1181, injection tube 1185, shaft 1182, distal tip 1183. In certain embodiments, the injection adaptor can be one of the embodiments of an injection adaptor 1020 presented in relation to FIG. 10, wherein the injection port 1042 is omitted. In certain embodiments, the injection adaptor can be one of the embodiments of an injection adaptor 1020 presented in relation to FIG. 10, wherein the middle body 1043 is a tubular structure that does not have a hole in one of its side walls. In certain embodiments the catheter 1115 can be one of the embodiments of catheter 1015 presented in relation to FIG. 10. In certain embodiments the stylet 1180 can be one of the embodiments of stylet 1080 presented in relation to FIG. 10. In certain embodiments the stylet 1180 can be one of the embodiments of an electrode 1060 presented in relation to FIG. 10.

The proximal port 1132 can be a female luer port. The proximal port 1132 can configured to admit the injection tube 1185 and the shaft 1182. The proximal clamp 1131 can be a tuohy-borst type port. The proximal clamp 1131 can be configured to create a fluid seal around the injection tube 1185 when the tube 1185 is inserted into the port 1132. The middle body 1143 is a tubular structure that includes a central lumen through which the shaft 1182 can pass. The distal clamp 1141 can be configured to create a fluid seal around the proximal end of the catheter 1112. The distal clamp 1141 can be a tuohy-borst-type clamp. The distal body 1151 has a distal opening 1152 that into which the catheter's proximal end can enter. The stylet shaft 1182 can pass into the port 1132, through the middle body 1143, and into an inner lumen of a catheter 1115 that inserted in port 1152. In certain embodiments, the injection tube 1185 can pass into the middle body. In certain embodiments, the tube 1185 can pass through the middle body. In certain embodiments, the tube 1185 can pass through the injection adaptor and into the inner lumen of the catheter.

The port 1184 can be a female luer port. The port 1184 can be a male luer. The port 1184 can be a port configured for the injection of fluids. The port 1184 can include a luer lock. The port 1184 can be a non-luer port. The port 1184 can include a flexible extension tube. The injection tube 1185 has an inner lumen through which fluids can be injected. The injection tube 1185 can be a metal hypotube; the metal can be stainless steel. The injection tube 1185 can have a circular cross section. The injection tube 1185 can have a non-circular cross section. The injection tube 1185 can have a diameter in the range 25 to 20 gauge. The shaft 1182 can be the shaft of a catheter stylet, such as the shaft of an epidural catheter's stylet. The shaft 1182 can be a metal rod; the metal can be stainless steel or nitinol. The shaft 1182 can be a metal tube. The shaft 1182 can be straight. The shaft 1182 can be curved. The shaft 1182 can be bendable to meet a physician's needs. The shaft 1182 can be bendable to facilitate steering of the catheter 1115 within the living body. The distal tip 1183 can have the same diameter as the shaft 1182. The distal tip 1183 can have a diameter that is larger than the diameter of the 1182; one advantage of this configuration is that the shaft 1182 is less likely to exit holes in the side barrel of the catheter 1115 when the catheter 1115 is bent within a living body and the stylet 1180 is moved relative to the catheter 1115. In certain embodiments, the distal tip 1183 has a substantially spherical shape. In certain embodiments, the distal tip 1183 has a non-spherical shape. The injection tube 1185 and shaft 1182 can be fixedly connected by junction 1186. Junction 1186 can be a solder joint. Junction 1186 can be a glue joint. Junction 1186 can be an electrically conductive connection; one advantage of an electrically conductive connection 1186 is that an electrical signal connected to injection tube 1185 is transmitted to shaft 1182. In certain embodiments, the injection stylet 1180 can be an RF electrode. In certain embodiments, the injection stylet 1180 can include a temperature sensor. In certain embodiments, the injection stylet 1180 can have an integral connector for an RF generator. In certain embodiments, an RF connection can attached to the stylet 1180, for example, by means of an alligator clip.

When clamp 1141 creates a fluids seal around the catheter 1115 and clamp 1131 creates a fluid seal around the injection tube 1185, fluid injected into port 1184 flows through the adaptor 1120, into the inner lumen of the catheter 1115, and out of holes in the shaft of the catheter 1115, such as widely-spaced coil loops 1103 of the catheter tip 1100. One advantage of the injection adapator 1120 and the injection stylet 1184 is that fluid can be injected into a living body through a catheter 1115 when the stylet shaft 1182 is within the inner lumen of the catheter.

One advantage of a system that includes an injection stylet 1180 configured for a catheter 1115 and an injection adaptor 1120 that includes a fluid clamp port 1131 for a catheter 1115, a fluid clamp port 1141 for a stylet, and a central lumen connecting the two ports, is that it provides for injection of fluid injection into the catheter 1115 without an injection port that is not substantially coaxial with the catheter 1115. One advantage of a system that includes an injection stylet 1180 configured for a catheter 1115 and an injection adaptor 1120 that includes a fluid clamp port 1131 for a catheter 1115, a fluid clamp port 1141 for a stylet, and a central lumen connecting the two ports, is that it provides for enhanced ergonomics for manual rotation of the catheter by means of the adaptor hub 1020.

Figure 11A:
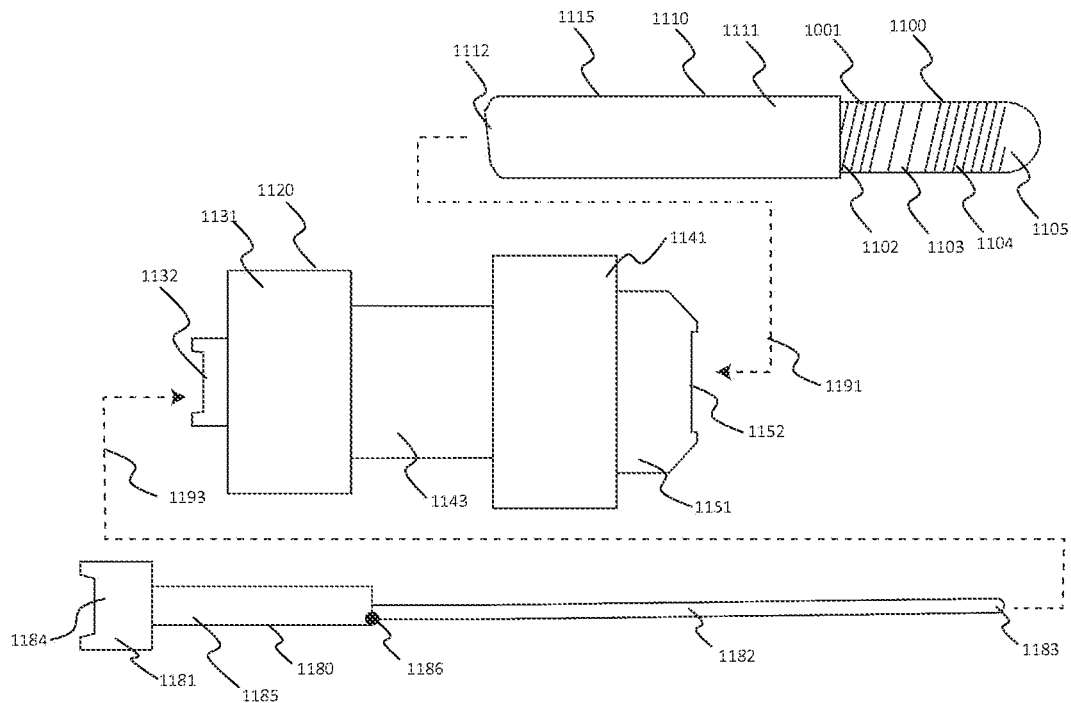
FIG. 11A is a schematic diagram showing an injection catheter system in an external view, wherein the injection catheter system includes a catheter, an injection adaptor hub, and an injection stylet, and wherein the injection adaptor hub includes a fluid clamp for the catheter and a fluid clamp for the injection stylet.

Referring specifically to FIG. 11A, one embodiment of the catheter 1115, adaptor 1120, and stylet 1180 are presented as separate pieces. Catheter 1115 can be inserted into adaptor 1120 as shown by arrow 1191. Injection stylet 1180 can be inserted into injection adaptor 1120 as shown by arrow 1193. In certain embodiments, the proximal end of the shaft 1182 is fixed within the inner lumen of injection tube 1185 and does not fully occlude the flow path of the injection tube 1185; one example of a cross-sectional view of this embodiment is shown in FIG. 10D. One advantage of embodiments in which the shaft 1182 is placed within the inner lumen of the injection tube 1185 is that it provides a cylindrical exterior surface around which clamp 1131 can create a fluid seal.

Figure 11B:
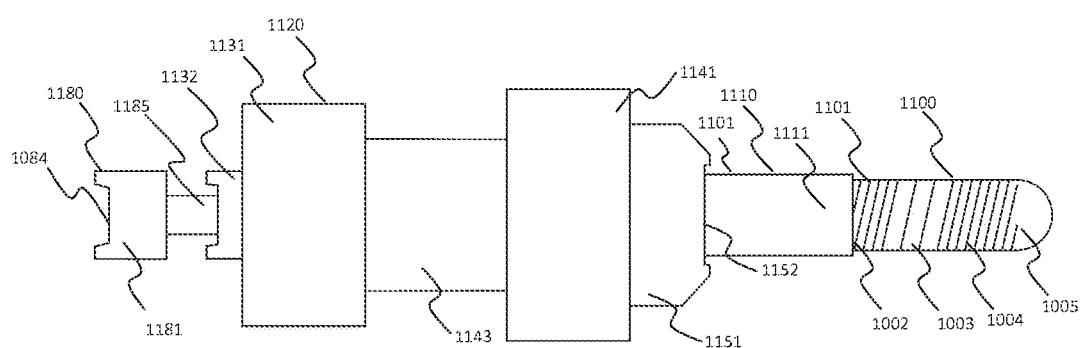
FIG. 11B is a schematic diagram showing an assembled injection catheter system in an external view, wherein the injection catheter system includes a catheter, an injection adaptor hub, and an injection stylet, and wherein the injection adaptor hub includes a fluid clamp for the catheter and a fluid clamp for the injection stylet.

Referring specifically to FIG. 11B, one embodiment of the assembly of a catheter 1115, adaptor 1120, and stylet 1180 is presented in an external view. In one embodiment, assembly shown in FIG. 10B can be effected as indicated by the arrows 1191 and 1193 shown in FIG. 10A. In this assembly, the clamp 1131 creates a substantially fluid-tight seal around the injection tube 1185, and clamp 1141 creates a substantially fluid-tight seal around the catheter 1115. One advantage of this assembly is that fluid injected into port 1184 does not substantially leak out of ports 1132 and 1152.

Figure 11C:
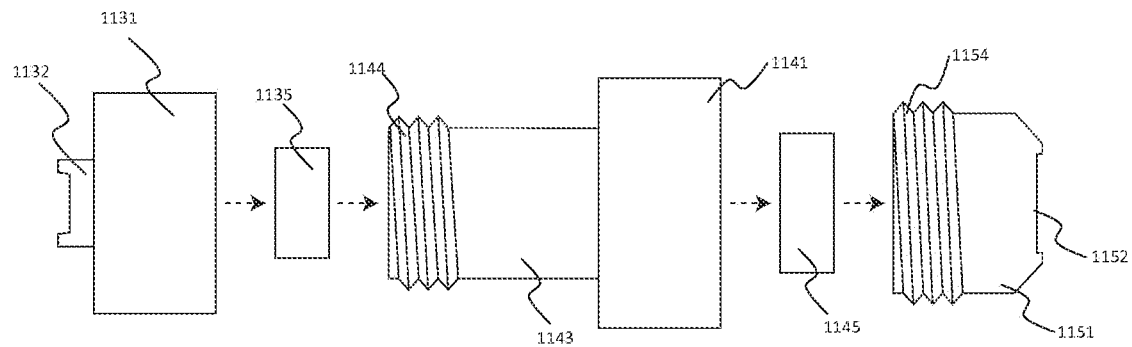
FIG. 11C is a schematic diagram showing the construction of an injection adaptor hub for a catheter that includes a fluid clamp for a catheter and a fluid clamp for a stylet.
Figure 11D:
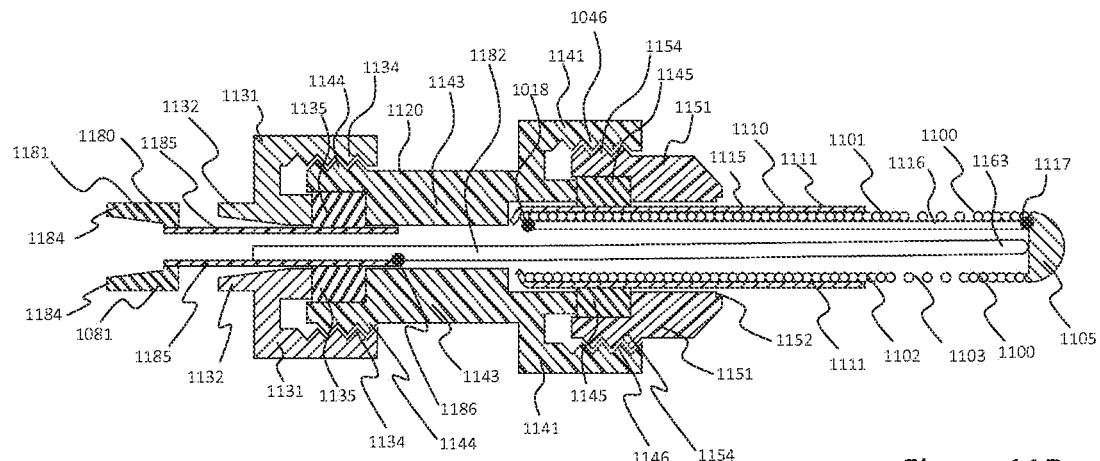
FIG. 11D is a schematic diagram showing an assembled injection catheter system in a cross-sectional view, wherein the injection catheter system includes a catheter, an injection adaptor hub, and an injection stylet, and wherein the injection adaptor hub includes a fluid clamp for the catheter and a fluid clamp for the injection stylet.
Figure 11E:
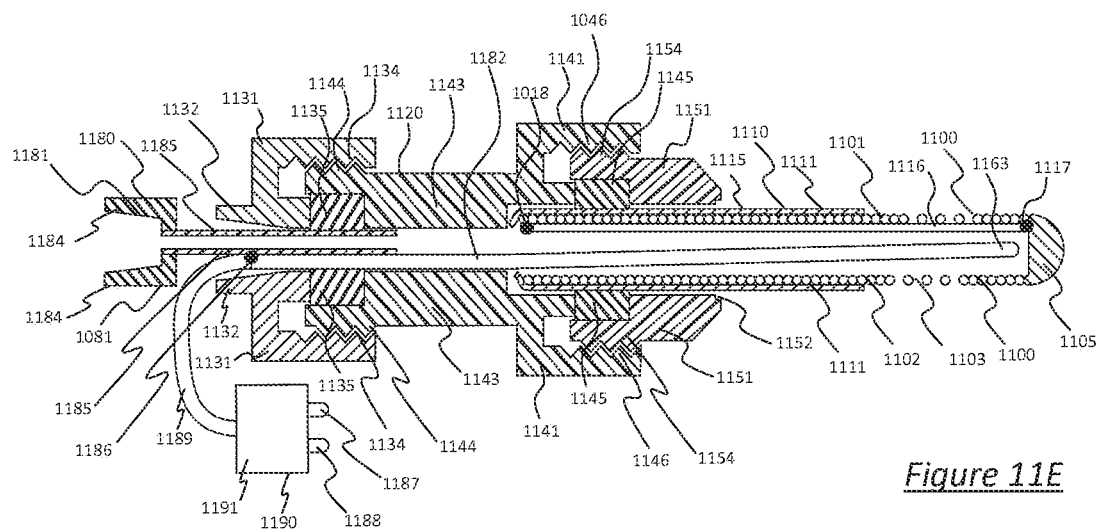
FIG. 11E is a schematic diagram showing an assembled injection catheter system in a cross-sectional view, wherein the injection catheter system includes a catheter, an injection adaptor hub, and an injection stylet electrode, and wherein the injection adaptor hub includes a fluid clamp for the catheter and a fluid clamp for the injection stylet electrode.
Figure 11F:
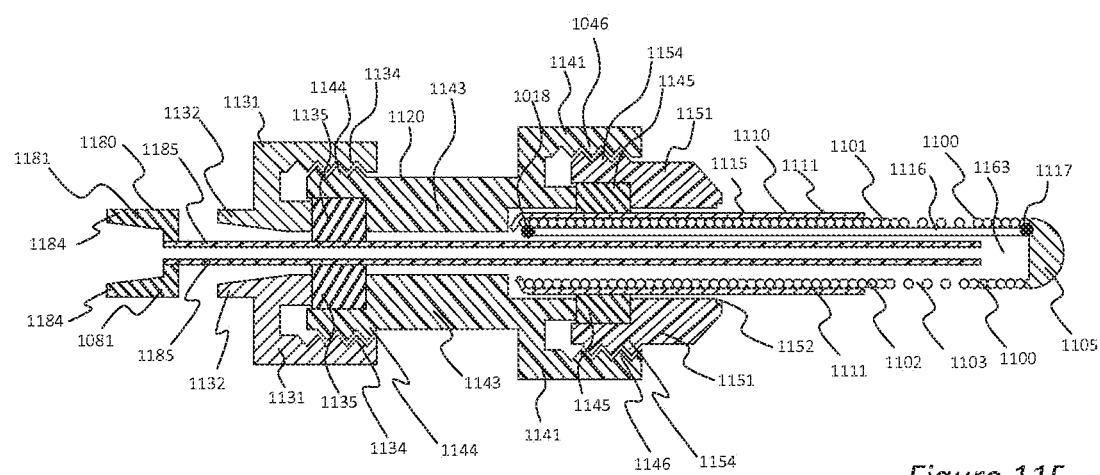
FIG. 11F is a schematic diagram showing an assembled injection catheter system in a cross-sectional view, wherein the injection catheter system includes a catheter, an injection adaptor hub, and an injection stylet, and wherein the injection adaptor hub includes a fluid clamp for the catheter and a fluid clamp for the injection stylet.

Referring specifically to FIGS. 11D, 11E, and 11F, certain embodiments of the assembly of a catheter 1115, adaptor 1120, and stylet 1180 are presented, wherein the catheter 1115 and adaptor 1120 are presented in a cross-sectional view, and the stylet 1180 is presented in a cross sectional view, except for the shaft 1182, if present, which is presented in an external view.

Referring specifically to FIGS. 11C, 11D, 11E, and 11F, one embodiment of the construction of an injection adaptor 1120 is presented. In FIG. 11C, the construction is shown in an exploded view. In FIGS. 11D, 11E, and 11F, the construction is shown is an assembled, cross-sectional view. The adaptor is constructed from five pieces, each of which is substantially axially-symmetric around the proximal-distal axis. The first piece includes the proximal port 1132 and the clamp ring 1031, which can be constructed from a substantially incompressible substance, such as a hard plastic. The second piece is an tubular structure 1035, which can be constructed from a compressible substance such as a soft plastic. The third piece includes the middle body 1043 and clamp ring 1041, which can be constructed from a substantially incompressible substance, such as a hard plastic. The fourth piece is tube 1045, which can be constructed from a compressible substance such as a soft plastic. The fifth piece is the distal body 1051, which can be constructed from a substantially incompressible substance, such as a hard plastic. The ring 1131 includes threads 1134 that can engage with the threads 1144 that are included on body 1143; this engagement can compress tube 1135 and reduce its internal diameter, thereby creating a substantially fluid-tight seal among the body 1143, the ring 1131, the gasket 1135, and the a stylet 1180 positioned in the inner lumen of the tube 1135. The ring 1141 includes threads 1146 that can engage with the threads 1154 that are included on body 1151; this engagement can compress tube 1145 and reduce its internal diameter, thereby creating a substantially fluid-tight seal among the body 1151, the ring 1141, the gasket 1145, and the a catheter 1115 positioned in the inner lumen of the tube 1145. One advantage of the embodiment of the injection adaptor 1120 presented in FIGS. 11C, 11D, 11E, and 11F is that the two fluid clamps prevent leaking a fluids from the injection hub 1120 when the injection hub 1120 is engaged with the stylet 1180 and the catheter 1115 and said fluids are injected into port 1184 of the stylet.

In certain embodiments, the injection adaptor hub 1120 can be constructed from more than five pieces. In certain embodiments, the adaptor 1120 can be constructed from fewer than five pieces. In certain embodiments, the components of the adaptor 1120 shown in FIGS. 11C, 11D, 11E, and 11F can be constructed from multiple pieces. In certain embodiments, the threaded ring 1131 can rotate around port 1132. In certain embodiments, the threaded ring 1141 can rotate around body 1143. In certain embodiments, middle body 1143 can be constructed from two pieces. In some embodiment of the injection adaptor 1120, a different type of fluid clamp can be included. In certain embodiments of the injection adaptor 1120 and catheter 1115, the adaptor and catheter can be inseparably connected.

Referring specifically to FIG. 11D, one embodiment of an injection stylet 1180 is presented in a cross-sectional view. In this embodiment, the shaft 1182 is fixed inside the inner lumen of injection tube 1185. The shaft 1182 does not block the flow path through the injection tube 1185. The gasket 1135 clamps around the smooth, cylindrical outer diameter of the injection tube 1185. In certain embodiments, the proximal end of the shaft 1182 can extend up to or proximal to the proximal end of the injection tube 1185, and the junction 1186 can be on the proximal end of the shaft. In certain embodiments, the shaft 1182 can extend proximal to the tube 1185 and the junction 1186 can be between the handle 1181 and the shaft 1182. In embodiments where the injection tube 1185, junction 1186, shaft 1182 are electrically conductive, an electrical signals, such as an RF signal or a nerve stimulation signal, can be attached to a portion of the injection tube proximal to port 1132, and thereby the electrical signal can be transmitted to the catheter 1115 by contact between an inner metal surface of the catheter and the shaft 1182. One advantage of embodiments that include an injection tube 1185 that does not extend into the inner lumen of the catheter 1115 and a stylet rod 1182 that does extend into the inner lumen of the catheter 1115, is that the flow of fluids injected into port 1184 are not blocked by flexing of the catheter shaft which could close down the inner lumen of the injection tube 1185 were it positioned within the inner lumen of the catheter 1115 and kinked by the flexing.

Referring specifically to FIG. 11E, one embodiment of an injection stylet 1180 is presented in a cross-sectional view. In this embodiment, the shaft 1182 is fixed outside the injection tube 1185. In certain embodiments, as shown in FIG. 11E, the shaft 1182 is fixed to the outer surface of the injection tube 1185. In certain embodiments, the shaft 1182 is fixed to the handle 1181, for example, by gluing both the shaft 1182 and the injection tube 1185 into a distal opening of the handle 1181. In some embodiment, as shown in FIG. 11E, an integral connection to an electrical generator 1190, such as an RF generator, is attached to the injection stylet 1180. The connection can provide for delivery of electrical signals to the stylet 1180, and thereby to a catheter 1115 into which the injection stylet 1180 is placed, and it can provide for conduction of measurement signals from the stylet 1115 to a generator, such as temperature signals. The cable 1189 of the connection 1190 can be flexible.

Referring now to FIG. 11F, one alternative embodiment of the assembly of a catheter 1115, injection adaptor 1120, and injection stylet 1180 is presented, wherein the injection stylet 1180 includes an injection tube 1185 that is configured to function as a stylet for a catheter 1115. In this embodiment, the injection tube 1185 has a length that is configured to pass through the hub 1120 and into the inner lumen of the catheter 1115. In certain embodiments, the tube 1185 is configured to align with the distal end 1105 of the catheter in the assembly. In certain embodiments, the tube 1185 is configured not to reach the distal end 1105 of the catheter in the assembly. In certain embodiments, the tube 1185 is straight. In certain embodiments, the tube 1185 is curved. In certain embodiments, the tube 1185 has a circular cross-section. In certain embodiments, the tube 1185 has a non-circular cross section. In certain embodiments, the tube 1185 has a rectangular cross section. In certain embodiments, the tube 1185 is reinforced with a rod fixed inside its inner lumen. One advantage of the injection stylet 1180 presented in FIG. 11F is ease of construction.

Referring now to FIGS. 12A, 12B, 12C, 12D, 12E, 12F, 12G, 12H, 12I, 12J, 12K, 12L, 12M, 12N, 12O, 12P, 12Q, 12R, 12S, 12T, 12U, 12V, 12W, 12X, and 12Y, FIG. 12 presents certain embodiments of an epidural RF cannula, which includes a hollow needle 1200 and a stylet 1250, in accordance with several aspects of the present invention. In certain embodiments, the cannula system 1200 and 1250 can be configured for the systems and methods related to catheter systems presented in the embodiments presented in FIG. 1.

Figure 12A:
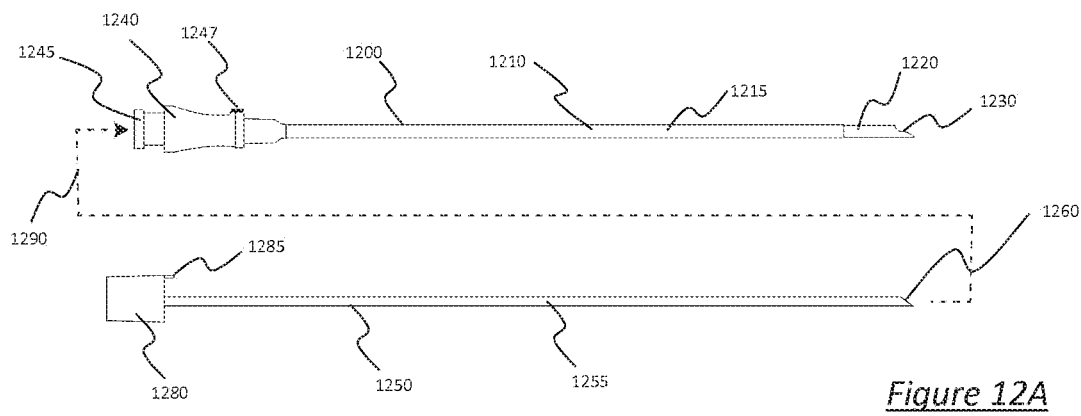
FIG. 12A is a schematic diagram showing a cannula system configured for the introduction of a catheter into the living body.
Figure 12B:
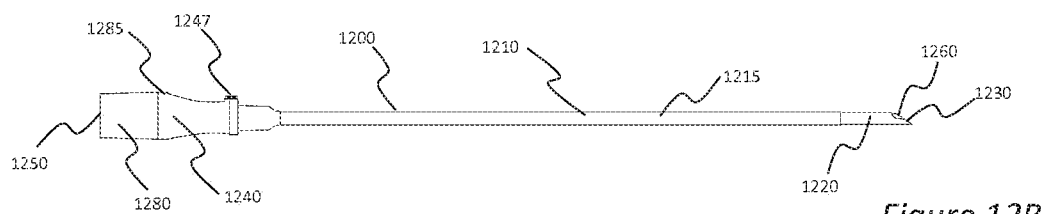
FIG. 12B is a schematic diagram showing an assembled cannula system configured for the introduction of a catheter into the living body.
Figure 12C:
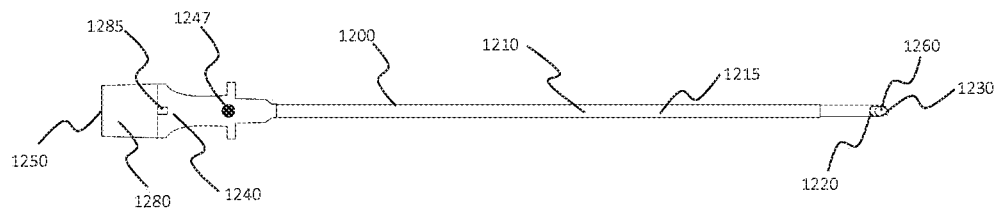
FIG. 12C is a schematic diagram showing an assembled cannula system configured for the introduction of a catheter into the living body.
Figure 12D:
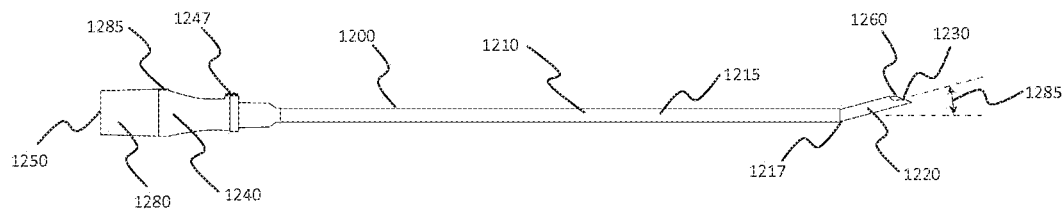
FIG. 12D is a schematic diagram showing an assembled cannula system configured for the introduction of a catheter into the living body, wherein the shaft of the cannula includes a bend.
Figure 12E:
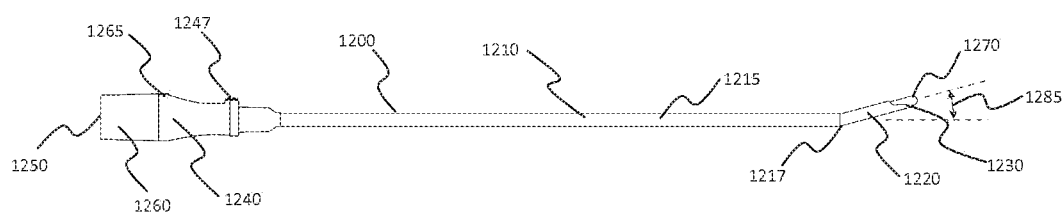
FIG. 12E is a schematic diagram showing an assembled cannula system configured for the introduction of a catheter into the living body, wherein the shaft of the cannula has a bend and the stylet is configured to protrude from the distal end of the cannula.
Figure 12F:
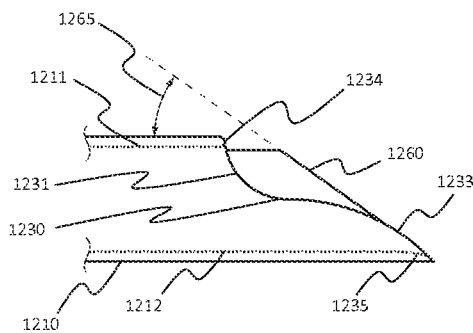
FIG. 12F is a schematic diagram showing a needle bevel and a stylet bevel configured for the introduction of a catheter into a living body.
Figure 12G:
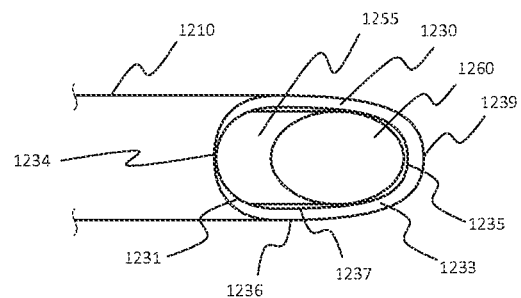
FIG. 12G is a schematic diagram showing a needle bevel and a stylet bevel configured for the introduction of a catheter into a living body.

Referring to FIGS. 12A, 12B, and 12C, 12F, and 12G, certain embodiments of an epidural RF cannula system are presented in several views. The epidural RF cannula system includes a hollow needle 1200 and a stylet 1250. The cannula 1200 includes a port 1245 at its proximal end, a hub 1240, a marker 1247 that indicates the orientation of the bevel 1230, a hollow metal shaft 1210, electrical insulation 1215 covering a proximal length of the shaft 1210, an active tip 1220 at the distal end of the shaft 1210 that is not covered by electrical insulation, and an epidural bevel 1230. The stylet 1250 includes a proximal cap 1280, an alignment feature 1285 that is configured to engage with the cannula hub 1240 and thereby align the bevel 1260 of the stylet 1250 and the bevel 1230 of the needle 1200, a shaft 1255, and a bevel 1260 at the distal end of the shaft 1255. FIG. 12A presents the cannula 1200 and stylet 1250 separately in an external view from the side of the bevel; herein this view is referred to this view as a "side view" of the system. FIG. 12B presents the cannula and stylet engaged, with the stylet within the inner lumen of the cannula, from the same external side view as presented in FIG. 12A. FIG. 12C presents a second external view of the assembled cannula 1200 and stylet 1250, wherein the view is rotated 90 degrees around the proximal-to-distal axis of the cannula 1200 starting from the view in FIG. 12B; herein, this view is referred to as a "top view" of the needle system. FIG. 12F presents a detailed side view of the needle bevel 1230 and stylet 1260 wherein the cannula 1200 and stylet 1250 are fully engaged as shown in FIG. 12B. FIG. 12G presents a detailed top view of the needle bevel 1230 and stylet 1260 wherein the cannula 1200 and stylet 1250 are fully engaged as shown in FIG. 12C.

In certain embodiments, the cannula port 1245 can be a female luer port. The port 1245 can be configured for injection of fluids. The port 1245 can include a luer lock. In certain embodiments, the hub 1240 can be metal, such as stainless steel. In certain embodiments, the hub 1240 can be plastic. The hub 1240 can include the port 1245. The hub 1240 has an inner lumen which provides for fluid communication between the port 1240 and the inner lumen of the shaft 1210. In certain embodiments, the hub can be configured to engage with detachable "wings" to facilitate manipulation of the needle, as is familiar to one skilled in the art of needles for epidural anesthesia. In certain embodiments, the hub can include fixed wings that are inseparable from the hub. In certain embodiments, the hub marker 1247 can be rotationally with the opening of the bevel 1230. In other embodiments, the hub marker 1247 can be on the opposite side of the shaft relative to the cut or cuts of the bevel 1230. The cannula shaft 1210 can include stainless steel hypotube. The cannula shaft 1210 can be constructed from a metal hypotube selected from among the following sizes 18TW, 18RW, 17TW, 17RW, 16TW, 16RW, 15TW, 15RW, 14TW, 14RW, and other sizes. The shaft 1210 can include depth markers, including bands that indicate 1 cm lengths along the shaft. The length of the shaft 1210 can be 5 cm. The length of the shaft 1210 can be 6 cm. The length of the shaft 1210 can be 10 cm. The length of the shaft 1210 can be 15 cm. The length of the shaft 1210 can be 20 cm. The length of the shaft 1210 can be 3.5 inches. The length of the shaft 1210 can be 4.5 inches. The length of the shaft 1210 can be 6 inches. In certain embodiments the shaft 1210 of the needle 1200 can be cylindrical. In certain embodiments the shaft 1210 of the needle 1200 can be substantially axially symmetric. The inner lumen of the cannula 1200 can be configured to allow a catheter, including a catheter-style electrode system, to pass into the port 1245, through the shaft 1210, and out from the bevel 1230. The inner lumen of the cannula 1200 can be configured for fluid to be injected into the port 1245, through the shaft 1210, and out from the bevel 1230. The inner lumen of the cannula 1200 can be configured for fluid to be injection into the port 1245, through the shaft 1210, and out from the bevel 1230. The inner lumen of the cannula 1200 can be configured so that an RF electrode can be inserted into the port 1245, pass into the inner lumen of the metal shaft 1210, and contact an inner surface of the metal shaft 1210, thereby providing for the delivery and control of RF signal output to living tissue in contact with the active tip 1220. In certain embodiments, the length of the shaft 1210 can be configured such that an RF electrode's distal end aligns with the distal bevel 1230 when the electrode is fully engaged with the cannula 1200. The electrical insulation 1215 can be a plastic tube, such as shrink tube, covering and adhered to the metal shaft 1210. The electrical insulation 1215 can be a plastic coating. The electrical insulation 1215 can be fixedly attached to the underlying metal shaft 1210. The electrical insulation 1215 can be a proximal plastic tube attached to a distal metal tube that forms the tip 1220. The electrical insulation 1215 can be configured to prevent RF current from flowing from electrically-insulated areas of the shaft. In certain embodiments, the insulation 1215 covers the proximal end of the shaft 1210, leaving the distal end 1220 uninsulated. In certain embodiments, the insulation 1215 leaves multiple regions of the shaft uninsulated. The active tip 1220 can be en electrically-uninsulated length of the metal shaft 1210. The length of the active tip 1220 can be 1 mm. The length of the active tip 1220 can be 2 mm. The length of the active tip 1220 can be 4 mm. The length of the active tip 1220 can be 5 mm. The length of the active tip 1220 can be 6 mm. The length of the active tip 1220 can be 10 mm. The length of the active tip 1220 can be 15 mm. The length of the active tip 1220 can be 20 mm. The length of the active tip 1220 can be 30 mm. The length of the active tip 1220 can be in the range 1-30 mm. The length of the active tip 1220 can be less than 1 mm. The length of the active tip 1220 can be greater than 30 mm. In certain embodiments, the bevel 1230 can be an epidural bevel, such as a tuohy bevel, an RX bevel, a Cath Glide bevel, a Higuchi bevel. In certain embodiments, the bevel 1230 can be configured to limit damage to a catheter that passes through it. In certain embodiments, the bevel can be configured for insertion into the epidural space. In certain embodiments, the bevel 1230 can be configured to prevent damage to the dura mater of the spinal cord. In certain embodiments, the bevel 1230 can provide by penetration of skin and tissue of the posterior spine. In certain embodiments, the cannula 1200 is configured to introduce a catheter that includes an outer surface that is plastic. In certain embodiments, the cannula 1200 is configured to introduce a catheter that includes a shaft that is constructed from a spring coil that is covered by electrical insulation. In certain embodiments, the cannula 1200 is configured to introduce a catheter that includes a shaft that is constructed from a spring coil that includes an outer surface and an inner lumen, wherein the outer surface is surrounded by a plastic tube.

The stylet 1250 can be configured to occlude a portion of the inner lumen of the cannula 1200. The stylet 1250 can be configured to reduce coring of tissue when the cannula 1200 penetrates solid tissue. The stylet 1250 can be configured to reduce insertion force required to advance the cannula 1200 into living tissue. The stylet 1250 can be configured to stiffen the shaft of the cannula 1200. In certain embodiments, the stylet cap 1280 can be configured to engage with the hub 1240 for the purpose of fixing a longitudinal distance between the distal end of the stylet 1250 and the distal end of the cannula 1200. In certain embodiments, the alignment tab can engage with a feature of the hub 1240 to provide for fixing the rotational alignment the cannula bevel 1230 and the stylet bevel 1260. In certain embodiments, engagement of the hub 1240 and the cap 1280 can provide for a particular, substantially solid tip geometry when the stylet 1250 is fully engaged with the cannula 1200. In certain embodiments, the cap 1280 can engage with the hub 1240 by means of an interference fit. In certain embodiments, the cap 1280 can engage with the hub 1240 in a locked configuration. In certain embodiments, the cap 1280 can engage with the hub 1240 by means of a luer lock. The stylet shaft 1255 can be a solid rod. The stylet shaft 1255 can be a metal rod, such as stainless steel. The sylet shaft 1255 can be a plastic rod, such as nylon. The stylet shaft can be a hard, flexible plastic rod. One advantage of a plastic stylet rod 1255 is that it can bend to pass through a curved cannula shaft 1210. The length of the stylet shaft 1255 can be equal to the length of the cannula shaft 1210. The length of the stylet shaft 1255 can be larger than the length of the cannula shaft 1210. The length of the stylet shaft 1255 can be shorter than the length of the cannula shaft 1210. The bevel 1260 of the stylet can have a similar geometry to that of the cannula bevel 1230. The outer diameter of the stylet shaft 1255 can be configured to provide for smooth movement of the shaft 1255 within the inner lumen of the cannula shaft 1210. In certain embodiments, the stylet shaft 1255 can completely occlude the inner lumen of the cannula shaft 1210. In certain embodiments the shaft 1255 of the stylet 1255 can be cylindrical. In certain embodiments the shaft 1255 of the stylet 1255 can be substantially axially symmetric. The bevel 1260 of the stylet can have an similar geometry to that of the cannula bevel 1230. The bevel of 1260 of the stylet can be formed from the same cutting surfaces as those that formed the cannula bevel 1230. The bevel of 1260 of the stylet can have a shape shaped such that when the stylet 1250 is inserted into the cannula 1200, and the hub 1240 and the cap 1280 are fully engaged, the assembled needle has a substantially smooth combined bevel.

Referring to FIG. 12A, arrow 1290 shows the way in which the stylet 1250 can be inserted into the cannula 1200.

Referring to FIGS. 12B, 12C, 12G, and 12H, the bevel 1230 of the cannula 1200 and the bevel 1260 of the stylet 1250 are aligned longitudinally and rotationally when the cannula hub 1240 is fully engaged with the stylet cap 1280.

Referring to FIGS. 12F and 12G, the cannula bevel 1230 includes two curved surfaces, a distal surface 1233 and a proximal surface 1231. In certain embodiments, the proximal bevel surface 1231 is a concave cylindrical cut. In certain embodiments, the proximal bevel surface 1233 is a convex cylindrical cut. In certain embodiments, the proximal 1231 and distal 1233 are cylindrical cuts. The stylet bevel 1260 includes one flat surface whose angle 1265 relative to the long axis of the stylet 1250 is configured to be substantially parallel to the average angle of distal aspect of the distal cannula bevel 1233. In one example the angle 1265 is substantially equal to 35 degrees. In certain embodiments, the angle 1265 is within the range 35-55 degrees. Surface 1211 is the inner surface of the shaft 1210 that is on the same side of the shaft as the bevel opening 1230. Surface 1212 is the inner surface of the shaft 1210 that is on the opposite side of the shaft relative to the bevel opening 1230. The transition from the inner surface of the shaft to the outer surface can be rounded to prevent damage to a catheter passing through the bevel 1230, when the stylet is removed. The proximal portion 1234 of the bevel 1230, which can be referred to as the "heel" 1234 of the bevel, can be rounded on both its inner and outer edges to reduce the likelihood of damage to a flexible catheter that bends over the heel 1234. For example, the heel 1234 can be full radiused. For example, the heel 1234 can have edges whose radious of curvature is no smaller than 0.002 inches. The distal, inner edge 1235 of the bevel 1230 can be smoothed to minimize cutting edges and thereby provide for smooth, damage-free passage of a catheter through the bevel 1230, when the stylet 1250 is removed. The inner edge 1237 of the bevel 1230 can radiused, for instance by polishing, sand blasting, or grinding, to minimize cutting edges that can damage a catheter. The junction between the distal bevel 1233 and the proximal bevel 1231 can be smoothed and/or filleted, as appropriate, to reduce sharp edges. In certain embodiments, the distal aspect 1239 of the outer edge 1236 of the bevel 1230 can be sharpened. In certain embodiments, the distal aspect 1239 of the outer edge 1236 of the bevel 1230 be configured to penetrate solid tissue, such as skin and muscle. In the embodiment presented in FIGS. 12F and 12G, the cannula 1200 and the stylet 1250 are configured to produce a combined bevel that is sufficiently a solid, flat bevel. One advantage of an epidural bevel that includes a curved proximal surface and a curved distal surface is that the bevel opening is enlarged, the distal bevel angle is less sharp, and the bevel can be free of sharp junctions between the multiple surfaces that are included in the bevel.

One advantage of the embodiments of an epidural RF cannula system presented in FIGS. 12A, 12B, 12C, 12F, and 12G is that the system can provide for percutaneous access to the epidural space, delivery of epidural anesthesia through the needle 1200, insertion of a catheter into the epidural space through the needle 1200, and delivery of targeted high-frequency electrotherapy to nerves in the epidural space via the active tip of the cannula 1220. One advantage of the present invention is that electrical signals, such as nerve stimulation, radiofrequency, pulsed radiofrequency, PENS, TENS, muscle stimulation, and neuromodulation signals, can be applied to human body in a targeted manner by the same needle 1200 by means of which a catherer is introduced into the human body.

In certain embodiments, the shaft 1210 can include echogenic markers. Echogenic markers can be configured to enhance visibility of an object when imaged using an ultrasound apparatus. In certain embodiments, the tip can include echogenic markers. In certain embodiments, the echogenic markers can be indentations into the metal surface of the metal of the shaft 1210. In certain embodiments, the echogenic markers can be solid objects insertion between the insulation 1215 and the metal shaft 1210. In certain embodiments, the echogenic markers can be a roughing of the surface of the shaft 1210, for example, roughing as produced by sand blasting. In certain embodiments, echogenic markers can be positioned only at the active tip 1220. In certain embodiments, echogenic markers can be positioned at a distal aspect for the active tip 1220 and at a proximal aspect of the active tip 1220; one advantage of such embodiments is that the distal and proximal extent of the active tip 1220 can be discerned more easily using ultrasound. In certain embodiments, one echogenic marker is positioned at a distal aspect of the active tip 1220, and a second echogenic marker is positioned at the distal aspect of the insulation 1215; one advantage of this configuration is that the distal and proximal ends of the active tip 1220 can be viewed using ultrasound imaging.

Referring to FIGS. 12D and 12E, certain embodiments of an epidural RF cannula are presented in which the shaft 1210 includes a bend 1217. The bend 1217 can deflect the distal end of the shaft 1210 by an angle 1285 with respect to the proximal end of the shaft 1210. The curve 1217 can be configured to provide for improved steerability of the needle 1200 through solid tissue. The bend 1217 can be configured to facilitate positioning of the needle 1200 within the living body. One advantage of the bend 1217 is that the shaft 1210 can approach a vertebra at a steep angle and the distal aspect of the shaft 1210 can direct a catheter out of the bevel 1230 at a more shallow angle, for example, more parallel to the epidural space. One advantage of curve 1217 is that a catheter's initial trajectory can be adjusted by rotating the cannula 1200 about its central axis. The bend 1217 can be positioned at the distal aspect of the insulation 1215. The bend 1217 can be positioned proximal to the distal end of the insulation 1215. The bend 1217 1217 can be positioned distal to the distal end of the insulation 1215. The bend 1217 can be positioned 5 mm from the distal tip of the cannula 1200. The bend 1217 can be positioned 10 mm from the distal tip of the cannula 1200. The bend 1217 can be positioned 15 mm from the distal tip of the cannula 1200. The curve 1217 can extend from 10 mm proximal to the distal tip of the cannula 1200 to the distal tip of the cannula 1200. The angle 1285 can be 5 degrees. The angle 1285 can be 10 degrees. The angle 1285 can be 15 degrees. The angle 1285 can be 20 degrees. The angle 1285 can be in the range 5 to 20 degrees. The angle 1285 can be greater than 20 degrees. One advantage of a plastic stylet shaft 1255 is that the stylet 1250 can follow the bend 1217 as is passes through the inner lumen of the shaft 1210. One advantage of an undercut metal stylet shaft 1255 is that is can pass by the bend 1217, through the inner lumen of the shaft 1210, more easily.

Referring to FIG. 12E, certain embodiments of an epidural RF cannula are presented in which the distal end of the stylet 1250 extends beyond the distal end of the cannula 1200 when the stylet 1250 is seated within the cannula 1200. In certain embodiments, the stylet 1250 can have a blunt distal end 1270. The tip 1270 can be full radiused. In certain embodiments, the bevel 1230 of the cannula 1200 and the tip 1270 of the stylet can be configured to form a substantially blunt-tip, solid needle, when the cannula 1200 and stylet 1250 are fully engaged. The shaft 1255 of the stylet 1250 can be a flexible, hard plastic, such as nylon. The shaft 1255 can be constructed of a material that can both easily pass through bend 1217 and extend beyond the bevel 1230 in a substantially straight configuration when in tissue. In one example, the distal end of the stylet shaft 1255 can extend beyond the distal end of the cannula shaft 1210 by 0.050 inches. In one embodiment, a first stylet with a flat bevel 1260 that aligns with bevel 1230 is placed within the cannula 1200 to facilitate penetration of the cannula 1200 through the thicker tissue and into a sensitive bodily position, and then the first stylet is replaced by a second stylet that have a rounded tip 1270 that extends beyond the distal end of the cannula 1200 to prevent cutting of the internal structures when the cannula 1200 is manipulated in the said sensitive bodily position; in one example the tougher tissue can be skin and muscle overlying the spine, and the sensitive bodily position can be the epidural space.

Figure 12H:
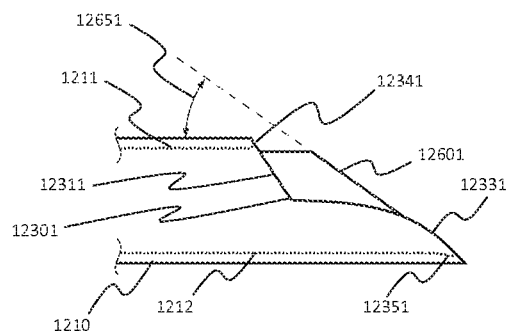
FIG. 12H is a schematic diagram showing a needle bevel and a stylet bevel configured for the introduction of a catheter into a living body.
Figure 12I:
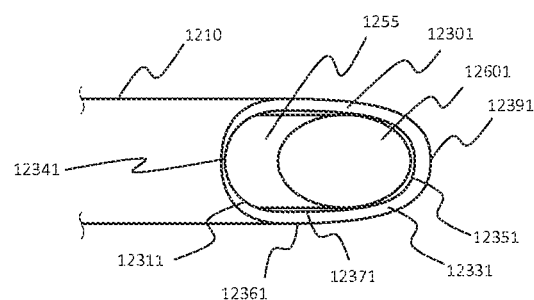
FIG. 12I is a schematic diagram showing a needle bevel and a stylet bevel configured for the introduction of a catheter into a living body.

Referring to FIGS. 12H and 12I, certain embodiments of a bevel 12301 for an epidural needle 1200 and a bevel 12601 for an epidural stylet 1250 are presented in a side view in FIG. 12H and in a top view in FIG. 12I. The cannula bevel 12301 includes two surfaces, a flat proximal surface 12311 that is angled relative to the transverse plane of the shaft 1210 at the position of the surface 12311, and a curved distal surface 12331. In one example, the distal surface 12331 has substantially one curvature when viewed from the side, as in FIG. 12H. In one embodiment, the angle of surface 12311 relative to the transverse plane of the shaft 1210 is 15 degrees. The stylet bevel 12601 includes one flat surface whose angle 12651 relative to the long axis of the stylet 1250 is configured to be substantially parallel to the average angle of distal aspect of the distal cannula bevel 12331. In one example the angle 12651 is substantially 35 degrees. In certain embodiments, the angle 12651 is within the range 35-55 degrees. Surface 1211 is the inner surface of the shaft 1210 that is on the same side of the shaft as the bevel opening 12301. Surface 1212 is the inner surface of the shaft 1210 that is on the opposite side of the shaft relative to the bevel opening 12301. The heel 12341 can be rounded to prevent damage to a catheter passing through the bevel. The inner edge of the bevel 12371 can be smoothed to prevent damage to a catheter passing through the bevel. The junction between the distal bevel 1233 and the proximal bevel 1231 can be smoothed and/or filleted, as appropriate, to reduce sharp edges. In certain embodiments, the distal aspect 1239 of the outer edge 1236 of the bevel 1230 can be sharpened, for example, for the purpose of penetrating solid tissue. The bevels 12301 and 12601 are configured to form a combined bevel that is sufficiently flat and solid. One advantage of an epidural bevel that includes a flat proximal surface and a curved distal surface is that the bevel opening is enlarged, the distal bevel angle is less sharp, and radius of the bevel heel can be enlarged, and the bevel can be free of sharp junctions between the multiple surfaces that are included in the bevel.

Figure 12J:
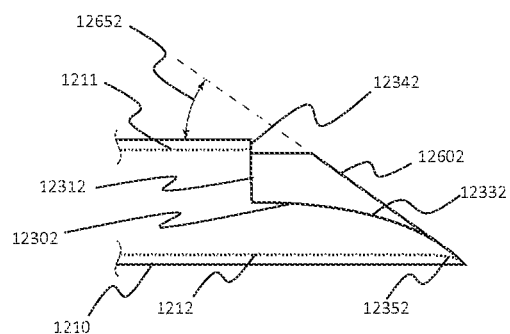
FIG. 12J is a schematic diagram showing a needle bevel and a stylet bevel configured for the introduction of a catheter into a living body.
Figure 12K:
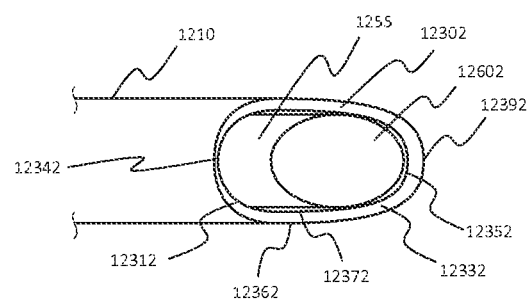
FIG. 12K is a schematic diagram showing a needle bevel and a stylet bevel configured for the introduction of a catheter into a living body.

Referring to FIGS. 12J and 12K, certain embodiments of a bevel 12302 for an epidural needle 1200 and a bevel 12602 for an epidural stylet 1250 are presented in a side view in FIG. 12J and in a top view in FIG. 12K. The cannula bevel 12302 includes two surfaces, a flat proximal surface 12312 that is parallel to the transverse plane of the shaft 1210 at the location of the surface 12312, and a curved distal surface 12331. In certain embodiments, the embodiments presented in FIGS. 12J and 12K can be special cases of the embodiments presented in FIGS. 12H and 12I, wherein the angle of surface 12311 relative to the transverse plane of the shaft 1210 is zero. One advantage of an epidural bevel that includes a flat proximal surface formed from a transverse cut, and a curved distal surface is that the bevel opening is enlarged, the distal bevel angle is less sharp, and radius of the bevel heel is maximized, and the bevel can be free of sharp junctions between the multiple surfaces that are included in the bevel.

Figure 12L:
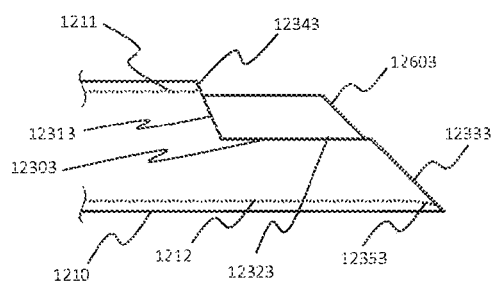
FIG. 12L is a schematic diagram showing a needle bevel and a stylet bevel configured for the introduction of a catheter into a living body.
Figure 12M:
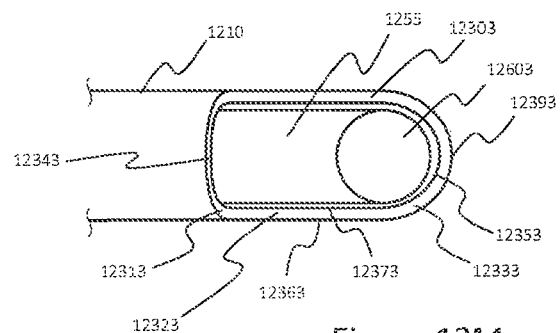
FIG. 12M is a schematic diagram showing a needle bevel and a stylet bevel configured for the introduction of a catheter into a living body.

Referring to FIGS. 12L and 12M, certain embodiments of a bevel 12303 for an epidural needle 1200 and a bevel 12603 for an epidural stylet 1250 are presented in a side view in FIG. 12L and in a top view in FIG. 12M. The cannula bevel 12303 includes three flat surfaces, a flat proximal surface 12313, a flat middle surface 12323, and a flat distal surface 12333. In certain embodiments, the surface 12323 can be parallel to the central axis of the shaft 1210. In certain embodiments the surface 12323 can form a non-zero angle relative to the longitudinal axis of the shaft 1210 at the location of the surface 12323. In certain embodiments, the heel 12343 and inner edge 12373 can be rounded to prevent damage to a flexible catheter passing through the bevel 12303. In certain embodiments, the distal outer edge 12393 of the bevel can be sharp to penetrate solid tissue.

Figure 12N:
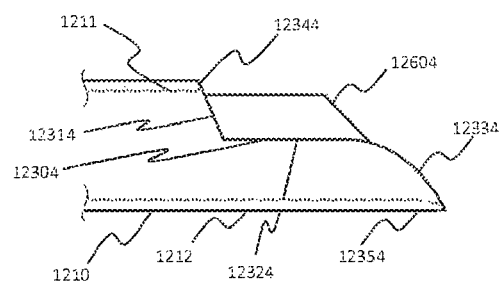
FIG. 12N is a schematic diagram showing a needle bevel and a stylet bevel configured for the introduction of a catheter into a living body.
Figure 12O:
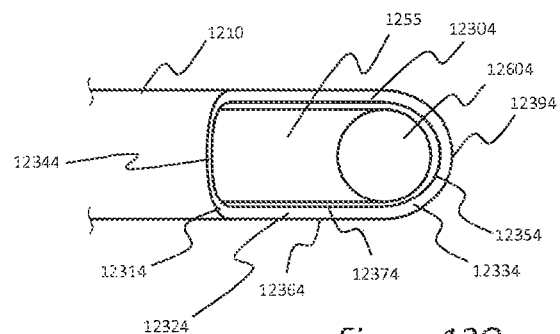
FIG. 12O is a schematic diagram showing a needle bevel and a stylet bevel configured for the introduction of a catheter into a living body.

Referring to FIGS. 12N and 12O, certain embodiments of a bevel 12304 for an epidural needle 1200 and a bevel 12604 for an epidural stylet 1250 are presented in a side view in FIG. 12N and in a top view in FIG. 12O. The cannula bevel 12304 includes three surfaces, a flat proximal surface 12314, a flat middle surface 12324, and a curved distal surface 12333. In certain embodiments, the surface 12324 can be parallel to the central axis of the shaft 1210. In certain embodiments the surface 12324 can form a non-zero angle relative to the longitudinal axis of the shaft 1210 at the location of the surface 12324. In certain embodiments, the heel 12344 and inner edge 12374 can be rounded to prevent damage to a flexible catheter passing through the bevel 12304. In certain embodiments, the distal outer edge 12394 of the bevel can be sharp to penetrate solid tissue. One advantage of the bevel 12304 of an epidural needle 1200 wherein the bevel includes a curved distal surface is that the junction between the distal surface and the proximal surface adjacent can have low curvature.

Figure 12P:
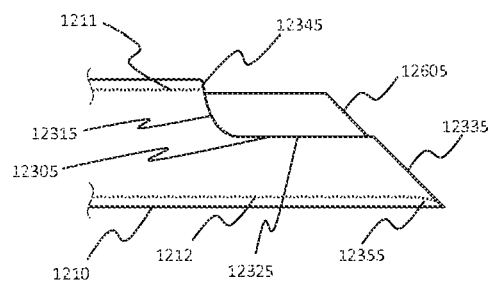
FIG. 12P is a schematic diagram showing a needle bevel and a stylet bevel configured for the introduction of a catheter into a living body.
Figure 12Q:
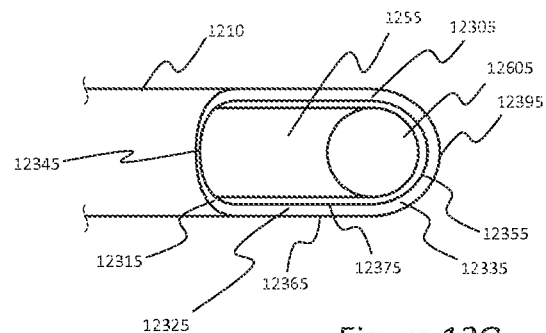
FIG. 12Q is a schematic diagram showing a needle bevel and a stylet bevel configured for the introduction of a catheter into a living body.

Referring to FIGS. 12P and 12Q, certain embodiments of a bevel 12305 for an epidural needle 1200 and a bevel 12605 for an epidural stylet 1250 are presented in a side view in FIG. 12P and in a top view in FIG. 12Q. The cannula bevel 12305 includes three surfaces, a curved proximal surface 12315, a flat middle surface 12325, and a flat distal surface 12335. In certain embodiments, the surface 12325 can be parallel to the central axis of the shaft 1210. In certain embodiments the surface 12325 can form a non-zero angle relative to the longitudinal axis of the shaft 1210 at the location of the surface 12325. In certain embodiments, the heel 12345 and inner edge 12375 can be rounded to prevent damage to a flexible catheter passing through the bevel 12305. In certain embodiments, the distal outer edge 12395 of the bevel can be sharp to penetrate solid tissue.

Figure 12R:
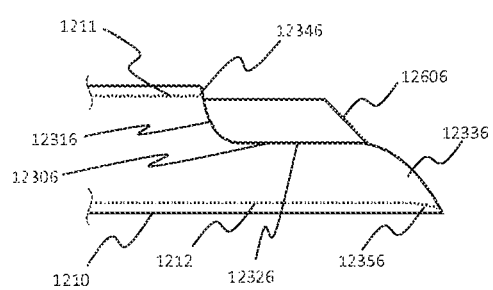
FIG. 12R is a schematic diagram showing a needle bevel and a stylet bevel configured for the introduction of a catheter into a living body.
Figure 12S:
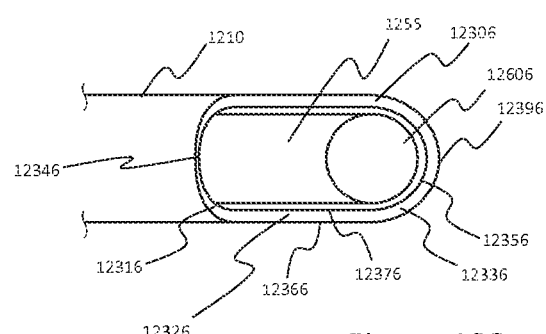
FIG. 12S is a schematic diagram showing a needle bevel and a stylet bevel configured for the introduction of a catheter into a living body.

Referring to FIGS. 12R and 12S, certain embodiments of a bevel 12306 for an epidural needle 1200 and a bevel 12606 for an epidural stylet 1250 are presented in a side view in FIG. 12R and in a top view in FIG. 12S. The cannula bevel 12306 includes three surfaces, a curved proximal surface 12316, a flat middle surface 12326, and a curved distal surface 12336. In certain embodiments, the surface 12326 can be parallel to the central axis of the shaft 1210. In certain embodiments the surface 12326 can form a non-zero angle relative to the longitudinal axis of the shaft 1210 at the location of the surface 12326. In certain embodiments, the heel 12346 and inner edge 12376 can be rounded to prevent damage to a flexible catheter passing through the bevel 12306. In certain embodiments, the distal outer edge 12396 of the bevel can be sharp to penetrate solid tissue.

Figure 12T:
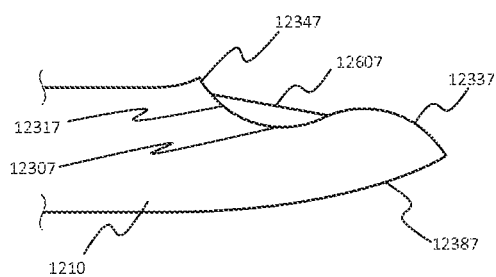
FIG. 12T is a schematic diagram showing a needle bevel and a stylet bevel configured for the introduction of a catheter into a living body.
Figure 12U:
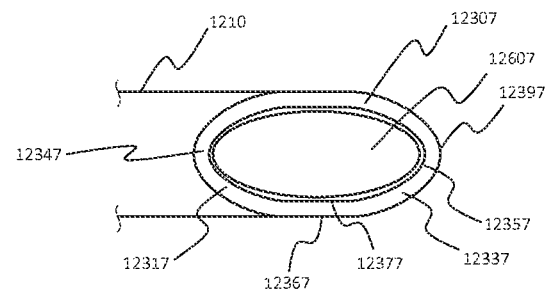
FIG. 12U is a schematic diagram showing a needle bevel and a stylet bevel configured for the introduction of a catheter into a living body.

Referring to FIGS. 12T and 12U, certain embodiments of a bevel 12307 for an epidural needle 1200 and a bevel 12607 for an epidural stylet 1250 are presented in a side view in FIG. 12T and in a top view in FIG. 12U. The cannula bevel 12307 includes two surfaces, a curved proximal surface 12317 and a curved distal surface 12337. In certain embodiments, the heel 12347 and inner edge 12377 can be rounded to prevent damage to a flexible catheter passing through the bevel 12307. In certain embodiments, the distal outer edge 12397 of the bevel can be sharp to penetrate solid tissue. The shaft 1210 can include a gentle bend 12387 at the position of the bevel 12307. In certain embodiments, the stylet bevel 12607 can be a flat surface that is aligned with and substantially parallel to the average orientation of the cannula bevel 12307.

Figure 12V:
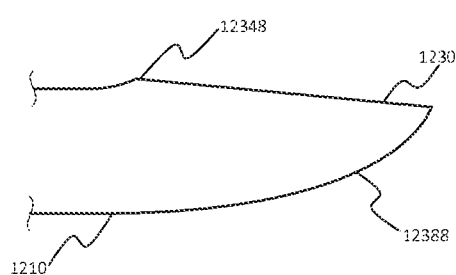
FIG. 12V is a schematic diagram showing a needle bevel and a stylet bevel configured for the introduction of a catheter into a living body.
Figure 12W:
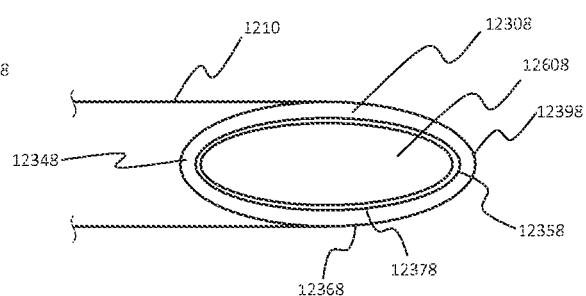
FIG. 12W is a schematic diagram showing a needle bevel and a stylet bevel configured for the introduction of a catheter into a living body.

Referring to FIGS. 12V and 12W, certain embodiments of a bevel 12308 for an epidural needle 1200 and a bevel 12608 for an epidural stylet 1250 are presented in a side view in FIG. 12V and in a top view in FIG. 12W. The cannula bevel 12308 is a flat surface that has an angle relative to the transverse plane of the shaft 1210 at the location of the bevel 12308. The shaft 1210 includes a gentle bend 12388 at the position of the bevel 12308. In certain embodiments, the stylet bevel 12608 can be a flat surface that is substantially parallel and aligned with the cannula bevel 12308. In certain embodiments, the bevels 12308 and 12608 can be a touhy bevel. In certain embodiments, the heel 12348 and inner edge 12378 can be rounded to prevent damage to a flexible catheter passing through the bevel 12308. In certain embodiments, the distal outer edge 12398 of the bevel can be sharp to penetrate solid tissue.

Figure 12X:
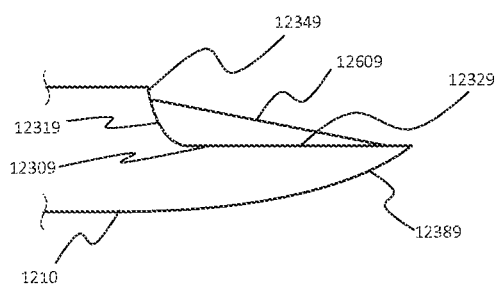
FIG. 12X is a schematic diagram showing a needle bevel and a stylet bevel configured for the introduction of a catheter into a living body.
Figure 12Y:
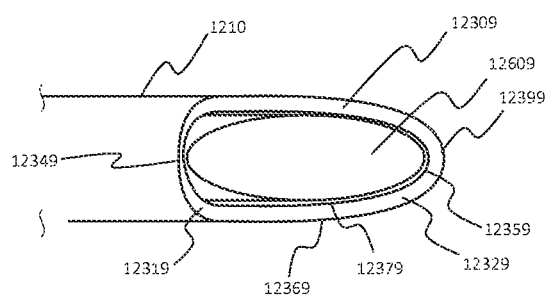
FIG. 12Y is a schematic diagram showing a needle bevel and a stylet bevel configured for the introduction of a catheter into a living body.

Referring to FIGS. 12X and 12Y, certain embodiments of a bevel 12309 for an epidural needle 1200 and a bevel 12609 for an epidural stylet 1250 are presented in a side view in FIG. 12X and in a top view in FIG. 12Y. The cannula bevel 12309 includes a curved proximal surface 12319 and a flat distal surface 12329. In certain embodiments, the proximal surface 12319 can be flat. In certain embodiments, the distal surface 12329 can be parallel to the central axis of the shaft 1210. The shaft 1210 includes a gentle bend 12389 opposite the bevel 12309. In certain embodiments, the heel 12349 and inner edge 12379 can be rounded to prevent damage to a flexible catheter passing through the bevel 12309. In certain embodiments, the distal outer edge 12399 of the bevel can be sharp to penetrate solid tissue. The stylet bevel 12609 is a flat surface. The stylet bevel 12609 can be configured to occlude the opening in the distal end of the shaft 1210. The stylet bevel can be aligned with the opening at the distal end of the shaft 1210.

In certain embodiments, the needle 1200 does not include electrical insulation 1215. In certain embodiments, the needle 1200 is an epidural needle. In certain embodiments, the bevel geometries presented in FIGS. 12F, 12G, 12H, 12I, 12J, 12K, 12L, 12M, 12N, 12O, 12P, 12Q, 12R, 12S, 12T, 12U, 12V, 12W, 12X, and 12Y can be included in an epidural needle that does not include electrical insulation. In certain embodiments, the bevel geometries presented in FIGS. 12F, 12G, 12H, 12I, 12J, 12K, 12L, 12M, 12N, 12O, 12P, 12Q, 12R, 12S, 12T, 12U, 12V, 12W, 12X, and 12Y can include addition cut surfaces, such as a blunted distal tip.

Figure 13:
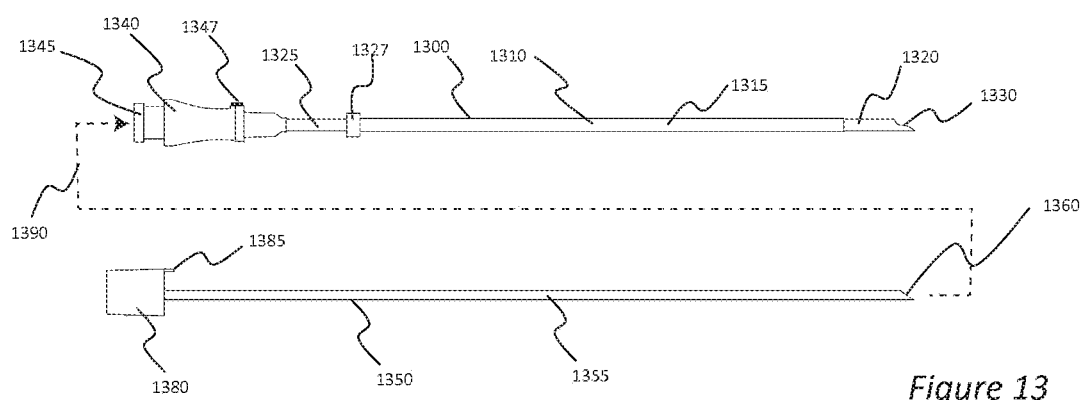
FIG. 13 is a schematic diagram showing a cannula system configured for the introduction of a catheter into the living body, wherein the cannula has a depth stop and a conductive region configured for attachment to an electrical generator.

Referring now to FIG. 13, FIG. 13 presents certain embodiments of an epidural RF cannula system, which includes a hollow needle 1300 and a stylet 1350, wherein the needle 1300 includes a proximal length 1325 of the shaft 1310 that is uninsulated, in accordance with several aspects of the present invention. In certain embodiments, the cannula system 1300 and 1350 can be configured for the systems and methods related to catheter systems presented in the embodiments presented in relation to FIG. 1. In certain embodiments, the cannula system 1300 and 1350 can be configured for the systems and methods related to catheter systems presented in the embodiments presented in relation to FIG. 1D. In certain embodiments, the cannula 1300 is configured to provide for connection to one output pole of an RF generator, such as the reference jack.

The cannula 1300 includes a port 1345 at its proximal end, a hub 1340, a marker 1347 that indicates the orientation of the bevel 1330, a hollow metal shaft 1310, a proximal portion 1325 of the shaft 1310 that is not covered by electrical insulation, a depth stop 1327, electrical insulation 1315 covering a middle portion of the shaft 1310, an active tip 1320 at the distal end of the shaft 1310 that is not covered by electrical insulation, and an epidural bevel 1330. The stylet 1350 includes a proximal cap 1380, an alignment feature 1385 that is configured to engage with the cannula hub 1340 and thereby align the bevel 1360 of the stylet 1350 and the bevel 1330 of the needle 1300, a shaft 1355, and a bevel 1360 at the distal end of the shaft 1355. FIG. 13 presents the cannula 1300 and stylet 1350 separately in an external view from the side of the bevel, and arrow 1390 shows how the stylet 1350 can be engaged with the cannula 1300. One output pole of an electrical power supply, such as the reference pole of an RF generator can be attached to the connection section 1325, for example, by means of an alligator clip. The depth stop can prevent the connection section 1325 from being advanced into living tissue when the cannula 1300 is used to penetrate said living tissue, such as the human body. The depth stop can be constructed from an electrically-insulative material, such as plastic, to prevent electrical signals applied to section 1325 from being conducted to living tissue through the depth stop 1325. In certain embodiments, the depth stop is electrically-isolated from the connection point 1325. Electrical signals applied to the connection point 1325 conduct through the shaft 1310 to the active tip 1320. The needle 1300 can be used as the needle 170 in FIG. 1D, and connection 175 can be the junction between the uninsulated length 1325 and a cable connected to one output pole of an RF generator; in this example, when a catheter electrode passing through the needle 1300 is connected to the opposite output pole of the RF generator, the active tip of the electrode is not in contact with the shaft 1310, and both the active tip of the electrode and the active tip 1320 of the needle 1300 are in contact with the human body, electrical current flows between the active tip 1320 of the needle 1300 and the active tip of the catheter electrode.

Figure 14:
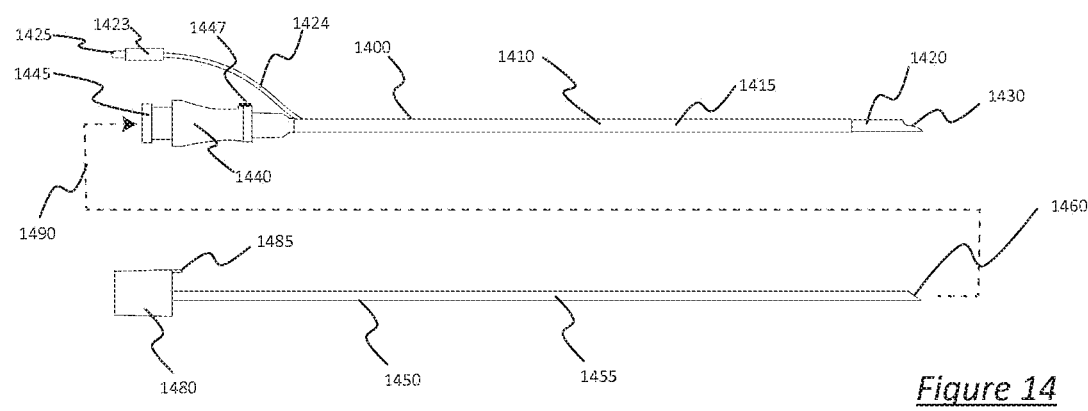
FIG. 14 is a schematic diagram showing a cannula system configured for the introduction of a catheter into the living body, wherein the cannula has a connection cable configured for attachment to an electrical generator.

Referring now to FIG. 14, FIG. 14 presents certain embodiments of an epidural RF cannula system, which includes a hollow needle 1400 and a stylet 1450, wherein the needle 1400 include as connection to an electrical power supply 1425, in accordance with several aspects of the present invention. In certain embodiments, the cannula system 1400 and 1450 can be configured for the systems and methods related to catheter systems presented in the embodiments presented in relation to FIG. 1. In certain embodiments, the cannula system 1400 and 1450 can be configured for the systems and methods related to catheter systems presented in the embodiments presented in relation to FIG. 1D. In certain embodiments, the cannula 1400 is configured to provide for connection to one output pole of an RF generator, such as the reference jack.

The cannula 1400 includes a port 1445 at its proximal end, a hub 1440, a marker 1447 that indicates the orientation of the bevel 1430, a hollow conductive shaft 1410, a conductive connector 1425, electrically-insulative housing for the connector 1423, a flexible cable 1424 that can conduct electricity between the connector 1423 and the shaft 1410, electrical insulation 1415 covering a middle portion of the shaft 1410, an active tip 1420 at the distal end of the shaft 1410 that is not covered by electrical insulation, and an epidural bevel 1430. The stylet 1450 includes a proximal cap 1480, an alignment feature 1485 that is configured to engage with the cannula hub 1440 and thereby align the bevel 1460 of the stylet 1450 and the bevel 1430 of the needle 1400, a shaft 1455, and a bevel 1460 at the distal end of the shaft 1455. The conductive shaft 1410 can be constructed from a metal, such as stainless steel. FIG. 14 presents the cannula 1400 and stylet 1450 separately in an external view from the side of the bevel, and arrow 1490 shows one method by which the stylet 1450 can be engaged with the cannula 1400. One output pole of an electrical power supply, such as the reference pole of an RF generator can be attached to the connector 1423, for example, by means of an alligator clip. Electrical signals applied to the connector 1423 conduct through the cable 1424 to the shaft 1410, and from the shaft 1410 to the active tip 1420. The needle 1400 can be used as the needle 170 in FIG. 1D, and connection 175 can be the junction between the pin 1423 and a cable connected to one output pole of an RF generator; in this example, when a catheter electrode passing through the needle 1300 is connected to the opposite output pole of the RF generator, and the active tip of the electrode is not in contact with the shaft 1410, and both the electrode's active tip and the needle active tip 1420 are in contact with the human body, electrical current flows between the active tip 1420 of the needle 1400 and the active tip of the catheter electrode.

In certain embodiments, the invention presented here can relate to medical catheters in general, including catheters configured for placement in a particular bodily location or locations, such as the epidural space, bodily spaces, bodily cavities, bodily potential spaces, between layers of tissue, blood vessels, the urinary tract, the urethra, the ureter, the renal pelvis, the vagina, the uterus, the fallopian tubes, the digestive tract. The invention presented here can relate to medical electrodes, including RF electrodes and stimulation electrodes, including electrodes configured for placement in the epidural space, in bodily spaces, in bodily cavities, in bodily potential spaces, between layers of tissue, in blood vessels, in the urinary tract, in the urethra, in the ureter, in the renal pelvis, in the vagina, in the uterus, in the fallopian tubes, in the digestive tract. Although the present invention is described with several particular embodiments, various changes and modifications can be suggested by one skilled in the art. In particular, the present invention is described with reference to certain polymers and materials and methods of processing those materials, but can apply to other types of processing and materials with little alteration and similar results. Furthermore, the present invention contemplates several process steps that may be performed either in the sequence described or in an alternative sequence without departing from the scope and the spirit of the present invention. The present invention is intended to encompass such changes and modification as they fall within the scope and the spirit of the appended claims.

What is claimed:

1. A system comprising:
   a catheter;
   an injection adaptor for the catheter; and
   an electrode,
   the catheter having a proximal end and a distal end and including a catheter lumen, the catheter lumen having a proximal opening at a proximal end of the catheter and a distal opening at a distal end of the catheter,
   the injection adaptor including an adaptor lumen connecting a distal first port and a proximal second port of the adaptor,
   the first port forming a first seal with the proximal opening of the catheter lumen, the second port being configured to form a second seal with the electrode when the electrode is inserted through the second port, the first seal being a fluid-tight seal, the second seal being a fluid-tight seal, and the second seal comprising a clamp configured to be actuated to releasably fix the electrode to the injection adaptor,
   the electrode including an elongated shaft insertable through the second port and into the catheter lumen.

2. The system of claim 1, wherein the injection adaptor includes a third port connected to the adaptor lumen and in fluid communication therewith, such that fluid injected into the third port flows into the catheter lumen.

3. The system of claim 1, wherein the electrode comprises a stylet having a stylet port for injection of fluid therethrough and a channel extending distally from the stylet port to the adaptor lumen, such that fluid injected into the stylet port flows into the adaptor lumen when the electrode is inserted through the second port and the second port forms the second seal with the electrode.

4. The system of claim 1, wherein the electrode comprises a stylet having a stylet port for injection of fluid therethrough and a channel extending distally from the stylet port to the catheter lumen, such that fluid injected into the stylet port flows into the catheter lumen when the electrode is inserted through the second port, the second port forms the second seal with the electrode, and the first port forms the first seal with the proximal opening of the catheter lumen.

5. The system of claim 1, wherein the catheter is an epidural catheter.

6. The system of claim 1, wherein the first fluid-tight seal is releasable and resealable.

7. The system of claim 1, wherein the adaptor includes a tuohy-borst adaptor.

8. The system of claim 1, wherein the first seal is a permanent connection.

9. The system of claim 1, wherein the second seal is a permanent connection.

10. The system of claim 1, wherein the electrode permits electrical signals to be conducted to an active tip of the catheter.

11. The system of claim 1, wherein the first seal comprises a clamp configured to be actuated to releasably fix the catheter to the injection adaptor.

* * * * *